(12) United States Patent
Burnouf et al.

(10) Patent No.: US 6,962,912 B2
(45) Date of Patent: Nov. 8, 2005

(54) SUBSTITUTED PYRAZOLO[4,3-E] DIAZEPINES, PHARMACEUTICAL COMPOSITIONS CONTAINING THEM, USE AS MEDICINAL PRODUCTS AND PROCESSES FOR PREPARING THEM

(75) Inventors: Catherine Burnouf, Morsang sur Orge (FR); Amaya Berecibar, Bourg la Reine (FR); Michael Navet, Marcoussis (FR)

(73) Assignee: Warner-Lambert LLC, Morris Plains, NJ (US)

( * ) Notice: Subject to any disclaimer, the term of this patent is extended or adjusted under 35 U.S.C. 154(b) by 80 days.

(21) Appl. No.: 10/169,375

(22) PCT Filed: Dec. 27, 2000

(86) PCT No.: PCT/EP00/13380

§ 371 (c)(1),
(2), (4) Date: Oct. 21, 2002

(87) PCT Pub. No.: WO01/49689

PCT Pub. Date: Jul. 12, 2001

(65) Prior Publication Data

US 2003/0171364 A1 Sep. 11, 2003

Related U.S. Application Data
(60) Provisional application No. 60/209,339, filed on Jun. 5, 2000.

(30) Foreign Application Priority Data

Jan. 5, 2000 (FR) ............................................ 00 00095

(51) Int. Cl.$^7$ ..................... A61P 35/00; A61K 31/5517; C07D 487/04; C07D 243/00; C07D 231/00
(52) U.S. Cl. ........................ 514/221; 540/501; 540/568
(58) Field of Search .......................... 514/221; 540/501, 540/568

(56) References Cited

U.S. PATENT DOCUMENTS 3,764,688 A   10/1973 Swett et al. ................. 424/274

OTHER PUBLICATIONS

Goel et al. (Synthesisf (1987), (2), 162–164). Abstract.*
Baraldi, Pier, et. al., "Synthesis and Interaction of 5-(Substituted-phenyl)-3-methyl-6,7-dihydropyrazolo[4,3-e][1,4]diazepin-8(7H)-ones with Benzodiazepine Receptors in Rat Cerebral Cortex" Journal of Medicinal Chemistry vol. 28, No. 5, 1985 pp 683–685.
Beavo, Joseph A. et. al. "Primary sequence of cyclic nucleotide phosphodiesterase isozymes and the design of selective inhibitors," Trends Pharmacol. Sci., vol. 11, 1990, pp. 150–155.
Beavo, Joseph A., "Multiple Cyclic Nucleotide Phosphodiesterases," Molecular Pharmacology, 1994, pp. 399–405.
Chen, Yan–Lian, et. al., "Anti–tumor necrosis factor properties of non–peptide drugs in acute–phase responses," European Journal of Pharmacology, vol. 271, 1994, pp. 319–327.
Prabhakar, Uma, et. al., Characterization of cAMP–Dependent Inhibition of LPS–induced TNFα Production by Rolipram, A Specific Phosphodiesterase IV (PDE IV) Inhibitor, Int. J. Immunopharmac., vol. 16, No. 10, 1994, pp. 805–816.
Corrigan, C.J., et. al., "T cells and eosinophils in the pathogenesis of asthma," Immunology Today, vol. 13, No. 12, 1992, pp. 501–507.
Elwood, W., et al., "Inhibition of allergen–induced lung eosinophilla by type III and combined type III– and IV–selective Phosphodiesterase inhibitors in Brown–Norway Rats," Inflamm Res. vol. 44, 1995, pp. 83–86.
Suter, Peter M., et. al., "High Bronchoalveolar Levels of Tumor Necrosis Factor and Its Inhibitors, Interleukin–1, Interferon, and Elastase, in Patients with Adult Respiratory Distress Syndrome after Trauma, Shock, or Sepsis," Am. Rev. Respir. Dis., vol. 145, 1992, pp. 1016–1022.
Martin, Thomas R., et. al., "The Role of Chemokines in the Pathophysiology of the Acute Respiratory Distress Syndrome (ARDS)," Chemokines in Disease: Biology and Clinical Research, Chapter 6, 1999, pp. 81–110.
Repine, John E., et. al., "Neutrophils and Adult Respiratory Distress Syndrome: Two Interlocking Perspectives in 1991," Am. Rev. Respir. Dis., vol. 144, 1991, pp. 251–252.
Cardelus, Ignasi, et. al., "Inhibition of lipopolysaccharide–induced bowel erythrocyte extravasation in rats, and of mesenteric hypoperfusion in dogs, by phosphodiesterase inhibitors," European Journal of Pharmacology, vol. 299, 1996, pp. 153–159.

* cited by examiner

Primary Examiner—Bruck Kifle
(74) Attorney, Agent, or Firm—Peter C. Richardson; Gregg C. Benson; Robert T. Ronau

(57) ABSTRACT

The invention relates to novel substituted pyrazolo[4,3-e]-diazepines of general formula:

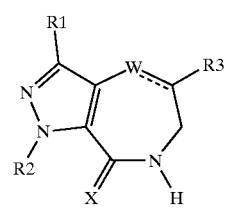

to pharmaceutical compositions containing them, to their use as medicinal products and to processes for preparing them.

12 Claims, No Drawings

SUBSTITUTED PYRAZOLO[4,3-E] DIAZEPINES, PHARMACEUTICAL COMPOSITIONS CONTAINING THEM, USE AS MEDICINAL PRODUCTS AND PROCESSES FOR PREPARING THEM

This application is a nonprovisional application for patent filed under 35 U.S.C. §371, which is a nationalization of PCT International Application number PCT/EP00/13380 filed Dec. 27, 2000, which claims benefit of priority from U.S. provisional application No. 60/209,339 filed Jun. 5, 2000, and French patent application number 00/00095 filed Jan. 5, 2000.

The invention relates to novel substituted pyrazolo-[4,3] diazepins, to pharmaceautical compositions containing them, to their use as medical products and to processes for preparing them.

TECHNOLOGICAL BACKGROUND OF THE INVENTION

Cyclic adenosine 3',5'-monophosphate (cAMP) is a ubiquitous intracellular second messenger, which is intermediate between a first messenger (hormone, neurotransmitter or autacoid) and the cellular functional responses: the first messenger stimulates the enzyme responsible for the synthesis of cAMP; depending on the cells concerned, the cAMP then intervenes in a great number of functions: metabolic, contractile or secretory.

The effects of cAMP end when it is degraded by cyclic nucleotide phosphodiesterases, which are intracellular enzymes that catalyse its hydrolysis into inactive adenosine 5'-monophosphate.

At least 11 major families of cyclic nucleotide phosphodiesterases (PDE) have been distinguished in mammals, numbered from 1 to 11 according to their structure, their kinetic behaviour, their substrate specificity or their sensitivity to effectors (Beavo J. A. et al. (1990) Trends Pharmacol. Sci. 11, 150–155. Beavo J. A. et al. (1994) Molecular Pharmacol. 46, 399–405). The PDE4 enzymes are specific for cAMP.

Non-specific phosphodiesterase inhibitor compounds are known, which inhibit several families of enzymes. This is the case for certain methyl xanthines such as theophylline. These compounds have a low therapeutic index, in particular on account of their action on types of PDE present in cells other than the target cells. Conversely, certain families of PDE can be selectively inhibited by various pharmacological agents: the hydrolysis of cyclic nucleotides is slowed down and their concentration thus increases in only the cells in which the type of PDE that is sensitive to the inhibitor is found.

A specific advantage is shown for the phosphodiesterases 4 (PDE4), which have been identified in many tissues including the central nervous system, the heart, vascular endothelium, vascular smooth muscle and that of the aerial pathways, myeloid lines and lymphoid lines.

An increase in cAMP in the cells involved in inflammation inhibits their activation: inhibition of the synthesis and release of mediators in mastocytes, monocytes, polymorphonuclear eosinophils and basophils, inhibition of chemotaxis and degranulation of polymorphonuclear neutrophils and eosinophils, inhibition of the proliferation and differentiation of lymphocytes.

Cytokines, in particular TNF and interleukins, produced by various types of leukocytes such as the T lymphocytes, monocytes and polymorphonuclear eosinophils, play an important role in triggering inflammatory manifestations, in particular in response to stimulation by an allergen in the respiratory pathways.

Moreover, cAMP reduces the tonus of the smooth muscle fibres in the aerial pathways.

It might thus be expected that selective PDE4 inhibitors would have therapeutic activity as anti-inflammatory and anti-allergic medicinal products, and in the treatment of various respiratory diseases such as asthma, emphysema and chronic bronchitis.

Extensive research has been conducted for several years into the production and development of powerful PDE4 inhibitors. This is found to be difficult due to the fact that many potential PDE4 inhibitors are not devoid of activity on the phosphodiesterases of other families.

At the present time, the lack of selectivity of PDE4 inhibitors thus represents a major problem, given the extent of the functions regulated by cAMP. There is thus a need for powerful and selective PDE4 inhibitors, i.e. inhibitors which have no action with respect to PDEs belonging to other families and particularly PDEs which regulate cGMP.

SUMMARY OF THE INVENTION

The invention relates to substituted pyrazolo[4,3-e]-diazepines of general formula I below:

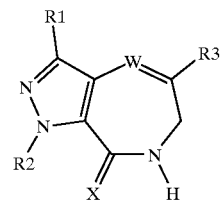

in which:
R1 is chosen from the following groups:
hydrogen;
linear or branched alkyl containing from 1 to 6 carbon atoms;
cycloalkyl containing from 3 to 6 carbon atoms;
alkylcycloalkyl comprising an alkyl group containing from 1 to 6 carbon atoms and a cycloalkyl group containing from 3 to 6 carbon atoms;
aryl containing from 5 to 10 carbon atoms, optionally interrupted with a hetero atom chosen from nitrogen, oxygen and sulphur;
arylalkyl containing from 6 to 10 carbon atoms, optionally interrupted with a hetero atom chosen from nitrogen, oxygen and sulphur;
alkylaryl containing from 6 to 10 carbon atoms, optionally interrupted with a hetero atom chosen from nitrogen, oxygen and sulphur;
linear or branched alkenyl containing from 2 to 6 carbon atoms;
the groups $(CH_2)_nOR_B$, $(CH_2)_nCF_3$, $(CH_2)_nC(O)R_B$, $(CH_2)_nCOOR_B$, $(CH_2)_nOC(O)R_A$, $(CH_2)_nSR_B$, $(CH_2)_nC(S)R_B$, $(CH_2)_nC(S)OR_B$, $(CH_2)_nC(S)SR_B$, $(CH_2)_nNR_BR_C$, $(CH_2)_nC(O)NR_BR_C$, $(CH_2)_nNR_CC(O)R_B$, $(CH_2)_nNR_DC(O)NR_DR_B$ or $(CH_2)_nZ$, in which,
$R_A$ is chosen from linear or branched alkyl containing from 1 to 6 carbon atoms;
cycloalkyl containing from 3 to 6 carbon atoms;
alkylcycloalkyl comprising an alkyl group containing from 1 to 6 carbon atoms and a cycloalkyl group containing from 3 to 6 carbon atoms;

aryl containing from 5 to 10 carbon atoms, optionally interrupted with a hetero atom chosen from nitrogen, oxygen and sulphur;
arylalkyl containing from 6 to 10 carbon atoms, optionally interrupted with a hetero atom chosen from nitrogen, oxygen and sulphur;
alkylaryl containing from 6 to 10 carbon atoms, optionally interrupted with a hetero atom chosen from nitrogen, oxygen and sulphur;
linear or branched alkenyl containing from 2 to 6 carbon atoms;
$R_B$ and $R_C$, which may be identical or different, are chosen from: hydrogen;
linear or branched alkyl containing from 1 to 6 carbon atoms;
cycloalkyl containing from 3 to 6 carbon atoms;
alkylcycloalkyl comprising an alkyl group containing from 1 to 6 carbon atoms and a cycloalkyl group containing from 3 to 6 carbon atoms;
aryl containing from 5 to 10 carbon atoms, optionally interrupted with a hetero atom chosen from nitrogen, oxygen and sulphur;
arylalkyl containing from 6 to 10 carbon atoms, optionally interrupted with a hetero atom chosen from nitrogen, oxygen and sulphur;
alkylaryl containing from 6 to 10 carbon atoms, optionally interrupted with a hetero atom chosen from nitrogen, oxygen and sulphur;
linear or branched alkenyl containing from 2 to 6 carbon atoms, it being possible for $R_B$ and $R_C$ to form a ring containing from 5 to 7 atoms which can include one or more hetero atoms chosen from S, N and O;
$R_D$ is hydrogen or linear or branched alkyl containing from 1 to 6 carbon atoms;
Z is a halogen; and
n is an integer from 0 to 4 inclusive;
R2 is chosen from the following groups:
linear or branched alkyl containing from 1 to 6 carbon atoms;
alkylcycloalkyl comprising an alkyl group containing from 1 to 6 carbon atoms and a cycloalkyl group containing from 3 to 6 carbon atoms;
cycloalkyl containing from 3 to 6 carbon atoms; aryl containing from 5 to 10 carbon atoms, optionally interrupted with a hetero atom chosen from nitrogen, oxygen and sulphur;
alkylaryl containing from 6 to 10 carbon atoms, optionally interrupted with a hetero atom chosen from nitrogen, oxygen and sulphur;
linear or branched alkenyl containing from 2 to 6 carbon atoms;
the groups $(CH_2)_mOR_B$, $(CH_2)_nCF_3$, $(CH_2)_mC(O)R_B$, $(CH_2)_mCOOR_B$, $(CH_2)_mOC(O)R_A$, $(CH_2)_mSR_B$, $(CH_2)_mC(S)R_B$, $(CH_2)_mC(S)OR_B$, $(CH_2)_mC(S)SR_B$, $(CH_2)_mNR_BR_C$, $(CH_2)_mC(O)NR_BR_C$, $(CH_2)_mNR_CC(O)R_B$, $(CH_2)_mNR_DC(O)NR_DR_B$ or $(CH_2)_mZ$, in which,
$R_A$, $R_B$, $R_C$ $R_D$ and Z are as defined above, and
m is an integer from 1 to 4 inclusive;
n is an integer from 0 to 4 inclusive;
R3 is chosen from the following groups:
hydrogen;
linear or branched alkyl containing from 1 to 6 carbon atoms;
cycloalkyl containing from 3 to 6 carbon atoms;
alkylcycloalkyl comprising an alkyl group containing from 1 to 6 carbon atoms and a cycloalkyl group containing from 3 to 6 carbon atoms;
aryl containing from 5 to 10 carbon atoms, optionally interrupted with a hetero atom chosen from nitrogen, oxygen and sulphur;
arylalkyl containing from 6 to 10 carbon atoms, optionally interrupted with a hetero atom chosen from nitrogen, oxygen and sulphur;
alkylaryl containing from 6 to 10 carbon atoms, optionally interrupted with a hetero atom chosen from nitrogen, oxygen and sulphur;
linear or branched alkenyl containing from 2 to 6 carbon atoms;
the groups $(CH_2)_nOR_B$, $(CH_2)_nCF_3$, $(CH_2)_nC(O)R_B$, $(CH_2)_nCOOR_B$, $(CH_2)_nOC(O)R_A$, $(CH_2)_nSR_B$, $(CH_2)_nC(S)R_B$, $(CH_2)_nC(S)OR_B$, $(CH_2)_nC(S)SR_B$, $(CH_2)_nNR_BR_C$, $(CH_2)_nC(O)NR_BR_C$, $(CH_2)_nNR_CC(O)R_B$, $(CH_2)_nNR_DC(O)NR_DR_B$ or $(CH_2)_nZ$, in which,
$R_A$, $R_B$, $R_C$ $R_D$ and n are as defined above;
the aryl, arylalkyl and alkylaryl groups defined above being unsubstituted or substituted on the aryl group with 1, 2 or 3 groups chosen from:
halogen, hydroxyl, NO, $NO_2$, CN, alkoxy containing from 1 to 4 carbon atoms, $(CH_2)_nOR_B$, $(CH_2)_nNR_BR_C$, $(CH_2)_nNC(O)R_B$, $(CH_2)_nHNSO_2R_B$, $(CH_2)_nN(SO_2R_B)_2$, $CO_2R_B$, $CF_3$ and

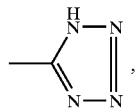

in which $R_B$, $R_C$ and n are as defined above; and
the dotted line present in formula I indicates that the bond between W and the carbon in position 5 may be:
a single bond, in which case W represents a nitrogen atom substituted with a hydrogen atom,
a double bond, and in this case W represents an unsubstituted nitrogen atom;
X is S, O, N—CN or N—$R_B$ in which $R_B$ is as defined above;
as well as the oxides, the tautomeric forms and the corresponding optical isomers or the pharmaceutically acceptable derivatives of the compounds of formula I, with the proviso that when
R1 represents a methyl group, R2 an ethyl group, W is N, X is an oxygen atom and the bond between W and the carbon in position 5 is a double bond, then
R3 is neither an unsubstituted phenyl group nor a phenyl group bearing a fluorine atom in an ortho position as sole substituent.

The compounds of the invention have inhibitory properties on PDE4 and/or TNFα-release. Some of these compounds are also selective inhibitors of PDE4 subtypes. The compounds of the invention can be used in the treatment of complaints including cancer, acquired immunodeficiency syndrome, fibrosis, excessive scarring including excessive dermal scarring such as normal or abnormal dermal scarring following wounding or surgery, osteoarthritis, osteoporosis, multiple sclerosis, anxiety, depression, atopic dermatitis, rheumatoid arthritis, septic shock, immune diseases including disseminated lupus erythematous, psoriasis, graft rejection and allergic rhinitis, as well as diseases involving the production of TNFα and more particularly in the treatment of inflammatory complaints such as asthma, chronic obstructive bronchopneumopathy (COPD), post-ischaemic lesions, pulmonary hypertension, congestive cardiac insufficiency, acute respiratory distress syndrome, and chronic inflammatory diseases of the intestine (IBD) such as Crohn's disease and ulcerative colitis.

The invention also relates to a process for synthesizing a compound of general formula I, the said process being characterized in that it comprises:

1) when, in formula I, X is O or S, W is N and the bond between W and the carbon in position 5, symbolized by ═, is a double bond:
the cyclization of a compound of general formula (C)

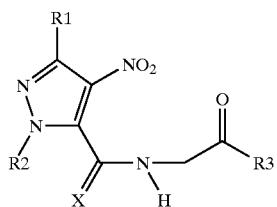

(C)

in which R1, R2, R3 and X have the meaning given above, to give a synthetic intermediate or a final compound of general formula D,

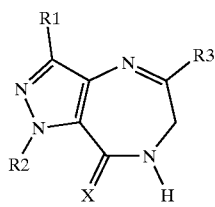

(D)

in which R1, R2, R3 and X have the meanings given above;

2) when, in formula I, X is S, W is N and the bond between W and the carbon in position 5, symbolized by ═, is a double bond:
the thionation of a compound of general formula (D), in which R1, R2 and R3 have the meaning given above and X is O, to give a compound of formula I in which the bond between W and the carbon atom in position 5 is a double bond, W is N and X is sulphur;

3) when, in formula I, X is N—CN, W is N and the bond between W and the carbon in position 5, symbolized by ═, is a double bond:
the reaction of a compound of general formula (G)

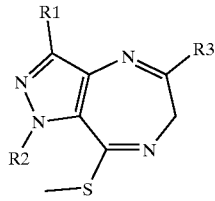

(G)

in which R1, R2 and R3 have the meaning given above, with a compound of formula H₂N—CN, to give a compound of general formula F below:

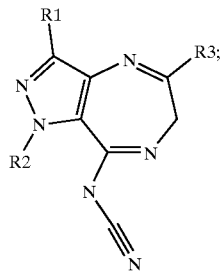

(F)

4) when, in formula I, X is N—R$_B$, W is N and the bond between W and the carbon in position 5, symbolized by ═, is a double bond:
the reaction of a compound of general formula (G)

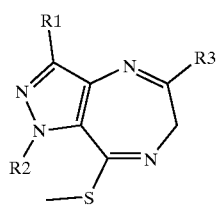

(G)

in which R1, R2 and R3 are as defined above, with a compound of formula H₂N—R$_B$, in which R$_B$ is as defined above,
to give a compound of formula I in which the bond between W and the carbon atom in position 5 is a double bond, W is N and X is N—R$_B$ (J. Med. Chem.; 42; 1999; 2909–2919).

5) when, in formula I, W is NH and the bond between W and the carbon in position 5 is a single bond
the reaction of a compound of general formula

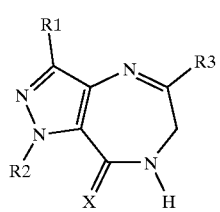

(D)

in which R1, R2, R3 and X are as defined above, with a reducing agent, to give a compound of formula I in which W is NH and the bond between W and the carbon in position 5 is a single bond.

The invention also relates to a pharmaceutical composition comprising at least one compound of general formula I as defined above, in combination with a pharmaceutically acceptable support.

The invention also relates to the use of a substituted pyrazolo[4,3-e]diazepine of general formula I as a medicinal product.

The invention also relates to the use of a substituted pyrazolo[4,3-e]diazepine of general formula I to prepare a medicinal product for treating complaints relating to a therapy with a phosphodiesterase 4 inhibitor.

The invention also relates to a method for treating a disease or a complaint relating to a therapy with a phosphodiesterase 4 inhibitor, the said method comprising the administration of an effective concentration of a compound of formula I to a patient.

The invention also relates to the use of a substituted pyrazolo[4,3-e]diazepine of general formula I for the preparation of a medicinal product intended for treating mammals and particularly for treating humans, especially a medicinal product intended for treating conditions including cancer, acquired immunodeficiency syndrome, fibrosis, excessive scarring including excessive dermal scarring such as normal or abnormal dermal scarring following wounding or surgery, osteoarthritis, osteoporosis, multiple sclerosis, anxiety, depression, atopic dermatitis, rheumatoid arthritis, septic shock, immune diseases including disseminated lupus erythematous, psoriasis, graft rejection, allergic rhinitis, diseases involving the production of TNFα and more particularly inflammatory complaints such as asthma, chronic obstructive bronchopneumopathy (COPD), post-ischaemic lesions, pulmonary hypertension, congestive cardiac insufficiency, acute respiratory distress syndrome, and chronic inflammatory diseases of the intestine (IBD) such as Crohn's disease and ulcerative colitis.

DETAILED DESCRIPTION OF THE INVENTION

The present invention thus relates to the compounds of general formula I:

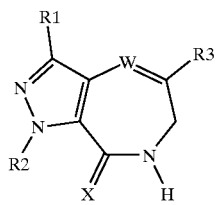

I in which the dotted line, X, W, R1, R2 and R3 are as defined above.

The compounds of formula I above in which W represents an unsubstituted nitrogen atom and the bond between W and the carbon in position 5, symbolized by =, is a double bond, are preferred.

Among the compounds of general formula I that are thus preferred are the compounds corresponding to the general formula II:

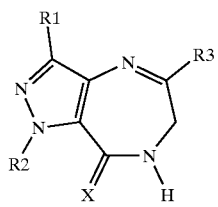

II in which:
R1 is a linear or branched alkyl group containing from 1 to 6 carbon atoms;
a cycloalkyl group containing from 3 to 6 carbon atoms;
an alkylcycloalkyl group comprising an alkyl group containing from 1 to 6 carbon atoms and a cycloalkyl group containing from 3 to 6 carbon atoms;
an aryl group containing from 5 to 10 carbon atoms, optionally interrupted with a hetero atom chosen from nitrogen, oxygen and sulphur;

an arylalkyl group containing from 6 to 10 carbon atoms, optionally interrupted with a hetero atom chosen from nitrogen, oxygen and sulphur;
an alkylaryl group containing from 6 to 10 carbon atoms, optionally interrupted with a hetero atom chosen from nitrogen, oxygen and sulphur;
a linear or branched alkenyl group containing from 2 to 6 carbon atoms;
the groups $(CH_2)_nOR_B$, $(CH_2)_nCF_3$, $(CH_2)_nC(O)R_B$, $(CH_2)_nCOOR_B$, $(CH_2)_nOC(O)R_A$, $(CH_2)_nSR_B$, $(CH_2)_nNR_BR_C$, $(CH_2)_nC(O)NR_BR_C$, $(CH_2)_nNR_CC(O)R_B$ or $(CH_2)_nZ$, in which
$R_A$ is chosen from linear or branched alkyl containing from 1 to 6 carbon atoms;
cycloalkyl containing from 3 to 6 carbon atoms;
alkylcycloalkyl comprising an alkyl group containing from 1 to 6 carbon atoms and a cycloalkyl group containing from 3 to 6 carbon atoms;
aryl containing from 5 to 10 carbon atoms, optionally interrupted with a hetero atom chosen from nitrogen, oxygen and sulphur;
arylalkyl containing from 6 to 10 carbon atoms, optionally interrupted with a hetero atom chosen from nitrogen, oxygen and sulphur;
alkylaryl containing from 6 to 10 carbon atoms, optionally interrupted with a hetero atom chosen from nitrogen, oxygen and sulphur;
linear or branched alkenyl containing from 2 to 6 carbon atoms;
$R_B$ and $R_C$, which may be identical or different, are chosen from: hydrogen;
linear or branched alkyl containing from 1 to 6 carbon atoms;
cycloalkyl containing from 3 to 6 carbon atoms;
alkylcycloalkyl comprising an alkyl group containing from 1 to 6 carbon atoms and a cycloalkyl group containing from 3 to 6 carbon atoms;
aryl containing from 5 to 10 carbon atoms, optionally interrupted with a hetero atom chosen from nitrogen, oxygen and sulphur;
arylalkyl containing from 6 to 10 carbon atoms, optionally interrupted with a hetero atom chosen from nitrogen, oxygen and sulphur;
alkylaryl containing from 6 to 10 carbon atoms, optionally interrupted with a hetero atom chosen from nitrogen, oxygen and sulphur;
linear or branched alkenyl containing from 2 to 6 carbon atoms;
$R_B$ and $R_C$ possibly forming a ring containing from 5 to 7 atoms which may include one or more hetero atoms chosen from S, N or O;
Z is a halogen; and
n is an integer from 0 to 4 inclusive;
R2 is a linear or branched alkyl group containing from 1 to 4 carbon atoms;
$(CH_2)_nCF_3$, in which n is an integer from 0 to 4 inclusive;
methylcyclopropyl;
linear or branched alkenyl containing from 2 to 6 carbon atoms;
or a group $(CH_2)_mOR_B$ and $(CH_2)_mCO_2R_B$, in which m is an integer from 1 to 3 inclusive and $R_B$ is as described above;
R3 is a linear or branched alkyl group containing from 1 to 6 carbon atoms;
a cycloalkyle group containing from 3 to 6 carbon atoms;

an alkylcycloalkyl group comprising an alkyl group containing from 1 to 6 carbon atoms and a cycloalkyl group containing from 3 to 6 carbon atoms;

an aryl group containing from 5 to 10 carbon atoms, optionally interrupted with a hetero atom chosen from nitrogen, oxygen and sulphur;

an arylalkyl group containing from 6 to 10 carbon atoms, optionally interrupted with a hetero atom chosen from nitrogen, oxygen and sulphur;

an alkylaryl group containing from 6 to 10 carbon atoms, optionally interrupted with a hetero atom chosen from nitrogen, oxygen and sulphur;

an linear or branched alkenyl group containing from 2 to 6 carbon atoms;

the groups $(CH_2)_nOR_B$, $(CH_2)_nC(O)R_B$, $(CH_2)_nCOOR_B$, $(CH_2)_nOC(O)R_A$, $(CH_2)_nNR_BR_C$, $(CH_2)_nC(O)NR_BR_C$ and $(CH_2)_nNR_CC(O)R_B$, in which, $R_A$, $R_B$, $R_C$ and n are as defined above;

the aryl, arylalkyl and alkylaryl groups defined above being unsubstituted or substituted on the aryl group with 1, 2 or 3 groups chosen from:

halogen, hydroxyl, NO, $NO_2$, CN, alkoxy containing from 1 to 4 carbon atoms, $(CH_2)_nOR_B$, $(CH_2)_n NR_BR_C$ $(CH_2)_nNC(O)R_B$, $(CH_2)_nHNSO_2R_B$, $(CH_2)_n N(SO_2R_B)_2$, $CO_2R_B$, $CF_3$ and

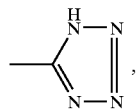

in which $R_B$, $R_C$ and n are as defined above; and,

X is O, S or NCN.

The invention relates particularly to the compounds of general formula II in which:

R1 is a linear or branched alkyl group containing from 1 to 6 carbon atoms;

a cycloalkyl group containing from 3 to 6 carbon atoms;

an alkylcycloalkyl group comprising an alkyl group containing from 1 to 6 carbon atoms and a cycloalkyl group containing from 3 to 6 carbon atoms;

an aryl group containing from 5 to 10 carbon atoms, optionally interrupted with a hetero atom chosen from nitrogen, oxygen and sulphur;

an alkylaryl group containing from 6 to 10 carbon atoms, optionally interrupted with a hetero atom chosen from nitrogen, oxygen and sulphur;

a linear or branched alkenyl group containing from 2 to 6 carbon atoms;

the groups $(CH_2)_nOR_B$, $(CH_2)_nC(O)R_B$, $(CH_2)_nCOOR_B$, $(CH_2)_nOC(O)R_A$, $(CH_2)_nNR_BR_C$, $(CH_2)_nC(O)NR_BR_C$, $(CH_2)_nNR_CC(O)R_B$ or $(CH_2)_nZ$, in which, $R_A$ is chosen from linear or branched alkyl containing from 1 to 6 carbon atoms;

aryl containing from 5 to 10 carbon atoms, optionally interrupted with a hetero atom chosen from nitrogen, oxygen and sulphur;

alkylaryl containing from 6 to 10 carbon atoms, optionally interrupted with a hetero atom chosen from nitrogen, oxygen and sulphur;

$R_B$ and $R_C$, which may be identical or different, are chosen from: hydrogen;

linear or branched alkyl containing, from 1 to 6 carbon atoms;

aryl containing from 5 to 10 carbon atoms, optionally interrupted with a hetero atom chosen from nitrogen, oxygen and sulphur;

alkylaryl containing from 6 to 10 carbon atoms, optionally interrupted with a hetero atom chosen from nitrogen, oxygen and sulphur;

n is an integer from 0 to 4 inclusive;

R2 is a linear or branched alkyl group containing from 1 to 4 carbon atoms or a group $(CH_2)_mOH$ or $(CH_2)_m CO_2H$, in which m is an integer from 1 to 3 inclusive;

R3 is a linear or branched alkyl group containing from 1 to 6 carbon atoms;

a cycloalkyl group containing from 3 to 6 carbon atoms;

an aryl group containing from 5 to 10 carbon atoms, optionally interrupted with a hetero atom chosen from nitrogen, oxygen and sulphur;

an arylalkyl group containing from 6 to 10 carbon atoms, optionally interrupted with a hetero atom chosen from nitrogen, oxygen and sulphur;

an alkylaryl group containing from 6 to 10 carbon atoms, optionally interrupted with a hetero atom chosen from nitrogen, oxygen and sulphur;

the aryl, arylalkyl and alkylaryl groups defined above being unsubstituted or substituted on the aryl group with 1, 2 or 3 groups chosen from:

halogen, hydroxyl, NO, $NO_2$, CN, alkoxy containing from 1 to 4 carbon atoms, $(CH_2)_nOR_B$, $(CH_2)_n NR_BR_C$ $(CH_2)_nNC(O)R_B$, $CO_2R_B$, $CF_3$ and

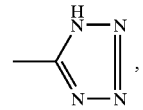

in which $R_B$, $R_C$ and n are as defined above; and

X is O, S or NCN.

The invention relates more particularly to the compounds of general formula II in which:

R1 is a linear or branched alkyl group containing from 1 to 4 carbon atoms;

a cycloalkyl group containing from 3 to 6 carbon atoms;

an alkylcycloalkyl group comprising an alkyl group containing from 1 to 3 carbon atoms and a cycloalkyl group containing from 3 to 6 carbon atoms;

R2 is a linear or branched alkyl group containing from 1 to 4 carbon atoms;

R3 is a linear or branched alkyl group containing from 1 to 4 carbon atoms;

an aryl group containing from 5 to 10 carbon atoms, optionally interrupted with a hetero atom chosen from nitrogen, oxygen and sulphur, preferably phenyl or pyridyl, the aryl groups being unsubstituted or substituted with 1, 2 or 3 groups, which may be identical or different, chosen from $NH_2$, halogen, methoxy, hydroxyl, CN, $CH_3$ and $CF_3$, and, X is O, S or NCN.

The invention also preferably relates to compounds of general formula II in which:

R1 is a linear or branched alkyl group containing from 1 to 4 carbon atoms;

R2 is a linear or branched alkyl group containing from 1 to 4 carbon atoms or a group $(CH_2)_nOH$, in which n is an integer from 1 to 4 inclusive;

R3 is a linear or branched alkyl group containing from 1 to 4 carbon atoms, a cycloalkyl group containing from 3 to 6 carbon atoms, an aryl group chosen from phenyl and thienyl, which may be unsubstituted or substituted with a group chosen from halogen, hydroxyl, methoxy, NH2 and CH$_3$; and X is S or O.

The invention also preferably relates to the compounds of general formula I in which:

R1 is a linear or branched alkyl group containing from 1 to 4 carbon atoms;

R2 is a linear or branched alkyl group containing from 1 to 4 carbon atoms or a group (CH$_2$)$_n$OH, in which n is an integer from 1 to 4 inclusive;

R3 is a linear or branched alkyl group containing from 1 to 4 carbon atoms, a cycloalkyl group containing from 3 to 6 carbon atoms, an aryl group chosen from phenyl and thienyl, which may be unsubstituted or substitued with a group chosen from halogen, hydroxyl, methoxy, NH$_2$, CH$_3$; and X is S.

Among the groups defined above, the following substituents are particularly preferred:

The linear or branched alkyl group contains from 1 to 6 carbon atoms and preferably from 1 to 4 carbon atoms. Examples of such groups are, inter alia, methyl, ethyl, n-propyl and isopropyl, tert-butyl, n-butyl, sec-butyl and isobutyl.

The linear or branched alkenyl group contains from 2 to 6 carbon atoms, preferably 2 to 4 carbon atoms. Examples comprise ethylidene, propylidene and butylidene.

The alkylcycloalkyl group comprises a linear or branched alkyl group containing from 1 to 6 carbon atoms, particularly from 1 to 4 carbon atoms, and a cycloalkyl group containing from 3 to 6 carbon atoms. Examples include methylcyclopropyl, methylcyclobutyl and methylcyclohexyl.

The cycloalkyl group comprises from 3 to 6 carbon atoms. Examples are cyclopropyl, cyclopentyl and cyclohexyl.

The aryl group is an aromatic group containing from 5 to 10 carbon atoms. Examples of such groups are phenyl, benzyl, tolyl and naphthyl. This aryl group can optionally be interrupted with a hetero atom chosen from nitrogen, oxygen and sulphur. The term "interrupted" means that the hetero atom can replace a carbon atom of the ring. Examples of such groups containing a hetero atom are, inter alia, thienyl and pyridyl.

The term alkylaryl corresponds to a group containing an alkyl grpup and an aryl group as defined above, linked to the rest of the molecule via the aryl group.

The term arylalkyl corresponds to a group containing an alkyl group and an aryl group as defined above, linked to the rest of the molecule via the alkyl group.

The aryl, alkylaryl and arylalkyl groups defined above can be unsubstituted or substituted on the aryl group with 1, 2 or 3 groups chosen from:

halogen, hydroxyl, NO, NO$_2$, alkoxy containing from 1 to 4 carbon atoms, (CH$_2$)$_n$NR$_B$R$_C$, (CH$_2$)$_n$NC(O)R$_B$, (CH$_2$)$_n$OR$_B$, (CH$_2$)$_n$HNSO$_2$R$_B$, CO$_2$R$_B$, CF$_3$ and

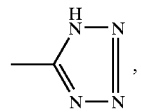

in which R$_B$, R$_C$ and n are as defined above.

Halogen comprises chlorine, bromine, fluorine and iodine.

The compounds listed below are among the preferred compounds of the present invention:

1-Ethyl-5-(4-methoxyphenyl)-3-methyl-6,7-dihydro-1H-pyrazolo[4,3-e][1,4]diazepin-8-one,
5-(4-Bromophenyl)-1-ethyl-3-methyl-6,7-dihydro-1H-pyrazolo[4,3-e][1,4]diazepin-8-one,
1,3-Dimethyl-5-phenyl-6,7-dihydro-1H-pyrazolo[4,3-e][1,4]diazepin-8-one,
5-(4-Methoxyphenyl)-1,3-dimethyl-6,7-dihydro-1H-pyrazolo[4,3-e][1,4]diazepin-8-one,
5-(4-Bromophenyl)-1,3-dimethyl-6,7-dihydro-1H-pyrazolo[4,3-e][1,4]diazepin-8-one,
1-Ethyl-3-methyl-5-naphth-2-yl-6,7-dihydro-1H-pyrazolo[4,3-e][1,4]diazepin-8-one,
5-(3-Chlorothien-2-yl)-1-ethyl-3-methyl-6,7-dihydro-1H-pyrazolo[4,3-e][1,4]diazepin-8-one,
Methyl 3-(1-ethyl-3-methyl-8-oxo-1,6,7,8-tetrahydropyrazolo[4,3-e][1,4]diazepin-5-yl)propanoate,
1-Ethyl-5-phenyl-6,7-dihydro-1H-pyrazolo[4,3-e][1,4]diazepin-8-one,
1-Ethyl-3-methyl-5-phenyl-6,7-dihydro-1H-pyrazolo[4,3-e][1,4]diazepin-8-one,
5-(4-Chlorophenyl)-1-ethyl-3-methyl-6,7-dihydro-1H-pyrazolo[4,3-e][1,4]diazepin-8-one,
5-(4-Aminophenyl)-1-ethyl-3-methyl-6,7-dihydro-1H-pyrazolo[4,3-e][1,4]diazepin-8-one,
1-Ethyl-5-(4-fluorophenyl)-3-methyl-6,7-dihydro-1H-pyrazolo[4,3-e][1,4]diazepin-8-one,
5-(3-Bromophenyl)-1-ethyl-3-methyl-6,7-dihydro-1H-pyrazolo[4,3-e][1,4]diazepin-8-one,
3-Methyl-5-phenyl-1-propyl-6,7-dihydro-1H-pyrazolo[4,3-e][1,4]diazepin-8-one,
1-Isopropyl-3-methyl-5-phenyl-6,7-dihydro-1H-pyrazolo[4,3-e][1,4]diazepin-8-one,
(±)1-Ethyl-3-methyl-5-phenyl-4,5,6,7-tetrahydro-1H-pyrazolo[4,3-e][1,4]diazepin-8-one,
1-(2-Hydroxyethyl)-3-methyl-5-phenyl-6,7-dihydro-1H-pyrazolo[4,3-e][1,4]diazepin-8-one,
1-Ethyl-3-methyl-5-phenyl-6,7-dihydro-1H-pyrazolo[4,3-e][1,4]diazepin-8-thione,
1-Ethyl-5-(4-methoxyphenyl)-6,7-dihydro-1H-pyrazolo[4,3-e][1,4]diazepin-8-one,
1-Ethyl-5-(3-methoxyphenyl)-3-methyl-6,7-dihydro-1H-pyrazolo[4,3-e][1,4]diazepin-8-one,
5-(2-Aminophenyl)-1-ethyl-3-methyl-6,7-dihydro-1H-pyrazolo[4,3-e][1,4]diazepin-8-one,
1-Ethyl-5-(2-methoxyphenyl)-3-methyl-6,7-dihydro-1H-pyrazolo[4,3-e][1,4]diazepin-8-one,
1-Ethyl-3-isopropyl-5-phenyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-one,
1-Ethyl-3-methyl-5-phenyl-4,5,6,7-tetrahydro-1H-pyrazolo[4,3-e][1,4]diazepin-8-one, isomer 1,
1-Ethyl-3-methyl-5-phenyl-4,5,6,7-tetrahydro-1H-pyrazolo[4,3-e][1,4]diazepin-8-one, isomer 2,
3-Methyl-5-phenyl-1-propyl-6,7-dihydro-1H-pyrazolo[4,3-e][1,4]diazepin-8-thione, 1-Ethyl-3-methyl-5-p-tolyl-6,7-dihydro-1H-pyrazolo[4,3-e][1,4]diazepin-8-one,
5-(3-Aminophenyl)-1-ethyl-3-methyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-thione,
1-Ethyl-3-isopropyl-5-phenyl-6,7-dihydro-1H-pyrazolo[4,3-e][1,4]diazepin-8-thione,
5-(4-Aminophenyl)-3-tert-butyl-1-ethyl-6,7-dihydro-1H-pyrazolo[4,3-e][1,4]diazepin-8-one,
5-(4-Aminophenyl)-1-ethyl-3-isopropyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-one,
5-(4-Aminophenyl)-3-methyl-1-propyl-6,7-dihydro-1H-pyrazolo[4,3-e][1,4]diazepin-8-one,
3-Methyl-5-phenyl-1-(2,2,2-trifluoroethyl)-6,7-dihydro-1H-pyrazolo[4,3-e][1,4]diazepin-8-one,
1,5-Diethyl-3-methyl-6,7-dihydro-1H-pyrazolo[4,3-e][1,4]diazepin-8-one,
5-Cyclohexyl-1-ethyl-3-methyl-6,7-dihydro-1H-pyrazolo[4,3-e][1,4]diazepin-8-one,
1-Ethyl-3-methyl-5-pyrid-4-yl-6,7-dihydro-1H-pyrazolo[4,3-e][1,4]diazepin-8-one,
(±)1-Ethyl-3-methyl-5-pyrid-4-yl-4,5,6,7-tetrahydro-1H-pyrazolo[4,3-e][1,4]diazepin-8-one,
5-tert-Butyl-1-ethyl-3-methyl-4,5,6,7-tetrahydro-1H-pyrazolo[4,3-e][1,4]diazepin-8-one,
5-(4-Diethylaminophenyl)-1-ethyl-3-methyl-1H-pyrazolo[4,3-e][1,4]diazepin-8-one,
3-Butyl-1-ethyl-5-phenyl-6,7-dihydro-1H-pyrazolo[4,3-e][1,4]diazepin-8-one,
N-[4-(1-Ethyl-3-methyl-8-oxo-1,6,7,8-tetrahydro-pyrazolo[4,3-e][1,4]diazepin-5-yl)phenyl]acetamide,
4-(1-Ethyl-3-methyl-8-oxo-1,6,7,8-tetrahydropyrazolo[4,3-e][1,4]diazepin-5-yl)benzonitrile,
5-tert-Butyl-1-ethyl-3-isopropyl-6,7-dihydro-1H-pyrazolo[4,3-e][1,4]diazepin-8-one,
1-Ethyl-3-isopropyl-5-p-tolyl-6,7-dihydro-1H-pyrazolo[4,3-e][1,4]diazepin-8-one,
4-(1-Ethyl-3-isopropyl-8-oxo-1,6,7,8-tetrahydro-pyrazolo[4,3-e][1,4]diazepin-5-yl)benzonitrile,
1-Ethyl-3-isopropyl-5-(4-pyrrolidin-1-yl-phenyl)-6,7-dihydro-1H-pyrazolo[4,3-e][1,4]diazepin-8-one,
5-(2,4-Dimethoxyphenyl)-1-ethyl-3-isopropyl-6,7-dihydro-1H-pyrazolo[4,3-e][1,4]diazepin-8-one,
5-tert-Butyl-3-isopropyl-1-propyl-6,7-dihydro-1H-pyrazolo[4,3-e][1,4]diazepin-8-one,
3-Isopropyl-1-propyl-5-p-tolyl-6,7-dihydro-1H-pyrazolo[4,3-e][1,4]diazepin-8-one,
4-(3-Isopropyl-8-oxo-1-propyl-1,6,7,8-tetrahydropyrazolo[4,3-e][1,4]diazepin-5-yl)benzonitrile,
3-Isopropyl-1-propyl-5-(4-pyrrolidin-1-yl-phenyl)-6,7-dihydro-1H-pyrazolo[4,3-e][1,4]diazepin-8-one,
5-(2,4-Dimethoxyphenyl)-3-isopropyl-1-propyl-6,7-dihydro-1H-pyrazolo[4,3-e][1,4]diazepin-8-one,
3,5-Di-tert-butyl-1-ethyl-6,7-dihydro-1H-pyrazolo[4,3-e][1,4]diazepin-8-one,
3-tert-Butyl-1-ethyl-5-p-tolyl-6,7-dihydro-1H-pyrazolo[4,3-e][1,4]diazepin-8-one,
4-(3-tert-Butyl-1-ethyl-8-oxo-1,6,7,8-tetrahydro-pyrazolo[4,3-e][1,4]diazepin-5-yl)benzonitrile,
3-tert-Butyl-1-ethyl-5-(4-pyrrolidin-1-yl-phenyl)-6,7-dihydro-1H-pyrazolo[4,3-e][1,4]diazepin-8-one,
3-tert-Butyl-5-(2,4-dimethoxyphenyl)-1-ethyl-6,7-dihydro-1H-pyrazolo[4,3-e][1,4]diazepin-8-one,
3,5-Di-tert-butyl-1-propyl-6,7-dihydro-1H-pyrazolo[4,3-e][1,4]diazepin-8-one,
3-tert-Butyl-1-propyl-5-p-tolyl-6,7-dihydro-1H-pyrazolo[4,3-e][1,4]diazepin-8-one,
4-(3-tert-Butyl-8-oxo-1-propyl-1,6,7,8-tetrahydropyrazolo[4,3-e][1,4]diazepin-5-yl)benzonitrile,
3-tert-Butyl-1-propyl-5-(4-pyrrolidin-1-yl-phenyl)-6,7-dihydro-1H-pyrazolo[4,3-e][1,4]diazepin-8-one,
3-tert-Butyl-5-(2,4-dimethoxyphenyl)-1-propyl-6,7-dihydro-1H-pyrazolo[4,3-e][1,4]diazepin-8-one,
3-Butyl-1-ethyl-5-phenyl-6,7-dihydro-1H-pyrazolo[4,3-e][1,4]diazepin-8-thione,
1-Ethyl-3-methyl-5-pyrid-3-yl-6,7-dihydro-1H-pyrazolo[4,3-e][1,4]diazepin-8-one,
1-Ethyl-3-methyl-5-pyrid-2-yl-6,7-dihydro-1H-pyrazolo[4,3-e][1,4]diazepin-8-one,
1-Ethyl-3-methyl-5-phenyl-1,6-dihydropyrazolo[4,3-e][1,4]diazepin-8-ylcyanamide,
N-[4-(1-Ethyl-3-methyl-8-oxo-1,6,7,8-tetrahydropyrazolo[4,3-e][1,4]diazepin-5-yl)phenyl]-(phenylsulphonyl)benzenesulphonamide,
(1-Ethyl-3-methyl-5-phenyl-1,6-dihydropyrazolo[4,3-e][1,4]diazepin-8-yl)methylamine,
1-Ethyl-3-isopropyl-5-phenyl-6,7-dihydro-1H-pyrazolo[4,3-e][1,4]diazepin-8-ylidenecyanamide,
3-tert-Butyl-1-ethyl-5-phenyl-6,7-dihydro-1H-pyrazolo[4,3-e][1,4]diazepin-8-ylidenecyanamide,
1-Cyclopentyl-3-methyl-5-phenyl-6,7-dihydro-1H-pyrazolo[4,3-e][1,4]diazepin-8-one,
1-Cyclopropylmethyl-3-methyl-5-phenyl-6,7-dihydro-1H-pyrazolo[4,3-e][1,4]diazepin-8-one,
1-Cyclobutylmethyl-3-methyl-5-phenyl-6,7-dihydro-1H-pyrazolo[4,3-e][1,4]diazepin-8-one,
1-Allyl-3-methyl-5-phenyl-6,7-dihydro-1H-pyrazolo[4,3-e][1,4]diazepin-8-one,
1-Ethyl-3-methyl-5-(4-trifluoromethylphenyl)-6,7-dihydro-1H-pyrazolo[4,3-e][1,4]diazepin-8-one,
1-Ethyl-3-isopropyl-5-(4-trifluoromethylphenyl)-6,7-dihydro-1H-pyrazolo[4,3-e][1,4]diazepin-8-one,
3-tert-Butyl-1-ethyl-5-(4-trifluoromethylphenyl)-6,7-dihydro-1H-pyrazolo[4,3-e][1,4]diazepin-8-one,
3-Isopropyl-1-propyl-5-p-tolyl-6,7-dihydro-1H-pyrazolo[4,3-e][1,4]diazepin-8-thione,
3,5-Di-tert-butyl-1-propyl-6,7-dihydro-1H-pyrazolo[4,3-e][1,4]diazepin-8-thione,
5-tert-Butyl-3-isopropyl-1-propyl-6,7-dihydro-1H-pyrazolo[4,3-e][1,4]diazepin-8-thione,
1-Ethyl-3-isopropyl-5-p-tolyl-6,7-dihydro-1H-pyrazolo[4,3-e][1,4]diazepin-8-thione,
5-tert-Butyl-1-ethyl-3-isopropyl-6,7-dihydro-1H-pyrazolo[4,3-e][1,4]diazepin-8-thione,
(±)3-sec-Butyl-1-ethyl-5-phenyl-6,7-dihydro-1H-pyrazolo[4,3-e][1,4]diazepin-8-one,
(±)3-sec-Butyl-1-ethyl-5-pyrid-4-yl-6,7-dihydro-1H-pyrazolo[4,3-e][1,4]diazepin-8-one,
(±)3-sec-Butyl-5-phenyl-1-propyl-4-yl-6,7-dihydro-1H-pyrazolo[4,3-e][1,4]diazepin-8-one,
(±)3-sec-Butyl-1-propyl-5-pyrid-4-yl-6,7-dihydro-1H-pyrazolo[4,3-e][1,4]diazepin-8-one,
3-Cyclohexyl-1-ethyl-5-phenyl-4-yl-6,7-dihydro-1H-pyrazolo[4,3-e][1,4]diazepin-8-one,
3-Cyclohexyl-1-ethyl-5-pyrid-4-yl-6,7-dihydro-1H-pyrazolo[4,3-e][1,4]diazepin-8-one,
3-Cyclohexyl-5-phenyl-1-propyl-4-yl-6,7-dihydro-1H-pyrazolo[4,3-e][1,4]diazepin-8-one,
3-Cyclohexyl-1-propyl-5-pyrid-4-yl-6,7-dihydro-1H-pyrazolo[4,3-e][1,4]diazepin-8-one,
3-Cyclohexylmethyl-1-ethyl-5-pyrid-4-yl-6,7-dihydro-1H-pyrazolo[4,3-e][1,4]diazepin-8-one, 3-Cyclohexylmethyl-5-phenyl-1-propyl-6,7-dihydro-1H-pyrazolo[4,3-e][1,4]diazepin-8-one,
3-Cyclohexylmethyl-1-propyl-5-pyrid-4-yl-6,7-dihydro-1H-pyrazolo[4,3-e][1,4]diazepin-8-one,
3-Cyclohexylmethyl-1-ethyl-5-phenyl-6,7-dihydro-1H-pyrazolo[4,3-e][1,4]diazepin-8-one,
1-Ethyl-8-oxo-5-phenyl-1,6,7,8-tetrahydropyrazolo[4,3-e][1,4]diazepin-3-carboxylic acid ethyl ester,
5-tert-Butyl-1-ethyl-3-isopropyl-6,7-dihydro-1H-pyrazolo[4,3-e][1,4]diazepin-8-ylidenecyanamide,
1-Ethyl-3-isopropyl-5-p-tolyl-6,7-dihydro-1-pyrazolo[4,3-e][1,4]diazepin-8-ylidenecyanamide,
1-Ethyl-3-isopropyl-5-(4-methoxyphenyl)-6,7-dihydro-1H-pyrazolo[4,3-e][1,4]diazepin-8-one,
1-Ethyl-5-(4-methoxyphenyl)-3-methyl-6,7-dihydro-1H-pyrazolo[4,3-e][1,4]diazepin-8-thione,
1-Ethyl-5-(4-methoxyphenyl)-3-methyl-6,7-dihydro-1H-pyrazolo[4,3-e][1,4]diazepin-8-ylidenecyanamide,
3-Isopropyl-5-(4-methoxyphenyl)-1-propyl-6,7-dihydro-1H-pyrazolo[4,3e][1,4]diazepin-8-one,
3-tert-Butyl-1-ethyl-5-(4-methoxyphenyl)-6,7-dihydro-1H-pyrazolo[4,3-e][1,4]diazepin-8-one,
3-tert-Butyl-5-(4-methoxyphenyl)-1-propyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-ylidenecyanamide,
(±)3-sec-Butyl-1-ethyl-5-(4-methoxyphenyl)-6,7-dihydro-1H-pyrazolo[4,3-e][1,4]diazepin-8-one,
(±)3-sec-Butyl-5-(4-methoxyphenyl)-1-propyl-6,7-dihydro-1H-pyrazolo[4,3-e][1,4]diazepin-8-one,
1-Ethyl-3-methyl-5-(3,4,5-trimethoxyphenyl)-6,7-dihydro-1H-pyrazolo[4,3-e][1,4]diazepin-8-one,
1-Ethyl-5-(3-hydroxyphenyl)-3-methyl-6,7-dihydro-1H-pyrazolo[4,3-e][1,4]diazepin-8-one,
1-Ethyl-5-(2-hydroxyphenyl)-3-methyl-6,7-dihydro-1H-pyrazolo[4,3-e][1,4]diazepin-8-one,
1-Ethyl-3-methyl-5-(2,3,4-trimethoxyphenyl)-6,7-dihydro-1H-pyrazolo[4,3-e][1,4]diazepin-8-one,
1-Ethyl-3,5-diphenyl-6,7-dihydro-1H-pyrazolo[4,3-e][1,4]diazepin-8-one,
1-Ethyl-5-(4-hydroxyphenyl)-3-isopropyl-6,7-dihydro-1H-pyrazolo[4,3-e][1,4]diazepin-8-one,
5-(4-Hydroxyphenyl)-3-isopropyl-1-propyl-6,7-dihydro-1H-pyrazolo[4,3-e][1,4]diazepin-8-one,
3-tert-Butyl-1-ethyl-5-(4-hydroxyphenyl)-6,7-dihydro-1H-pyrazolo[4,3-e][1,4]diazepin-8-one,
5-(2,6-Dimethoxyphenyl)-1-ethyl-3-methyl-6,7-dihydro-1H-pyrazolo[4,3-e][1,4]diazepin-8-one,
3-Ethoxymethyl-1-ethyl-5-phenyl-6,7-dihydro-1H-pyrazolo[4,3-e][1,4]diazepin-8-one Among the preferred compounds defined above, the following compounds are preferred:
1-Ethyl-5-(4-methoxyphenyl)-3-methyl-6,7-dihydro-1H-pyrazolo[4,3-e][1,4]diazepin-8-one,
5-(4-Bromophenyl)-1-ethyl-3-methyl-6,7-dihydro-1H-pyrazolo[4,3-e][1,4]diazepin-8-one,
1-Ethyl-3-methyl-5-naphth-2-yl-6,7-dihydro-1H-pyrazolo[4,3-e][1,4]diazepin-8-one,
5-(3-Chlorothien-2-yl)-1-ethyl-3-methyl-6,7-dihydro-1H-pyrazolo[4,3-e][1,4]diazepin-8-one,
Methyl 3-(1-ethyl-3-methyl-8-oxo-1,6,7,8-tetrahydropyrazolo[4,3-e][1,4]diazepin-5-yl)propanoate,
5-(4-Chlorophenyl)-1-ethyl-3-methyl-6,7-dihydro-1H-pyrazolo[4,3-e][1,4]diazepin-8-one,
5-(4-Aminophenyl)-1-ethyl-3-methyl-6,7-dihydro-1H-pyrazolo[4,3-e][1,4]diazepin-8-one,
1-Ethyl-5-(4-fluorophenyl)-3-methyl-6,7-dihydro-1H-pyrazolo[4,3-e][1,4]diazepin-8-one,
5-(3-Bromophenyl)-1-ethyl-3-methyl-6,7-dihydro-1H-pyrazolo[4,3-e][1,4]diazepin-8-one,
3-Methyl-5-phenyl-1-propyl-6,7-dihydro-1H-pyrazolo[4,3-e][1,4]diazepin-8-one,
1-(2-Hydroxyethyl)-3-methyl-5-phenyl-6,7-dihydro-1H-pyrazolo[4,3-e][1,4]diazepin-8-one,
1-Ethyl-3-methyl-5-phenyl-6,7-dihydro-1H-pyrazolo[4,3-e][1,4]diazepin-8-thione,
1-Ethyl-5-(3-methoxyphenyl)-3-methyl-6,7-dihydro-1H-pyrazolo[4,3-e][1,4]diazepin-8-one,
5-(2-Aminophenyl)-1-ethyl-3-methyl-6,7-dihydro-1H-pyrazolo[4,3-e][1,4]diazepin-8-one,
1-Ethyl-5-(2-methoxyphenyl)-3-methyl-6,7-dihydro-1H-yrazolo[4,3-e][1,4]diazepin-8-one,
1-Ethyl-3-isopropyl-5-phenyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-one,
1-Ethyl-3-methyl-5-p-tolyl-6,7-dihydro-1H-pyrazolo[4,3-e][1,4]diazepin-8-one,
5-(3-Aminophenyl)-1-ethyl-3-methyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-thione,
1-Ethyl-3-isopropyl-5-phenyl-6,7-dihydro-1H-pyrazolo[4,3-e][1,4]diazepin-8-thione,
5-(4-Aminophenyl)-3-tert-butyl-1-ethyl-6,7-dihydro-1H-pyrazolo[4,3-e][1,4]diazepin-8-one,
5-(4-Aminophenyl)-1-ethyl-3-isopropyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-one,
5-(4-Aminophenyl)-3-methyl-1-propyl-6,7-dihydro-1H-pyrazolo[4,3-e][1,4]diazepin-8-one,
3-Methyl-5-phenyl-1-(2,2,2-trifluoroethyl)-6,7-dihydro-1H-pyrazolo[4,3-e][1,4]diazepin-8-one,
5-Cyclohexyl-1-ethyl-3-methyl-6,7-dihydro-1H-pyrazolo[4,3-e][1,4]diazepin-8-one,
1-Ethyl-3-methyl-5-pyrid-4-yl-6,7-dihydro-1H-pyrazolo[4,3-e][1,4]diazepin-8-one,
5-tert-Butyl-1-ethyl-3-methyl-4,5,6,7-tetrahydro-1H-pyrazolo[4,3-e][1,4]diazepin-8-one,
3-Butyl-1-ethyl-5-phenyl-6,7-dihydro-1H-pyrazolo[4,3-e][1,4]diazepin-8-one,
5-tert-Butyl-1-ethyl-3-isopropyl-1H-pyrazolo[4,3-e][1,4]diazepin-8-one,
1-Ethyl-3-isopropyl-5-p-tolyl-6,7-dihydro-1H-pyrazolo[4,3-e][1,4]diazepin-8-one,
4-(1-Ethyl-3-isopropyl-8-oxo-1,6,7,8-tetrahydro-pyrazolo[4,3-e][1,4]diazepin-5-yl)benzonitrile,
5-(2,4-Dimethoxyphenyl)-1-ethyl-3-isopropyl-6,7-dihydro-1H-pyrazolo[4,3-e][1,4]diazepin-8-one,
5-tert-Butyl-3-isopropyl-1-propyl-6,7-dihydro-1H-pyrazolo[4,3-e][1,4]diazepin-8-one,
3-Isopropyl-1-propyl-5-p-tolyl-6,7-dihydro-1H-pyrazolo[4,3-e][1,4]diazepin-8-one,
4-(3-Isopropyl-8-oxo-1-propyl-1,6,7,8-tetrahydropyrazolo[4,3-e][1,4]diazepin-5-yl)benzonitrile,
5-(2,4-Dimethoxyphenyl)-3-isopropyl-1-propyl-6,7-dihydro-1H-pyrazolo[4,3-e][1,4]diazepin-8-one,
3,5-Di-tert-butyl-1-ethyl-6,7-dihydro-1H-pyrazolo[4,3-e][1,4]diazepin-8-one,
3-tert-Butyl-1-ethyl-5-p-tolyl-6,7-dihydro-1H-pyrazolo[4,3-e][1,4]diazepin-8-one,
4-(3-tert-1ethyl-8-oxo-1,6,7,8-tetrahydro-pyrazolo[4,3-e][1,4]diazepin-5-yl)benzonitrile,
3-tert-Butyl-5-(2,4-dimethoxyphenyl)-1-ethyl-6,7-dihydro-1H-pyrazolo[4,3-e][1,4]diazepin-8-one, 3,5-Di-tert-butyl-1-propyl-6,7-dihydro-1H-pyrazolo[4,3-e]
[1,4]diazepin-8-one,
3-tert-Butyl-1-propyl-5-p-tolyl-6,7-dihydro-1H-pyrazolo[4,
3-e][1,4]diazepin-8-one,
4-(3-tert-Butyl-8-oxo-1-propyl-1,6,7,8-tetrahydro-pyrazolo
[4,3-e][1,4]diazepin-5-yl)benzonitrile,
3-tert-Butyl-5-(2,4-dimethoxyphenyl)-1-propyl-6,7-
dihydro-1H-pyrazolo[4,3-e][1,4]diazepin-8-one,
3-Butyl-1-ethyl-5-phenyl-6,7-dihydro-1H-pyrazolo[4,3-e]
[1,4]diazepin-8-thione,
1-Ethyl-3-methyl-5-pyrid-3-yl-6,7-dihydro-1H-pyrazolo[4,
3-e][1,4]diazepin-8-one,
1-Ethyl-3-methyl-5-pyrid-2-yl-6,7-dihydro-1H-pyrazolo[4,
3-e][1,4]diazepin-8-one,
1-Ethyl-3-methyl-5-phenyl-1,6-dihydropyrazolo[4,3-e][1,4]
diazepin-8-ylcyanamide,
N-[4-(1-Ethyl-3-methyl-8-oxo-1,6,7,8-tetrahydro-pyrazolo
[4,3-e][1,4]diazepin-5-yl)phenyl]-(phenylsulphonyl)
benzenesulphonamide,
1-Ethyl-3-isopropyl-5-phenyl-6,7-dihydro-1H-pyrazolo[4,
3-e][1,4]diazepin-8-ylidenecyanamide,
3-tert-Butyl-1-ethyl-5-phenyl-6,7-dihydro-1H-pyrazolo[4,
3-e][1,4]diazepin-8-ylidenecyanamide,
1-Cyclopropylmethyl-3-methyl-5-phenyl-6,7-dihydro-1H-
pyrazolo[4,3-e][1,4]diazepin-8-one,
1-Allyl-3-methyl-5-phenyl-6,7-dihydro-1H-pyrazolo[4,3-e]
[1,4]diazepin-8-one,
1-Ethyl-3-methyl-5-(4-trifluoromethylphenyl)-6,7-dihydro-
1H-pyrazolo[4,3-e][1,4]diazepin-8-one,
1-Ethyl-3-isopropyl-5-(4-trifluoromethylphenyl)-6,7-
dihydro-1H-pyrazolo[4,3-e][1,4]diazepin-8-one,
3-tert-Butyl-1-ethyl-5-(4-trifluoromethylphenyl)-6,7-
dihydro-1H-pyrazolo[4,3-e][1,4]diazepin-8-one,
3-Isopropyl-1-propyl-5-p-tolyl-6,7-dihydro-1H-pyrazolo[4,
3-e][1,4]diazepin-8-thione,
3,5-Di-tert-butyl-1-propyl-6,7-dihydro-1H-pyrazolo[4,3-e]
[1,4]diazepin-8-thione,
5-tert-Butyl-3-isopropyl-1-propyl-6,7-dihydro-1H-pyrazolo
[4,3-e][1,4]diazepin-8-thione,
1-Ethyl-3-isopropyl-5-p-tolyl-6,7-dihydro-1H-pyrazolo[4,
3-e][1,4]diazepin-8-thione,
5-tert-Butyl-1-ethyl-3-isopropyl-6,7-dihydro-1H-pyrazolo
[4,3-e][1,4]diazepin-8-thione,
(±)3-sec-Butyl-1-ethyl-5-phenyl-6,7-dihydro-1H-pyrazolo
[4,3-e][1,4]diazepin-8-one,
(±)3-sec-Butyl-1-ethyl-5-pyrid-4-yl-6,7-dihydro-1H-
pyrazolo[4,3-e][1,4]diazepin-8-one,
(±)3-sec-Butyl-5-phenyl-1-propyl-4-yl-6,7-dihydro-1H-
pyrazolo[4,3-e][1,4]diazepin-8-one,
(±)3-sec-Butyl-1-propyl-5-pyrid-4-yl-6,7-dihydro-1H-
pyrazolo[4,3-e][1,4]diazepin-8-one,
3-Cyclohexyl-1-ethyl-5-phenyl-4-yl-6,7-dihydro-1H-
pyrazolo[4,3-e][1,4]diazepin-8-one,
3-Cyclohexyl-1-ethyl-5-pyrid-4-yl-6,7-dihydro-1H-
pyrazolo[4,3-e][1,4]diazepin-8-one,
3-Cyclohexyl-5-phenyl-1-propyl-4-yl-6,7-dihydro-1H-
pyrazolo[4,3-e][1,4]diazepin-8-one,
3-Cyclohexyl-1-propyl-5-pyrid-4-yl-6,7-dihydro-1H-
pyrazolo[4,3-e][1,4]diazepin-8-one,
3-Cyclohexylmethyl-1-ethyl-5-pyrid-4-yl-6,7-dihydro-1H-
pyrazolo[4,3-e][1,4]diazepin-8-one,
3-Cyclohexylmethyl-5-phenyl-1-propyl-6,7-dihydro-1H-
pyrazolo[4,3-e][1,4]diazepin-8-one,
3-Cyclohexylmethyl-1-propyl-5-pyrid-4-yl-6,7-dihydro-
1H-pyrazolo[4,3-e][1,4]diazepin-8-one,
3-Cyclohexylmethyl-1-ethyl-5-phenyl-6,7-dihydro-1H-
pyrazolo[4,3-e][1,4]diazepin-8-one,
1-Ethyl-8-oxo-5-phenyl-1,6,7,8-tetrahydropyrazolo[4,3-e]
[1,4]diazepin-3-carboxylic acid ethyl ester,
5-tert-Butyl-1-ethyl-3-isopropyl-6,7-dihydro-1H-pyrazolo
[4,3-e][1,4]diazepin-8-ylidenecyanamide,
1-Ethyl-3-isopropyl-5-p-tolyl-6,7-dihydro-1H-pyrazolo[4,
3-e][1,4]diazepin-8-ylidenecyanamide,
1-Ethyl-3-isopropyl-5-(4-methoxyphenyl)-6,7-dihydro-1H-
pyrazolo[4,3-e][1,4]diazepin-8-one,
1-Ethyl-5-(4-methoxyphenyl)-3-methyl-6,7-dihydro-1H-
pyrazolo[4,3-e][1,4]diazepin-8-thione,
1-Ethyl-5-(4-methoxyphenyl)-3-methyl-6,7-dihydro-1H-
pyrazolo[4,3-e][1,4]diazepin-8-ylidenecyanamide,
3-Isopropyl-5-(4-methoxyphenyl)-1-propyl-6,7-dihydro-
1H-pyrazolo[4,3-e][1,4]diazepin-8-one,
3-tert-Butyl-1-ethyl-5-(4-methoxyphenyl)-6,7-dihydro-1H-
pyrazolo[4,3-e][1,4]diazepin-8-one,
3-tert-Butyl-5-(4-methoxyphenyl)-1-propyl-6,7-dihydro-
1H-pyrazolo[4,3-e][1,4]diazepin-8-one,
1-Ethyl-5-(4-hydroxyphenyl)-3-methyl-6,7-dihydro-1H-
pyrazolo[4,3-e][1,4]diazepin-8-ylidenecyanamide,
(±)3-sec-Butyl-1-ethyl-5-(4-methoxyphenyl)-6,7-dihydro-
1H-pyrazolo[4,3-e][1,4]diazepin-8-one,
(±)3-sec-Butyl-5-(4-methoxyphenyl)-1-propyl-6,7-dihydro-
1H-pyrazolo[4,3-e][1,4]diazepin-8-one,
1-Ethyl-3-methyl-5-(3,4,5-trimethoxyphenyl)-6,7-dihydro-
1H-pyrazolo[4,3-e][1,4]diazepin-8-one,
1-Ethyl-5-(3-hydroxyphenyl)-3-methyl-6,7-dihydro-1H-
pyrazolo[4,3-e][1,4]diazepin-8-one,
1-Ethyl-5-(2-hydroxyphenyl)-3-methyl-6,7-dihydro-1H-
pyrazolo[4,3-e][1,4]diazepin-8-one,
1-Ethyl-3,5-diphenyl-6,7-dihydro-1H-pyrazolo[4,3-e][1,4]
diazepin-8-one,
1-Ethyl-5-(4-hydroxyphenyl)-3-isopropyl-6,7-dihydro-1H-
pyrazolo[4,3-e][1,4]diazepin-8-one,
5-(4-Hydroxyphenyl)-3-isopropyl-1-propyl-6,7-dihydro-
1H-pyrazolo[4,3-e][1,4)diazepin-8-one,
3-tert-Butyl-1-ethyl-5-(4-hydroxyphenyl)-6,7-dihydro-1H-
pyrazolo[4,3-e][1,4]diazepin-8-one,
3-Ethoxymethyl-1-ethyl-5-phenyl-6,7-dihydro-1H-pyrazolo
[4,3-e][1,4]diazepin-8-one.
Among the preferred compounds defined above, the following compounds are preferred:
1-Ethyl-3-methyl-5-phenyl-6,7-dihydro-1H-pyrazolo[4,3-e]
[1,4]diazepin-8-thione,
1-Ethyl-5-(2-methoxyphenyl)-3-methyl-6,7-dihydro-1H-
yrazolo[4,3-e][1,4]diazepin-8-one,
1-Ethyl-3-isopropyl-5-phenyl-6,7-dihydro-1H-pyrazolo[4,
3-e][1,4]diazepin-8-one,
3-tert-Butyl-1-ethyl-5-phenyl-6,7-dihydro-1H-pyrazolo[4,
3-e][1,4]diazepin-8-one,
3-tert-Butyl-1-ethyl-5-phenyl-6,7-dihydro-1H-pyrazolo[4,
3-e][1,4]diazepin-8-thione,
1-Ethyl-3-isopropyl-5-phenyl-6,7-dihydro-1H-pyrazolo[4,
3-e][1,4]diazepin-8-thione,
5-(4-Aminophenyl)-3-tert-butyl-1-ethyl-6,7-dihydro-1H-
pyrazolo[4,3-e][1,4]diazepin-8-one,
5-(4-Aminophenyl)-1-ethyl-3-isopropyl-6,7-dihydro-1H-
pyrazolo[4,3-e][1,4]diazepin-8-one,
1-Ethyl-5-(4-hydroxyphenyl)-3-methyl-6,7-dihydro-1H-
pyrazolo[4,3-e][1,4]diazepin-8-one,
5-Cyclohexyl-1-ethyl-3-methyl-6,7-dihydro-1H-pyrazolo
[4,3-e][1,4]diazepin-8-one,
1-Ethyl-3-methyl-5-pyrid-4-yl-6,7-dihydro-1H-pyrazolo[4,
3-e][1,4]diazepin-8-one,
5-tert-Butyl-1-ethyl-3-methyl-4,5,6,7-tetrahydro-1H-
pyrazolo[4,3-e][1,4]diazepin-8-one,
3-Butyl-1-ethyl-5-phenyl-6,7-dihydro-1H-pyrazolo[4,3-e]
[1,4]diazepin-8-one, 5-tert-Butyl-1-ethyl-3-isopropyl-6,7-dihydro-1H-pyrazolo[4,3-e][1,4]diazepin-8-one,
1-Ethyl-3-isopropyl-5-p-tolyl-6,7-dihydro-1H-pyrazolo[4,3-e][1,4]diazepin-8-one,
4-(1-Ethyl-3-isopropyl-8-oxo-1,6,7,8-tetrahydro-pyrazolo[4,3-e][1,4]diazepin-5-yl)benzonitrile,
5-(2,4-Dimethoxyphenyl)-1-ethyl-3-isopropyl-6,7-dihydro-1H-pyrazolo[4,3-e][1,4]diazepin-8-one,
5-tert-Butyl-3-isopropyl-1-propyl-6,7-dihydro-1H-pyrazolo[4,3-e][1,4]diazepin-8-one,
3-Isopropyl-1-propyl-5-p-tolyl-6,7-dihydro-1H-pyrazolo[4,3-e][1,4]diazepin-8-one,
4-(3-Isopropyl-8-oxo-1-propyl-1,6,7,8-tetrahydropyrazolo[4,3-e][1,4]diazepin-5-yl)benzonitrile,
5-(2,4-Dimethoxyphenyl)-3-isopropyl-1-propyl-6,7-dihydro-1H-pyrazolo[4,3-e][1,4]diazepin-8-one,
3,5-Di-tert-butyl-1-ethyl-6,7-dihydro-1H-pyrazolo[4,3-e][1,4]diazepin-8-one,
3-tert-Butyl-1-ethyl-5-p-tolyl-6,7-dihydro-1H-pyrazolo(4,3-e][1,4]diazepin-8-one,
4-(3-tert-Butyl-1-ethyl-8-oxo-1,6,7,8-tetrahydropyrazolo[4,3-e][1,4]diazepin-5-yl)benzonitrile,
3-Butyl-1-ethyl-5-phenyl-6,7-dihydro-1H-pyrazolo[4,3-e][1,4]diazepin-8-thione,
1-Ethyl-3-methyl-5-phenyl-1,6-dihydropyrazolo[4,3-e][1,4]diazepin-8-ylcyanamide,
1-Ethyl-3-isopropyl-5-phenyl-6,7-dihydro-1H-pyrazolo[4,3-e][1,4]diazepin-8-ylidenecyanamide,
3-tert-Butyl-1-ethyl-5-phenyl-6,7-dihydro-1H-pyrazolo[4,3-e][1,4]diazepin-8-ylidenecyanamide,
1-Ethyl-3-isopropyl-5-p-tolyl-6,7-dihydro-1H-pyrazolo[4,3-e][1,4]diazepin-8-thione,
(±)3-sec-Butyl-1-ethyl-5-phenyl-6,7-dihydro-1H-pyrazolo[4,3-e][1,4]diazepin-8-one,
(±)3-sec-Butyl-1-ethyl-5-pyrid-4-yl-6,7-dihydro-1H-pyrazolo[4,3-e][1,4]diazepin-8-one,
(±)3-sec-Butyl-1-propyl-5-pyrid-4-yl-6,7-dihydro-1H-pyrazolo[4,3-e][1,4]diazepin-8-one,
3-Cyclohexyl-1-ethyl-5-pyrid-4-yl-6,7-dihydro-1H-pyrazolo[4,3-e][1,4]diazepin-8-one,
3-Cyclohexyl-1-propyl-5-pyrid-4-yl-6,7-dihydro-1H-pyrazolo[4,3-e][1,4]diazepin-8-one,
3-Cyclohexylmethyl-1-ethyl-5-pyrid-4-yl-6,7-dihydro-1H-pyrazolo[4,3-e][1,4]diazepin-8-one,
5-tert-Butyl-1-ethyl-3-isopropyl-6,7-dihydro-1H-pyrazolo[4,3-e][1,4]diazepin-8-ylidenecyanamide,
1-Ethyl-3-isopropyl-5-p-tolyl-6,7-dihydro-1H-pyrazol[4,3-e][1,4]diazepin-8-ylidenecyanamide,
1-Ethyl-3-isopropyl-5-(4-methoxyphenyl)-6,7-dihydro-1H-pyrazolo[4,3-e][1,4]diazepin-8-one,
1-Ethyl-5-(4-methoxyphenyl)-3-methyl-6,7-dihydro-1-pyrazolo[4,3-e][1,4]diazepin-8-ylidenecyanamide,
3-Isopropyl-5-(4-methoxyphenyl)-1-propyl-6,7-dihydro-1H-pyrazolo[4,3-e][1,4]diazepin-8-one,
3-tert-Butyl-5-(4-methoxyphenyl)-1-propyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-ylidenecyanamide,
(±)3-sec-Butyl-1-ethyl-5-(4-methoxyphenyl)-6,7-dihydro-1H-pyrazolo[4,3-e][1,4]diazepin-8-one,
1-Ethyl-3-methyl-5-(3,4,5-trimethoxyphenyl)-6,7-dihydro-1H-pyrazolo[4,3-e][1,4]diazepin-8-one,
1-Ethyl-5-(3-hydroxyphenyl)-3-methyl-6,7-dihydro-1H-pyrazolo[4,3-e][1,4]diazepin-8-one,
1-Ethyl-5-(2-hydroxyphenyl)-3-methyl-6,7-dihydro-1H-pyrazolo[4,3-e][1,4]diazepin-8-one,
1-Ethyl-3,5-diphenyl-6,7-dihydro-1H-pyrazolo[4,3-e][1,4]diazepin-8-one,
1-Ethyl-5-(4-hydroxyphenyl)-3-isopropyl-6,7-dihydro-1H-pyrazolo[4,3-e][1,4]diazepin-8-one,
5-(4-Hydroxyphenyl)-3-isopropyl-1-propyl-6,7-dihydro-1H-pyrazolo[4,3-e][1,4]diazepin-8-one,
3-tert-Butyl-1-ethyl-5-(4-hydroxyphenyl)-6,7-dihydro-1H-pyrazolo[4,3-e][1,4]diazepin-8-one,
3-Ethoxymethyl-1-ethyl-5-phenyl-6,7-dihydro-1H-pyrazolo[4,3-e][1,4]diazepin-8-one.

Among the preferred compounds defined above, the following compounds are preferred:
1-Ethyl-3-methyl-5-phenyl-6,7-dihydro-1H-pyrazolo[4,3-e][1,4]diazepin-8-thione,
1-Ethyl-3-isopropyl-5-phenyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-thione,
1-Ethyl-3-isopropyl-5-phenyl-6,7-dihydro-1H-pyrazolo[4,3-e][1,4]diazepin-8-thione,
5-9(4-Aminophenyl)-3-tert-butyl-1-ethyl-6,7-dihydro-1H-pyrazolo[4,3-e][1,4]diazepin-8-one,
5-(4-Aminophenyl)-1-ethyl-3-isopropyl-6,7-dihydro-1H-pyrazolo[4,3-e][1,4]diazepin-8-one,
3-Butyl-1-ethyl-5-phenyl-6,7-dihydro-1H-pyrazolo [4,3-e][1,4]diazepin-8-one,
5-tert-Butyl-1-ethyl-3-isopropyl-6,7-dihydro-1H-pyrazolo[4,3-e][1,4]diazepin-8-one,
1-Ethyl-3-isopropyl-5-p-tolyl-6,7-dihydro-1H-pyrazolo[4,3-e][1,4]diazepin-8-one,
4-(1-Ethyl-3-isopropyl-8-oxo-1,6,7,8-tetrahydropyrazolo[4,3-e][1,4]diazepin-5-yl)benzonitrile,
5-tert-Butyl-3-isopropyl-1-propyl-6,7-dihydro-1H-pyrazolo[4,3-e][1,4]diazepin-8-one,
4-(3-Isopropyl-8-oxo-1-propyl-1,6,7,8-tetrahydropyrazolo[4,3-e][1,4]diazepin-5-yl)benzonitrile,
3,5-Di-tert-butyl-1-ethyl-6,7-dihydro-1H-pyrazolo[4,3-e][1,4]diazepin-8-one,
3-tert-Butyl-1-ethyl-5-p-tolyl-6,7-dihydro-1H-pyrazolo[4,3-e][1,4]diazepin-8-one,
4-(3-tert-Butyl-1-ethyl-8-oxo-1,6,7,8-tetrahydropyrazolo[4,3-e][1,4]diazepin-5-yl)benzonitrile,
3-Butyl-1-ethyl-5-phenyl-6,7-dihydro-1H-pyrazolo [4,3-e][1,4]diazepin-8-thione,
1-Ethyl-3-methyl-5-phenyl-1,6-dihydropyrazolo[4,3-e][1,4]diazepin-8-ylcyanamide,
1-Ethyl-3-isopropyl-5-phenyl-6,7-dihydro-1H-pyrazolo[4,3-e][1,4]diazepin-8-ylidenecyanamide,
3-tert-Butyl-1-ethyl-5-phenyl-6,7-dihydro-1H-pyrazolo[4,3-e][1,4]diazepin-8-ylidenecyanamide,
1-Ethyl-3-isopropyl-5-p-tolyl-6,7-dihydro-1H-pyrazolo[4,3-e][1,4]diazepin-8-thione,
(±)3-sec-Butyl-1-ethyl-5-phenyl-6,7-dihydro-1H-pyrazolo[4,3-e][1,4]diazepin-8-one,
(±)3-sec-Butyl-1-ethyl-5-pyrid-4-yl-6,7-dihydro-1H-pyrazolo[4,3-e][1,4]diazepin-8-one,
(±)3-sec-Butyl-1-propyl-5-pyrid-4-yl-6,7-dihydro-1H-pyrazolo[4,3-e][1,4]diazepin-8-one,
3-Cyclohexyl-1-ethyl-5-pyrid-4-yl-6,7-dihydro-1H-pyrazolo[4,3-e][1,4]diazepin-8-one,
3-Cyclohexyl-1-propyl-5-pyrid-4-yl-6,7-dihydro-1H-pyrazolo[4,3-e][1,4]diazepin-8-one,
3-Cyclohexylmethyl-1-ethyl-5-pyrid-4-yl-6,7-dihydro-1H-pyrazolo[4,3-e][1,4]diazepin-8-one,
5-tert-Butyl-1-ethyl-3-isopropyl-6,7-dihydro-1H-pyrazolo[4,3-e][1,4]diazepin-8-ylidenecyanamide,
1-Ethyl-3-isopropyl-5-p-tolyl-6,7-dihydro-1H-pyrazolo[4,3-e][1,4]diazepin-8-ylidenecyanamide, 1-Ethyl-5-(4-hydroxyphenyl)-3-isopropyl-6,7-dihydro-1H-pyrazolo[4,3-e][1,4]diazepin-8-one,
5-(4-Hydroxyphenyl)-3-isopropyl-1-propyl-6,7-dihydro-1H-pyrazolo[4,3-e][1,4]diazepin-8-one,
3-tert-Butyl-1-ethyl-5-(4-hydroxyphenyl)-6,7-dihydro-1H-pyrazolo[4,3-e][1,4]diazepin-8-one.

Among the preferred compounds of the present invention, the compounds below are particularly preferred:
1-Ethyl-3-isopropyl-5-phenyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-one,
1-Ethyl-3-isopropyl-5-phenyl-6,7-dihydro-1H-pyrazolo[4,3-e][1,4]diazepin-8-thione,
5-(4-Aminophenyl)-1-ethyl-3-isopropyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-one,
4-(1-Ethyl-3-isopropyl-8-oxo-1,6,7,8-tetrahydro-pyrazolo[4,3-e][1,4]diazepin-5-yl)benzonitrile,
5-tert-Butyl-3-isopropyl-1-propyl-6,7-dihydro-1H-pyrazolo[4,3-e][1,4]diazepin-8-one,
4-(3-Isopropyl-8-oxo-1-propyl-1,6,7,8-tetrahydro-pyrazolo[4,3-e][1,4]diazepin-5-yl)benzonitrile,
3-tert-Butyl-1-ethyl-5-p-tolyl-6,7-dihydro-1H-pyrazolo[4,3-e][1,4]diazepin-8-one,
3-Butyl-1-ethyl-5-phenyl-6,7-dihydro-1H-pyrazolo[4,3-e][1,4]diazepin-8-thione,
(±)3-sec-Butyl-1-ethyl-5-pyrid-4-yl-6,7-dihydro-1H-pyrazolo[4,3-e][1,4]diazepin-8-one,
(±)3-sec-Butyl-1-propyl-5-pyrid-4-yl-6,7-dihydro-1H-pyrazolo[4,3-e][1,4]diazepin-8-one,
3-Cyclohexyl-1-propyl-5-pyrid-4-yl-6,7-dihydro-1H-pyrazolo[4,3-e][1,4]diazepin-8-one,
3-tert-Butyl-5-(4-methoxyphenyl)-1-propyl-6,7-dihydro-1H-pyrazolo[4,3-e][1,4]diazepin-8-one,
1-Ethyl-5-(2-hydroxyphenyl)-3-methyl-6,7-dihydro-1H-pyrazolo[4,3-e][1,4]diazepin-8-one,
3-tert-Butyl-1-ethyl-5-(4-hydroxyphenyl)-6,7-dihydro-1H-pyrazolo[4,3-e][1,4]diazepin-8-one,
1-Ethyl-3-isopropyl-5-phenyl-6,7-dihydro-1H-pyrazolo[4,3-e][1,4]diazepin-8-ylidenecyanamide.

Derivatives of the Compounds of the Invention

The compounds used in the invention include the solvates, the hydrates, the pharmaceutically acceptable salts and the polymorphs (different crystal structures) of the compounds according to the invention, which are designated as being pharmaceutically acceptable derivatives thereof.

The pharmaceutically acceptable salts include, for example: acetate, benzenesulphonate, benzoate, bicarbonate, bitartrate, bromide, calcium acetate, camsylate, carbonate, chloride, citrate, dihydrochloride, edetate, edisylate, estolate, esylate, fumarate, gluceptate, gluconate, glutamate, glycoloylarsanilate, hexylresorcinate, hydrabamine, hydrobromide, hydrochloride, hydroxynaphthoate, iodide, isethionate, lactate, lactobionate, malate, maleate, mandelate, mesylate, methyl bromide, methyl nitrate, methyl sulphate, mucate, napsylate, nitrate, pamoate (embonate), pantothenate, phosphate/diphosphate, polygalacturonate, salicylate, stearate, subacetate, succinate, sulphate, tannate, tartrate, theoclate, triethiodide, benzathine, chloroprocaine, choline, diethanolamine, ethylenediamine, meglumine, procaine, aluminium, calcium, lithium, magnesium, potassium, sodium and zinc (see also "Pharmaceutical salts" by Berge S. M. et al. (1997) *J. Pharm. Sci.* 66: 1–19, the content of which is incorporated into the present invention by way of reference).

The use of a prodrug of a compound according to the invention is also envisaged. (See in particular Bundgaard, et al., *Acta Pharm. Suec.*, 1987; 24: 233–246).

Mixtures of compounds are also envisaged.

Pharmaceutical Formulation of the Compounds of the Invention

The compounds of the invention are administered in the form of compositions that are appropriate for the nature and seriousness of the complaint to be treated. The daily dosage in man is usually between 2 mg and 1 g of product, which can be absorbed in one or more intakes. The compositions are prepared by methods that are common to those skilled in the art and generally comprise 0.5 to 60% by weight of active principle (compound of formula I) and 40 to 99.5% by weight of pharmaceutically acceptable vehicle. The compositions of the present invention are thus prepared in forms that are compatible with the desired route of administration. By way of example, the following pharmaceutical forms may be envisaged, although the list given below is not limiting:

1) Forms for Oral Administration:

Tablets, cachets, sachets of powder for drinkable suspension, gel capsules, gastro-resistant gel capsules, sustained-release forms, emulsions, HPMR wafer capsules or gel capsules, lyophilizates to be melted under the tongue, drinkable solutions, suspensions and sachets of powder for a drinkable solution., The powders, tablets, cachets or encapsulated forms preferably contain from 5% to 70% of active principle. Suitable supports are, for example, magnesium carbonate, magnesium stearate, talc, lactose, sugar, pectin, dextrin, starch, gum tragacanth, methylcellulose, sodium carboxymethylcellulose, low-melting wax, cocoa butter and the like.

The tablets, powders, cachets and capsules can be used as a unit dosage for oral administration.

In the powders, the support is a finely divided solid, which is in a mixture with the finely divided compound of general formula I.

In the tablets, the active compound is mixed with the support which has the required binding properties, in a suitable amount, and the mixture is then tableted into the required shape and size.

The aqueous solutions for oral administration can be prepared by dissolving the active principle and adding, if necessary, dyes, flavour enhancers, flavourings, stabilizers, thickeners, etc. By way of example, the active principle can be dispersed in the form of finely divided powder in water with a viscous material such as synthetic gums, resins, methylcellulose, sodium carboxymethylcellulose and other suspension agents known in the pharmaceutical field.

2) Forms for Parenteral Administration:

Intravenous Route:

Aqueous solutions, water/co-solvent solutions, solutions using one or more solubilizing agents, colloidal suspensions, emulsions, nanoparticulate suspensions which can be used for injecting sustained-release forms, dispersed forms and liposomes.

Sterile solutions of the active principle in water and/or propylene glycol can be mentioned as examples of liquid preparations which are suitable for parenteral administration. The liquid preparations can also be formulated in the form of aqueous solutions of polyethylene glycol.

Subcutaneous/Intramuscular Route:

In addition to the forms that can be used intravenously which can also be used for the subcutaneous and intramuscular routes, other types of forms such as suspensions, dispersed forms, sustained-release gels and sustained-release implants can also be used.

3) Forms for Topical Administration:

Among the most common topical forms are creams, gels (aqueous phases gelled with polymers), patches, which are dressings to be stuck directly on the skin and which can be used for treating dermatoses without percutaneous penetration of the active substance, sprays, emulsions and solutions.

4) Forms for Pulmonary Administration:

Distinguished in this category are forms such as solutions for aerosols, powders for inhalers and other suitable forms.

5) Forms for Nasal Administration:

This relates especially to solutions or suspension for drops.

6) Forms for Rectal Administration:

Suppositories and gels will be selected, inter alia.

For the preparation of suppositories, a low-melting wax, such as a mixture of fatty acid glycerides and cocoa butter, is melted in a first stage, and the active principle is then dispersed therein, for example with mechanical stirring. The molten homogeneous mixture is then poured into moulds of appropriate shape and then left to cool and solidify.

It may also be envisaged to use forms allowing the administration of ophthalmic solutions or allowing the administration of the active principle via the vaginal route.

Another important category of pharmaceutical form which can be used in the context of the present invention relates to forms for improving the solubility of the active principle. By way of example, it may be envisaged to use aqueous solutions of cyclodextrin, and more particularly forms comprising hydroxypropyl beta cyclodextrin. A detailed review of this type of pharmaceutical form is given in the article published under the reference *Journal of Pharmaceutical Sciences,* 1142–1169, 85 (11), 1996, and incorporated into the present patent application by way of reference.

The various pharmaceutical forms recommended above are described in detail in the book <<Pharmacie galénique [Pharmaceutical pharmacy]>>by A. Lehir (published by Masson, 1992 (6th edition)), which is incorporated into the present patent application by way of reference.

Synthesis of the Compounds of the Present Invention

A subject of the invention is also a process for preparing the compounds according to the invention, as illustrated in the reaction schemes below. The starting materials are commercially available or can be synthesized by standard methods.

Reaction Scheme 1

In the description which follows, each of the steps of the reaction scheme is described in general. This process and its various steps are exemplified in Example 1. If a step can be carried out according to various methods (depending on the compounds under consideration), they will be described (M1, M2, . . . ) and identified relative to a literature reference. The starting materials are chosen in an appropriate manner (it being possible for the reactive functions, if any, to be protected in a conventional manner).

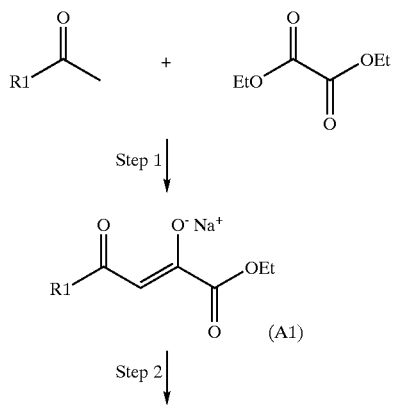

-continued
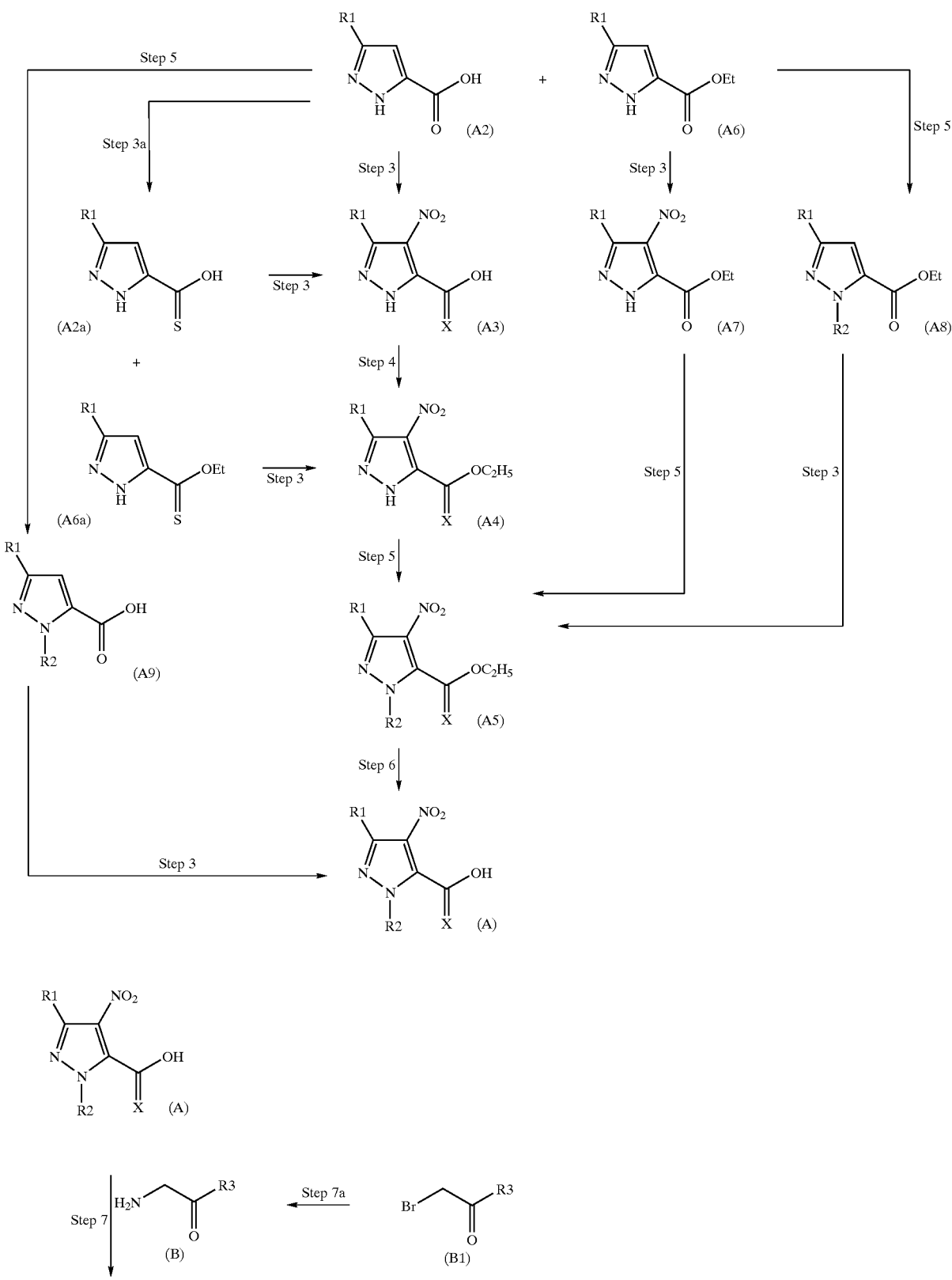

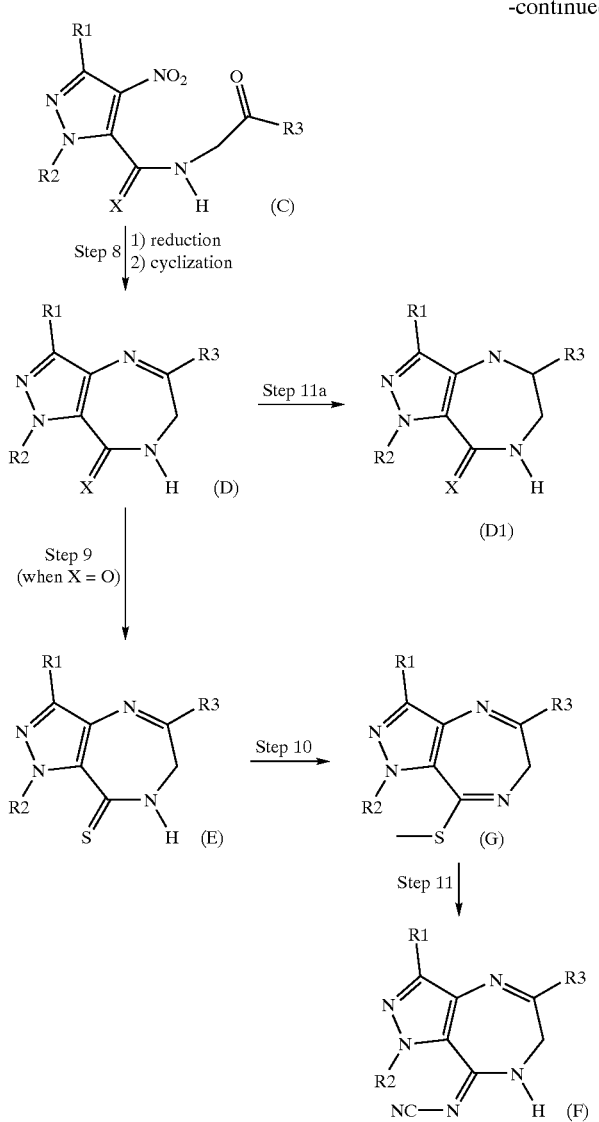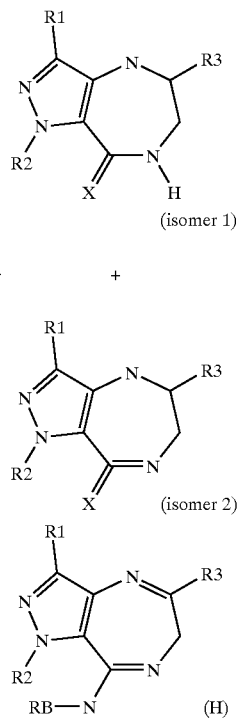

Step 1:
An R1-methyl ketone in which R1 is one of the substituents of the compound of general formula I is reacted with a diethyl oxalate in the presence of sodium to give the compound of general formula A1.

Step 2:
A cyclization of the compound A1 is then carried out, for example with hydrazine sulphate in the presence of potassium hydroxide to give a mixture of the pyrazole (A2) and the pyrazole (A6) each comprising the substituent R1. These two intermediates may be separated and reacted subsequently.

Step 3a:
Step 3a is an alternative step to step 9 described below. It allows the introduction of a sulphur atom into the position of the substituent X from the very first steps of the synthesis, by reacting A2 or A6 with a suitable reagent, for example, Lawesson's reagent, to give a compound of formula A2a or A6a in which X is equal to O or S and R1 is defined as above.

Step 3:
Step 3 essentially comprises the nitration of the pyrazole nucleus. This nitration is carried out on the compounds A2, A2a, A6, A6a, A8 or A9 and can be carried out according to 3 methods desribed in the literature:
using NaNO$_3$/H$_2$SO$_4$ (method M1), see Example 1; *Aust. J. Chem.*, 47, 1009–1021, 1994;
using HNO$_3$/H$_2$SO$_4$, (method M2);
or using Cu(NO$_3$)$_2$ (method M3), *J. Org. Chem.*, 46, 3056–3060, 1981 to give a compound of formula A, A3, A4, A5 or A7 in which X is equal to O or S.

Step 4:
In this step, compound A3 is esterified. This can be carried out by reacting compound A3 with ethanol in acidic medium. Compound A4 in which X is equal to O or S and R1 is as defined above is thus obtained.

Step 5:
The pyrazoles A2, A4, A6 and A7 are alkylated according to various methods:
by reacting dimethyl sulphate (to give derivatives with R2=ethyl) (methode M4), *J. Med. Chem.* 16, 12, 1346–1354, 1973;
by reacting with a compound of the type R2-hal, in which R2 is as defined for the compound of general formula I and hal is a halogen (method M5).

A compound of formula A5, A8 or A9 in which X is equal to O or S is obtained.

Step 6:

During this step, the ester function (X=O) or thioester function (X=S) is hydrolysed, for example by reacting compound AS with sodium hydroxide. This gives compound A in which X is equal to O or S and R1 and R2 are as defined above.

Step 7:

During this step, compound A is reacted with compound B of general formula

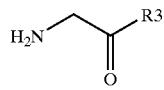

in which R3 is one of the substituents of the compound of general formula I. Preferably, a hydrochloride of compound B is used. When it is not commercially available, the product (B) is synthesized in one step (step 7a), starting with compound (B1), which is commercially available or described in the literature. The nucleophilic substitution of the bromine with the primary amine function is obtained according to various methods:

Delepine method (method M6), *J. Heterocyclic Chem.*, 24, 297–301, 1987.

Method via the synthesis of a bisformamide (method M7), *Tetrahedron. Lett.*, 30, 39, 5285-58-286, 1889; *Synthesis*, 122–124, 1990.

Compound C in which X is equal to O or S is obtained according to various coupling methods (step 7):

Method of coupling N-hydroxysuccinimide and dicyclohexylcarbodiimide (method M8, see example 1)

Method of coupling on a solid support (method M9): compound A (1 eq.) is reacted with N-cyclohexylcarbodiimide and N'-methylpolystyrene HL (2 eq.) in dichloromethane. After stirring for half an hour, compound B (1 eq.) and triethylamine (1 eq.) are added. After 24 hours at room temperature, methyl isocyanate polystyrene HL is added. After 2 hours, the reaction medium is filtered and the filtrate is concentrated to give compound C in which X is equal to O or S.

Method of coupling with EDCI 1-(3-dimethylaminopropyl)-3-ethylcarbodiimide hydrochloride and HOBt (1-hydroxybenzotriazole) (method M10): compound B is reacted, with stirring, with compound A in equimolar amount in dichloromethane in the presence of one equivalent of triethylamine, one equivalent of 1-hydroxybenzotriazole and one equivalent of 1-(3-dimethylaminopropyl)-3-ethylcarbodiimide hydrochloride. After 24 hours at room temperature, the reaction medium is washed with water; the organic phase is dried and evaporated to dryness to give the compound of formula C in which X is equal to O or S and R1, R2 and R3 are as defined above.

Step 8:

During this step, compound C is cyclized according to various methods to give compound D in which X is equal to O or S and R1, R2 and R3 are as defined above:

using Fe/HCl (method M11) (see example 1);

using $SnCl_2$ (method M12): an amide of type C is dissolved in ethanol with 5 equivalents of tin chloride dihydrate. The reaction medium is refluxed for 4 hours. After cooling to room temperature, demineralized water is added and, when cold, the solution is brought to basic pH with 30% sodium hydroxide. After extraction with $CH_2Cl_2$ and drying, the medium is evaporated to dryness to give the compound of type D, which is purified, if necessary, on silica or by crystallization.

Step 9:

Step 9 is used when it is desired to obtain a compound of formula I in which X is S if, in compound D, X is O. The compounds of this type are obtained by reacting compound D, in which X is O, with a suitable reagent, allowing its thionation to be carried out. By way of example, Lawesson's reagent may be used. A compound of formula E in which X is S is thus obtained.

Steps 10 and 11:

Steps 10 and 11 are used when it is desired to obtain a compound of formula I in which X is N—CN. The compounds of this type are obtained according to various methods:

method M13: by reacting compound E with sodium hydride and then with iodomethane to give compound (G). This compound is then placed in contact with cyanamide and triethylamine to give a compound of type (F); *Heterocycles*, 36, 777–783, 1993.

method M14: $Ph_3PSnN=C=NSnPPh_3$ in ethanol; *J. Med. Chem.*, 35, 12, 2327–2340, 1992.

method M15: phosphoryl chloride, cyanamide and triethylamine; *Chem. Pharm. Bull.*, 42, 12, 2475–2482, 1994.

method M16: cyanamide, triethylamide [sic], mercury acetate and acetonitrile; *Can. J. Chem.*, 63, 3089–3101, 1985.

Steps 11a and 11b:

Step 11a makes it possible to reduce the imine function of compound D by reacting it with a reducing agent, for example $NaBH_4$ in a polar mixture, for example methanol/water in the presence of palladium-on-charcoal to give the racemate D1 in which X is O or S and R1, R2 and R3 are as defined above, and the following step (11b) corresponds to the separation of the enantiomers (isomer 1 and isomer 2), for example by means of HPLC on a Diacel OD-H chiral column (250 mm×4.6 mm, 5 µm, flow rate 1 ml/min, 80/20 heptane/isopropanol).

These steps, 11a and 11b, also apply in the case of a compound of formula D in which X is N—CN or N—$R_B$.

Steps 10 and 12:

Steps 10 and 12 are used to obtain compounds of the type H. Step 10 allows the formation of the derivative G and step 12 leads to the introduction of the group N—RB according to a method inspired by the literature: *J. Med. Chem.*, 42, 2909–2919, 1999.

Reaction scheme 2:

This reaction scheme results in the synthesis of derivatives D in which X is O with R1=aryl containing from 5 to 10 carbon atoms, optionally interrupted with a hetero atom chosen from nitrogen, oxygen and sulphur and R2 and R3 are as defined above. This process is illustrated by Example 4.

31

Reaction scheme 2

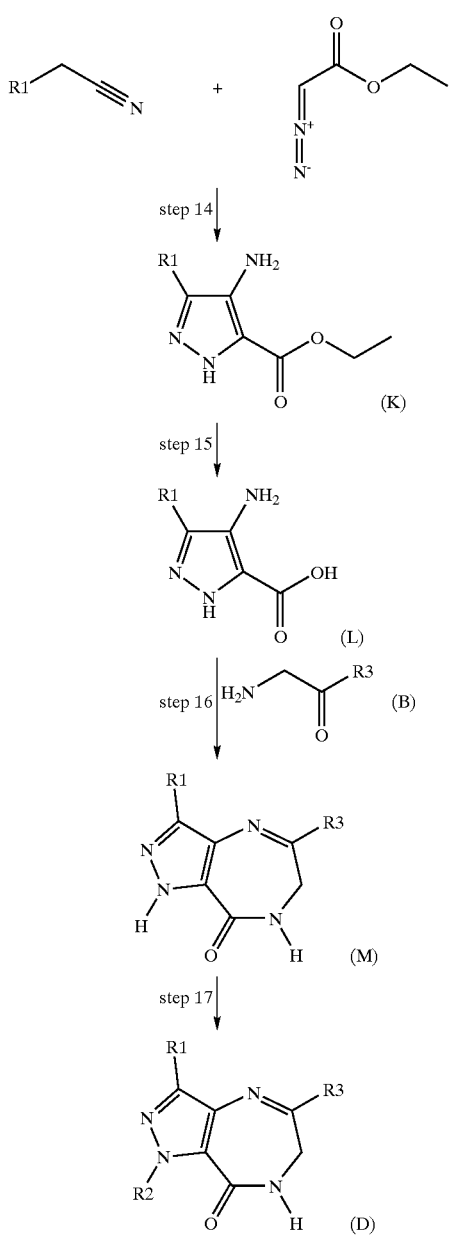

32

Step 14:

The synthesis of the pyrazole is carried out under the conditions described in *Farmaco Ed. Sci.*, 39, 7, 1984, 618–636.

Step 15:

During this step, the ester function of compound K is hydrolysed, for example by reacting compound K with sodium hydroxide. This gives compound L.

Step 16:

This step leads to the formation of the derivative M after coupling with compound B and cyclization.

Step 17:

This step allows the formation of the compounds D with X=O and R1=aryl containing from 5 to 10 carbon atoms, optionally interrupted with a hetero atom chosen from nitrogen, oxygen and sulphur and R2 and R3 are as defined above.

Compound M is alkylated by reacting it with a compound of the type R2-hal, in which R2 is as defined for the compound of general formula I and hal is a halogen. Compound D is thus obtained.

Reaction Scheme 3

This scheme describes the synthesis of compounds D with $R1=(CH_2)_nOR_B$ or $(CH_2)_nCOOR_B$. These molecules can lead, via standard reactions of organic chemistry, to the formation of compounds D with $R1=(CH_2)_nC(O)R_B$, $(CH_2)_nOC(O)R_A$, $(CH_2)_nSR_B$, $(CH_2)_nNR_BR_C$, $(CH_2)_nC(O)NR_BR_C$, $(CH_2)_nNR_CC(O)R_B$ or $(CH_2)_nZ$ with n, $R_A$, $R_B$, $R_C$ and Z as described above.

Steps 3, 5, 7 and 8 are described above in general.

Steps 5, 18, 3, 7 and 8 are illustrated by Example 5 and steps 19, 20 and 21 by Example 97.

Reaction scheme 3

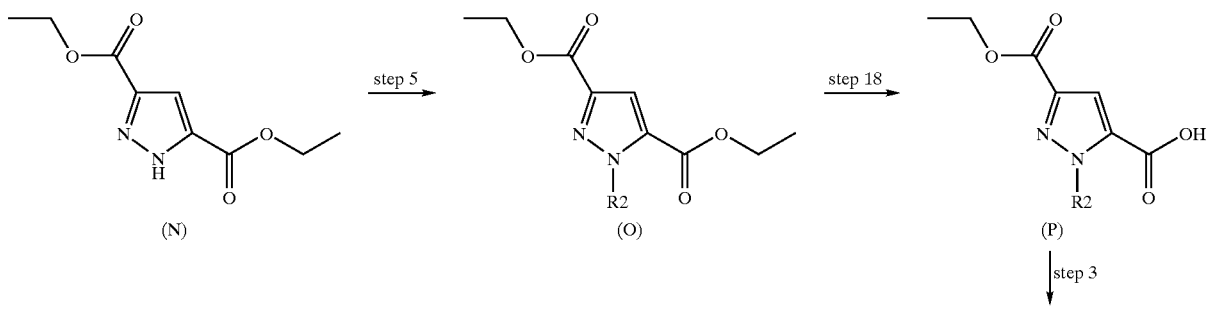

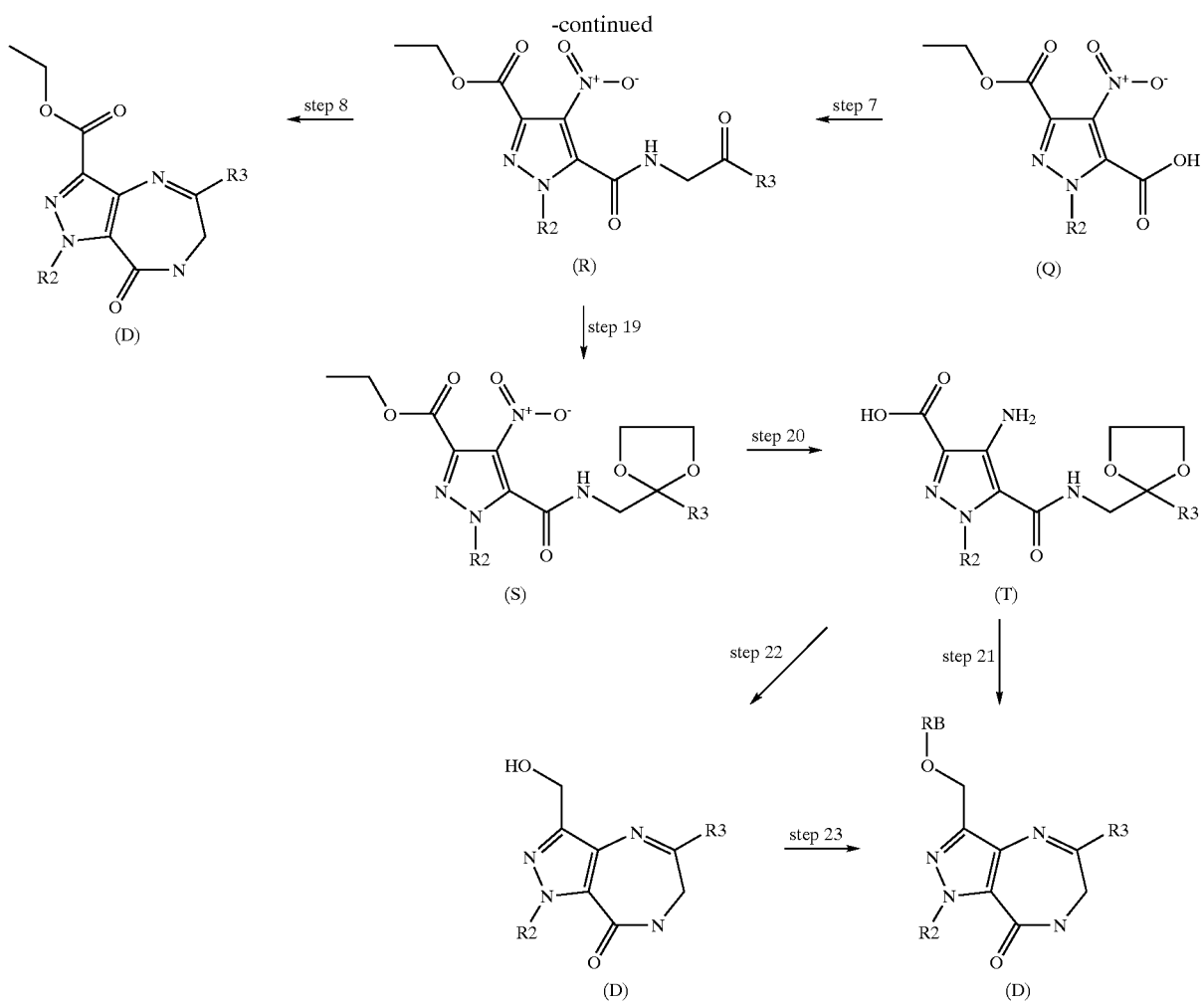

Step 22:

This cyclization step is carried out in acidic medium, for example 5% HCl, in an aprotic solvent such as tetrahydrofuran, to give the hydroxy derivative D with $R1=CH_2OH$.

Step 23:

This step leads to the synthesis of various derivatives D ($R1=OR_B$) using, for example, a compound of the type RB-hal, in which $R_B$ is as defined above and hal is a halogen.

Step 21:

This step is limited to the use of hydroxylated solvents such as MeOH and EtOH, during the cyclisation step of compound T, also allows the synthesis of compounds D with $R1=OR_B$.

Reaction Scheme 4

This is an alternative method for sythesizing the compounds of general formula I in which X is O or S and R1, R2 and R3 are as defined above. This alternative method is illustrated in the scheme below.

Reaction scheme 4

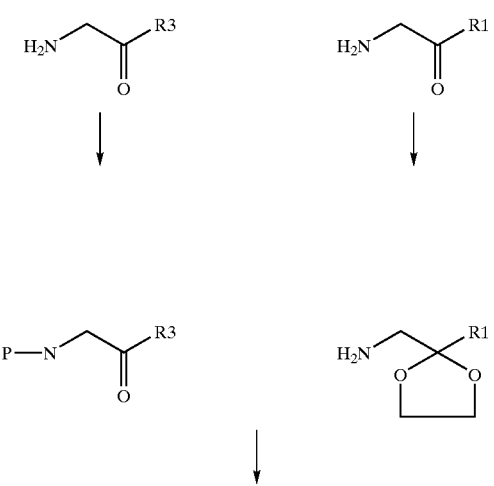

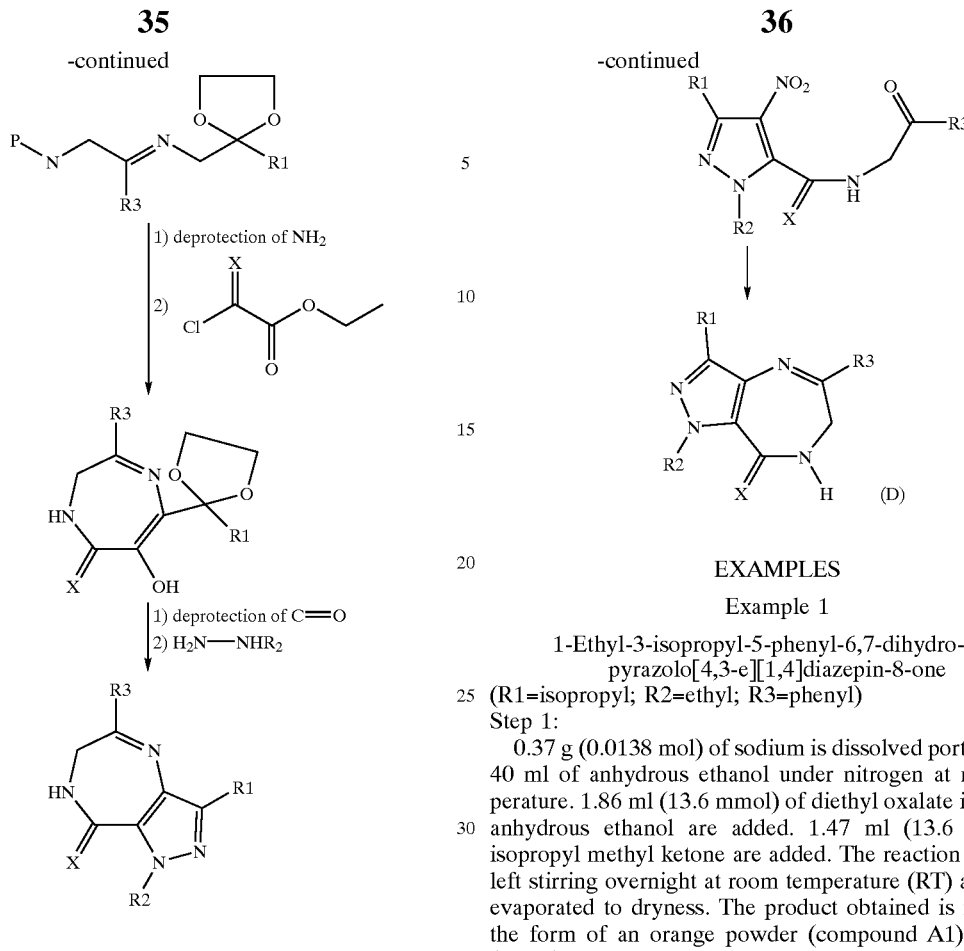

Reaction Scheme 5

This is another method for synthesizing compounds of general formula I in which X is O or S. This method is illustrated in summary in the scheme given below. A more detailed description of this synthesis is presented in U.S. Pat. No. 5,272,147, the content of which is incorporated into the present patent application by reference.

Reaction scheme 5

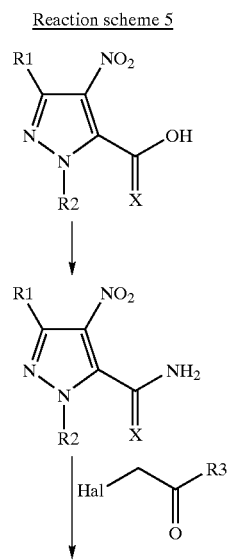

EXAMPLES

Example 1

1-Ethyl-3-isopropyl-5-phenyl-6,7-dihydro-1H-pyrazolo[4,3-e][1,4]diazepin-8-one (R1=isopropyl; R2=ethyl; R3=phenyl)

Step 1:

0.37 g (0.0138 mol) of sodium is dissolved portionwise in 40 ml of anhydrous ethanol under nitrogen at room temperature. 1.86 ml (13.6 mmol) of diethyl oxalate in 10 ml of anhydrous ethanol are added. 1.47 ml (13.6 mmol) of isopropyl methyl ketone are added. The reaction mixture is left stirring overnight at room temperature (RT) and is then evaporated to dryness. The product obtained is isolated in the form of an orange powder (compound A1): m=3.1 g (100%).

MS (ES+), m/z=185

Rf ($CH_2Cl_2$/acetone 90/10)=0.91

Step 2:

0.98 g (14.8 mmol) of potassium hydroxide is dissolved in 7.5 ml of water and the reaction medium is cooled to 0° C. 3.1 g (14.8 mmol) of compound A1 (see scheme 1) are added portionwise and the mixture is stirred for 30 min at 0° C. 1.94 g (14.8 mmol) of hydrazine sulphate are added and the mixture is then stirred for 45 min at 0° C. After filtration, the precipitate is rinsed with a small amount of water and then dried to give 0.93 g (13%) of a white powder (compound A2).

$^1$H NMR (DMSO, 400 MHz)

1.2 ppm (6H, d); 2.95 ppm (1H, m); 6.45 ppm (1H, s); 12.3 ppm (1H, m)

Step 3:

Method M1 is used. 100 ml of concentrated $H_2SO_4$ are introduced into a round-bottomed flask. The flask is cooled to 0° C. and 10.09 g (0.065 mol) of compound A2 (see scheme 1) (0.065 mol) are added, followed by addition of 16.5 g (0.195 mol) of $NaNO_3$. The mixture is warmed to RT and stirred for 24 h. The reaction medium is poured gently into 200 ml of ice-cold water, cooling the flask if necessary, and stirred for 30 min. The precipitate is filtered off and rinsed with water. After drying, 4.25 g (33%) of a white powder are obtained (compound A3).

MS (ES−) m/z=198

$^1$H NMR (DMSO, 400 MHz)

1.3 ppm (6H, d); 3.5 ppm (1H, m); 13.9 ppm (2H, m)

Step 4:

A mixture of 4.25 g of compound A3 (0.021 mol), 24 ml of ethanol and 2.3 ml of concentrated $H_2SO_4$ in a round-bottomed flask is refluxed for 4.5 h. The reaction medium is evaporated and then taken up in CH$_2$Cl$_2$ and washed with water; after drying over MgSO$_4$, the organic phase is filtered and then concentrated to give 4 g (83%) of powder (compound A4).

MS (ES+), m/z=228
Rf (CH$_2$Cl$_2$/MeOH95/5)=0.52

Step 5:

Method M5 is used. 2.77 g (0.02 mol) of K$_2$CO$_3$ are added under a stream of nitrogen to a solution of 4 g (0.02 mol) of compound A4 in 40 ml of anhydrous DMF, followed by addition of 1.76 ml (0.022 mol) of iodoethane. The reaction medium is heated at 60° C. for 16.5 h. After filtering off the precipitate, the filtrate is taken up in diethylether (100 ml) and this organic phase is washed with water, dried over MgSO$_4$, filtered and then concentrated to give 4 g of an oily compound.

This crude product is purified by flash chromatography on a column of silica using the following elution gradient: from 50/50 CH$_2$Cl$_2$/heptane to 80/20 CH$_2$Cl$_2$/heptane to give 2.92 g (57%) of a yellow oil (compound A5).

MS (ES+), m/z=256
$^1$H NMR (CDCl$_3$, 400 MHz)
1.3 ppm (6H, d); 1.35 ppm (3H, t); 1.45 ppm (3H, t); 3.45 ppm (1H, m); 4.2 ppm (2H, g); 4.45 ppm (2H, q)

Step 6:

2.92 g (0.011 mol) of compound A5 (see scheme 1) are introduced into 15 ml of methanol in a round-bottomed flask, followed by addition of a solution of 0.68 g (0.0165 mol) of sodium hydroxide in 15 ml of water. The mixture is stirred at RT for 3 h. After evaporating off the methanol, the residue is taken up in CH$_2$Cl$_2$, an identical volume of water is added and the resulting mixture is then acidified (with stirring) with concentrated (36%) HCl. After separation of the phases by settling, the organic phase is dried over Na$_2$SO$_4$ and concentrated to give 2.3 g of a white powder (92%) (compound A).

MS (ES-), m/z=226
$^1$H NMR (DMSO, 400 MHz),
1.2 ppm (6H, d); 1.35 ppm (3H, t); 3.35 ppm (1H, m); 4.15 ppm (2H,q)

Step 7:

Method M8 is used. 1 g (4 mmol) of compound A (see scheme 1) is dissolved in a mixture of 25.7 ml of THF and 1.4 ml of DMF, followed by addition, under nitrogen, of 0.51 g (4 mmol) of N-hydroxysuccinimide. The reaction medium is cooled to 0° C. so as to add portionwise 0.91 g (4 mmol) of dicyclohexylcarbodiimide. The mixture is stirred overnight at RT. The precipitate formed is filtered off and the filtrate is evaporated to dryness. The residue is taken up in 20 ml of CH$_2$Cl$_2$, 0.75 g (4 mmol) of 2-aminoacetophenone hydrochloride is added under nitrogen, the reaction medium is cooled to 0° C., 0.61 ml (4 mmol) of triethylamine is then added and the mixture is stirred at RT for 3 h. The reaction medium is poured into water with stirring. After extraction with dichloromethane, washing with water and drying over Na$_2$SO$_4$, the organic phase is evaporated to dryness to give 1.3 g (86%) of a white powder (compound C).

MS (ES+), m/z=345
$^1$H NMR (CDCl$_3$, 400 MHZ),
1.35 ppm (6H, d); 1.5 ppm (3H, q); 3.55 ppm (1H, m); 4.3 ppm (2H, q); 5 ppm (2H, d); 7.5 ppm (2H, t); 7.65 ppm (1H, d); 7.7 ppm (1H, m); 8 ppm (2H, d).

Step 8:

Method M11 is used. 1.3 g (3.7 mmol) of compound C (see scheme 1) are introduced into a mixture of 30 ml of ethanol and 7 ml of water in a round-bottomed flask, followed by addition of 2.2 g (3.9 mmol) of iron and 0.5 ml of conc. (36%) HCl. The reaction medium is refluxed for 1 h 15 min. The iron is removed by filtration. The filtrated is concentrated to dryness and the residue is taken up in CH$_2$Cl$_2$ and washed with twice 70 ml of water and then with saturated NaCl solution; the organic phase is dried over Na$_2$SO$_4$, filtered and concentrated to give an amorphous red powder (m=0.9 g).

This crude product is purified by flash chromatography using the following elution gradient: 98/2 CH$_2$Cl$_2$/acetone to 90/10 CH$_2$Cl$_2$/acetone.

The red powder obtained after evaporation is taken up in the minimum amount of diethyl ether and then filtered. After drying, 0.35 g (32%) of a beige powder (compound D) is isolated.

MS (ES+), m/z=297
m.p.=157.2° C.
$^1$H NMR (CDCl$_3$, 400 MHZ),
1.4 ppm (6H, d); 1.5 ppm (3H, t); 3.35 ppm (1H, m); 4.1 ppm (2H, d); 4.55 ppm (2H, q); 6.25 ppm (1H, m); 7.45 ppm (3H, m); 8.0 ppm (2H, m).

Example 2

1-Ethyl-3-isopropyl-5-phenyl-6,7-dihydro-1H-pyrazolo[4,3-e][1,4]diazepin-8-thione (R1=isopropyl; R2=ethyl; R3=phenyl)

Step 9:

0.2 g (0.67 mmol) of compound D (see scheme 1) is dissolved in 7 ml of toluene over sieves, and 0.54 g (1.34 mmol) of Lawesson's reagent is added, under nitrogen. The mixture is refluxed for 16.5 h. The reaction medium is cooled to RT; 2 ml of 5% HCl are then added, followed by 25 ml of methanol and 25 ml of cyclohexane, the mixture is stirred, the precipitate is then filtered off and the two phases are allowed to separate by settling. The methanol phase is evaporated. The residue is taken up in ethyl acetate and washed with water; the organic phase is dried over Na$_2$SO$_4$, filtered and evaporated.

The crude product is purified by flash chromatography (80/20 cyclohexane/ethyl acetate). After evaporation, 0.15 g (75%) of a yellow powder (compound E) is obtained.

MS (ES+), m/z=313
m.p.=164° C.
$^1$H NMR (CDCl$_3$, 400 MHz),
1.4 ppm (6H, d); 1.5 ppm (3H, t); 3.3 ppm (1H, m); 4.2 ppm (2H, m); 4.8 ppm (2H, q); 7.45 ppm (3H, m); 8 ppm (2H, d); 8.3 ppm (1H, m)

Example 3

1-Ethyl-3-isopropyl-5-phenyl-6,7-dihydro-1H-pyrazolo[4,3-e][1,4]diazepin-8-ylidenecyanamide (R1=isopropyl; R2=ethyl; R3=phenyl)

Step 10:

According to M13, 1.83 g (5.86 mmol) of 1-ethyl-3-isopropyl-5-phenyl-6,7-dihydro-1H-pyrazolo[4,3-e][1,4] diazepin-8-thione are reacted with 0.18 g of 80% sodium hydride in refluxing THF for 1 h, and 0.44 ml of methyl iodide is then added at room temperature. The mixture is refluxed for 2 h to give 1.53 g (80%) of the expected methylsulphanyl of type G (see Scheme 1).

m.p.=98° C.
MS (ES+), m/z=327
$^1$H NMR (DMSO, 400 MHz), 8.1 ppm (2H, d); 7.4 ppm (3H, m); 4.4 ppm (4H, m); 3.2 ppm (1H, m); 2.4 ppm (3H, s); 1.4 ppm (3H, t); 1.3 ppm (6H, m)

Step 11:

0.5 g (1.53 mmol) of the methylsulphanyl G is reacted with 0.12 g (2 eq.) of cyanamide to give 0.396 g (81%) of the expected product of type F (see Scheme 1).

m.p.=222° C.

MS (ES+), m/z=321

$^1$H NMR (DMSO, 400 MHz), 9.4 ppm (1H, 1s); 8 ppm (2H, m); 7.4 ppm (3H, m); 4.3 ppm (2H, g); 4.1 ppm (2H, 1s); 3.1 ppm (1H, m); 1.3 ppm (3H, t); 1.2 ppm (6H, d)

Example 4

1-Ethyl-3,5-diphenyl-6,7-dihydro-1H-pyrazolo[4,3-e][1,4]diazepin-8-one,
(R1=phenyl; R2=ethyl; R3=phenyl)
Step 15:

35.75 g (0.15 mol) of compound K (see scheme 2) in 35 ml of methanol are introduced into a round-bottomed flask, followed by addition of a solution of 9.24 g (0.231 mol) of sodium hydroxide in 140 ml of water. The mixture is stirred at room temperature overnight. After evaporation, the residue is taken up in ethanol and then filtered and dried to give 26.7 g (87%) of a beige powder (compound L, see scheme 1).

MS (ES+), m/z=203.9

$^1$H NMR (DMSO, 400 MHz) 4.7 ppm (2H, m); 7.2 ppm (1H, m); 7.3 ppm (2H, t); 7.75 ppm (2H, d); 12.2 ppm (1H, m)

Step 16:

1.5 g (8.7 mmol) of 2-aminoacetophenone hydrochloride are dissolved in a mixture of 50 ml of THF and 10 ml of DMF, followed by addition of 1.22 ml (8.7 mmol) of triethylamine, 1.34 g (8.7 mmol) of 1-hydroxybenzotriazole hydrate and then 1.77 g (8.7 mmol) of compound L (see scheme 2) and finally 1.37 g (8.7 mmol) of 1-(3-dimethylaminopropyl)-3-ethylcarbodiimide. The mixture is heated at 60° C. for 24 h. The precipitate formed is filtered off and the filtrate is taken up in water. After extraction with ethyl acetate, the extracts are washed with water and dried over $Na_2SO_4$. The organic phase is evaporated to dryness to give 1.8 g of an orange powder. This crude product is purified by flash using the following elution gradient: from $CH_2Cl_2$ to 95/5 $CH_2Cl_2$/methanol to give 0.45 g (16%) of a beige powder (compound M, see scheme2).

MS (ES+), m/z=303

$^1$H NMR (DMSO, 400 MHz) 4.15 ppm (2H, m); 7.3–7.55 ppm (6H, m); 8–8.1 ppm (4H, m); 8.3 ppm (1H, m); 14 ppm (1H, m)

Step 17:

According to M5, 1.23 g (8.9 mmol) of $K_2CO_3$ are added, under a stream of nitrogen, to a solution of 2.7 g (8.9 mmol) of compound M (see scheme 2) in 30 ml of anhydrous DMF, followed by addition of 0.71 ml (8.9 mmol) of iodoethane. The reaction medium is heated at 60° C. overnight. The reaction medium is extracted with diethyl ether, and the extracts are dried over $Na_2SO_4$, filtered and then concentrated to give 3.6 g of an oily compound. This crude product is purified by flash using the following elution gradient: from $CH_2Cl_2$ to 98/2 $CH_2Cl_2$/acetone. The oily product thus obtained is crystallized from diethyl ether to give 0.2 g (7%) of a yellow powder (compound (see scheme 2))

MS (ES+), m/z=331

$^1$H NMR (DMSO, 400 MHZ) 1.4 ppm (3H, t); 4.1 ppm (2H, m); 4.5 ppm (2H, q); 7.3 ppm (1H, m); 7.4 ppm (2H, m); 7.5 ppm (3H, m); 8 ppm (4H, m); 8.5 ppm (1H, m)

Example 5

Ethyl 1-ethyl-8-oxo-5-phenyl-1,6,7,8-tetrahydropyrazolo-[4,3-e][1,4]diazepin-3-carboxylate (R1=ethyl carboxylate; R2=ethyl; R3=phenyl)
Step 5:

20 g (94 mmol) of diethyl 3,5-pyrazoledicarboxylate (commercial) are reacted with 8.3 ml (103 mmol) of iodo-ethane to give 21.4 g (95%) of a pyrazole O (see Scheme 3)

Rf (95/5 $CH_2Cl_2$/MeOH)=0.70

MS (ES+), m/z=240.8

$^1$H NMR (CDCl$_3$, 400 MHz), 7.25 ppm (1H, s); 4.6 ppm (2H, q); 4.25–4.4 ppm (4H, m); 1.4 ppm (3H, t); 1.3 ppm (6H, m)

Step 18:

21 g (87 mmol) of pyrazole O (see scheme 3) are reacted, under cold conditions, in 100 ml of water and 160 ml of THF with a solution of 3.84 g (96 mmol) of sodium hydroxide pellets in 100 ml of water. After warming to room temperature, the reaction mixture is stirred for 2 hours. The mixture is then extracted with diethyl ether. The aqueous phase is acidified with 36% HCl down to pH=2 and then extracted with dichloromethane. The organic phase is dried over $Na_2SO_4$ and then filtered and concentrated to give 13.5 g (73%) of compound P(see scheme 3).

Rf (80/20 $CH_2Cl_2$/MeOH)=0.55

MS (ES+), m/z=212.8

$^1$H NMR (CDCl$_3$, 400 MHz), 9.1–9.5 ppm (1H, m); 7.4 ppm (1H, s); 4.65 ppm (2H, q); 4.35 ppm (2H, q); 1.4 ppm (3H, t); 1.3 ppm (3H, t)

Step 3:

According to M3, 6 g (28 mmol) of compound P (see scheme3) are reacted with 19.75 g (84 mmol) of copper nitrate hemipentahydrate in a mixture of trifluoroacetic anhydride and chloroform, to give 6.9 g (95%) of compound Q (see scheme 3).

Rf (80/20 $CH_2Cl_2$/MeOH+0.3% HCOOH)=0.46

MS (ES$^-$), m/z=255.8

$^1$H NMR (DMSO, 400 MHz), 4.55 ppm (2H, q); 4.3 ppm (2H, q); 1.4 ppm (3H, t); 1.3 ppm (3H, t)

Step 7:

According to M8, 3 g (11.7 mmol) of compound Q (see scheme 3) are reacted with 2 g (11.7 mmol) of 2-aminoacetophenone hydrochloride to give 4.38 g of compound R (see Scheme 3).

MS (ES+), m/z=372.8

$^1$H NMR (CDCl$_3$, 400 MHz), 7.9 ppm (3H, m); 7.55 ppm (1H, m); 7.45 ppm (2H, m); 4.9 ppm (2H, d); 4.3–4.5 ppm (4H, m); 1.45 ppm (3H, t); 1.35 ppm (3H, t)

Step 8:

According to M11, 1 g (2.7 mmol) of compound R (see scheme 3) is refluxed with 0.3 g (5.4 mmol) of iron and 0.27 ml of 36% HCl in a mixture of ethanol and water to give 0.1 g (12%) of the expected compound D (see Scheme 3).

Rf (50/50 cyclohexane/EtOAc)=0.19

SM (ES$^+$), m/z=327

$^1$H NMR (CDCl$_3$, 400 MHz), 8.55 ppm (1H, m); 8.05 ppm (2H, m); 7.55 ppm (3H, m); 4.55 ppm (2H, q); 4.3 ppm (2H, q); 4.1 ppm (2H, d); 1.4 ppm (3H, t); 1.3 ppm (3H, t)

Example 6

1-Ethyl-5-(4-methoxyphenyl)-3-methyl-6,7-dihydro-1H-pyrazolo[4,3-e][1,4]diazepin-8-one (R1=methyl; R2=ethyl; R3=4-methoxyphenyl)

Step 7:

According to M8, 0.5 g (2.5 mmol) of 2-ethyl-5-methyl-4-nitro-2H-pyrazole-3-carboxylic acid (see *J. Med. Chem.*, 16, 1973, 1346–1354 or U.S. Pat. No. 3,700,657) is reacted with 0.5 g of 2-amino-4'-methoxyacetophenone hydrochloride to give 0.78 g (90%) of an amide of type C (see Scheme 1).

m.p.: 151° C.

Analysis calculated for $C_{16}H_{18}N_4O_5$

C, 55.49; H, 5.24; N, 16.11; O, 23.10 found: C, 55.45; H, 5.44; N, 16.09; O, 22.9

Step 8:

Acording to M11, 0.6 g (1.73 mmol) of the amide C (see scheme 1) is refluxed with 1.04 g of iron and 0.173 ml of 36% HCl in an ethanol/water mixture to give 0.35 g (70%) of the expected product D (see scheme 1).

m.p.: 178° C.

MS (ES$^+$), m/z=299

$^1$H NMR (CDCl$_3$, 400 MHz), 7.8 ppm (2H, d); 6.9 ppm (2H, d); 6.0 ppm (1H, t); 4.5 ppm (2H, q); 4.2 ppm (2H, d); 3.8 ppm (3H, s); 2.4 ppm (3H, s); 1.45 ppm (3H, t)

Example 7

5-(4-Bromophenyl)-1-ethyl-3-methyl-6,7-dihydro-1H-pyrazolo[4,3-e][1,4]diazepin-8-one (R1=methyl; R2=ethyl; R3=4-bromophenyl)

Step 7:

According to M8, 0.5 g (2.5 mmol) of 2-ethyl-5-methyl-4-nitro-2H-pyrazole-3-carboxylic acid is reacted with 0.51 g of 2-amino-4'-bromoacetophenone hydrochloride to give 0.57 g (60%) of an amide of type C (see Scheme 1).

m.p.: 184° C.;

$^1$H NMR (CDCl$_3$, 400 MHz), 8.0 ppm (1H, s); 7.8 ppm (2H, d); 7.6 ppm (2H, d); 4.9 ppm (2H, s); 4.3 ppm (2H, q); 2.5 ppm (3H, s); 1.5 ppm (3H, t)

Analysis calculated. for $C_{15}H_{15}BrN_4O_4$

C, 45.59; H, 3.83; Br, 20.22; N, 14.18; O, 16.19 found: C, 45.42; H, 3.74; Br, 19.99; N, 14.11; O, 16.22

Step 8:

According to M11, 0.475 g (1.2 mmol) of the amide C (see scheme 1) is refluxed with 0.721 g of iron and 0.12 ml of 36% HCl in an ethanol/water mixture to give 0.25 g (60%) of the expected product D (see Scheme 1).

m.p.: 223° C.

MS (ES$^+$), m/z=348

$^1$H NMR (CDCl$_3$, 400 MHz), 7.8 ppm (2H, d); 7.5 ppm (2H, d); 6.2 ppm (1H, s); 4.5 ppm (2H, q); 4.0 ppm (2H, s); 2.3 ppm (3H, s); 1.4 ppm(3H, t)

Example 8

1-Ethyl-3-methyl-5-naphth-2-yl-6,7-dihydro-1H-pyrazolo[4,3-e][1,4]diazepin-8-one (R1=methyl; R2=ethyl; R3=naphthyl)

Step 7:

According to M8, 0.45 g (2.25 mmol) of 2-ethyl-5-methyl-4-nitro-2H-pyrazole-3-carboxylic acid is reacted with 0.5 g of 2-amino-1-naphth-2-yl-ethanone hydrochloride to give 0.588 g (75%) of an amide of type C (see Scheme 1).

Rf (5/5 cyclohexane/EtOAc)=0.25

$^1$H NMR (CDCl$_3$, 400 MHz), 8.6 ppm (1H, t); 8.0 ppm (7H, m); 5.15 ppm (2H, d); 4.4 ppm (2H, q); 2.6 ppm (3H, s); 1.5 ppm (3H, t)

Step 8:

0.58 g (1.58 mmol) of amide C (see scheme 1) is refluxed with 0.948 g of iron and 0.158 ml of 36% HCl in an ethanol/water mixture to give 0.32 g (79%) of the expected product D (see Scheme 1).

m.p.: 193° C.

MS (ES$^+$), m/z=319

$^1$H NMR (CDCl$_3$, 400 MHz), 8.2 ppm (2H, m); 7.8 ppm (3H, m); 7.5 ppm (2H, m), 6.4 ppm (1H, t); 4.5 ppm (2H, q); 4.2 ppm (2H, d); 2.4 ppm (3H, s); 1.45 ppm (3H, t)

Example 9

5-(3-Chlorothien-2-yl)-1-ethyl-3-methyl-6,7-dihydro-1H-pyrazolo[4,3-e][1,4]diazepin-8-one (R1=methyl; R2=ethyl; R3=chlorothienyl)

Step 7:

According to M8, 0.235 g (1.18 mmol) of 2-ethyl-5-methyl-4-nitro-2H-pyrazole-3-carboxylic acid is reacted with 0.5 g of 2-amino-1-(3-chlorothien-2-yl)ethanone hydrochloride to give 0.32 g (76%) of an amide of type C (see Scheme 1) in which R1, R2 and R3 are as defined in this example.

Rf (5/5 cyclohexane/EtOAc)=0.53

$^1$H NMR (CDCl$_3$, 400 MHz), 7.9 ppm (1H, m); 7.7 ppm (1H, d); 7.1 ppm (1H, d); 5.0 ppm (2H, d); 4.45 ppm (2H, q); 2.6 ppm (3H, s); 1.5 ppm (3H, t)

Step 8:

According to M11, 0.31 g (0.87 mmol) of the amide C (see scheme 1) is refluxed with 0.52 g of iron and 0.087 ml of 36% HCl in an ethanol/water mixture to give 0.135 g (50%) of the expected product D (see Scheme 1).

m.p.: 213° C.

MS (ES$^+$), m/z=309

$^1$H NMR (CDCl$_3$, 400 MHz), 7.4 ppm (1H, d); 6.9 ppm (1H, d); 6.1 ppm (1H, t); 4.55 ppm (2H, q); 4.3 ppm (2H, d); 2.4 ppm (3H, s); 1.45 ppm (3H, t)

Example 10

Methyl 3-(1-ethyl-3-methyl-8-oxo-1,6,7,8-tetrahydro-pyrazolo[4,3-e][1,4]diazepin-5-yl) propanoate (R1=methyl; R2=ethyl; R3=methyl propanoate)

Step 7:

According to M8, 0.44 g (2.21 mmol) of 2-ethyl-5-methyl-4-nitro-2H-pyrazole-3-carboxylic acid is reacted with 0.41 g (1 eq.) of methyl 5-amino-4-oxopentanoate hydrochloride to give 0.63 g (87%) of an amide of type C (see scheme 1).

Rf (95/5 CH$_2$Cl$_2$/methanol)=0.48

$^1$H NMR (CDCl$_3$, 400 MHz), 7.7 ppm (1H, m); 4.4 ppm (2H, d); 4.3 ppm (2H, q); 3.7 ppm (3H, s); 2.85 ppm (2H, dd); 2.7 ppm (2H, dd); 2.5 ppm (3H, s); 1.5 ppm (3H, t)

Step 8:

According to M11, 0.6 g (1.83 mmol) of the amide C (see scheme 1) is refluxed with 1.1 g of iron and 0.18 ml of 36% HCl in an ethanol/water mixture to give 0.42 g (83%) of the expected product D (see scheme 1).

m.p.: 68° C.

$^1$H NMR (CDCl$_3$, 400 MHz), 6.7 ppm (1H, t); 4.5 ppm (2H, q); 3.8 ppm (3H, s); 3.55 ppm (2H, d), 2.85 ppm (2H, t), 2.7 ppm (2H, t), 2.2 ppm (3H, s); 1.45 ppm (3H, t)

Example 11

5-(4-Chlorophenyl)-1-ethyl-3-methyl-6,7-dihydro-1H-pyrazolo[4,3-e][1,4]diazepin-8-one R1=methyl; R2=ethyl; R3=4-chlorophenyl Step 7:

According to M8, 0.5 g (2.5 mmol) of 2-ethyl-5-methyl-4-nitro-2H-pyrazole-3-carboxylic acid is reacted with 0.517 g (1 eq.) of 2-amino-4'-chloroacetophenone hydrochloride to give 0.5 g (57%) of an amide of type C (see scheme 1) in which R1, R2 and R3 are as defined in this example. Rf (5/5 cyclohexane/EtoAc)=0.55

$^1$H NMR (CDCl$_3$, 400 MHz), 8.0 ppm (3H, d); 7.5 ppm (2H, d); 4.95 ppm (2H, d); 4.35 ppm (2H, q); 2.5 ppm (3H, s); 1.5 ppm (3H, t)

Step 8:

According to M11, 0.45 g (1.28 mmol) of the amide C (see scheme 1) is refluxed with 0.77 g of iron and 0.128 ml of 36% HCl in an ethanol/water mixture to give 0.27 g (70%) of the expected product D (see Scheme 1).

m.p.: 215° C.

MS (ES$^+$), m/z=303

$^1$H NMR (CDCl$_3$, 400 MHz), 7.9 ppm (2H, d); 7.5 ppm (2H, d); 6 ppm (1H, t); 4.5 ppm (2H, q); 4.1 ppm (2H, d); 2.4 ppm (3H, s); 1.45 ppm (3H, t)

Example 12

5-(4-Aminophenyl)-1-ethyl-3-methyl-6,7-dihydro-1H-pyrazolo-[4,3-e][1,4]diazepin-8-one (R1=methyl; R2=ethyl; R3=4-aminophenyl)

Step 7:

According to M8, 0.5 g (2.5 mmol) of 2-ethyl-5-methyl-4-nitro-2H-pyrazole-3-carboxylic acid is reacted with 0.540 g (1 eq.) of 2-amino-4'-nitroacetophenone hydrochloride to give 0.45 g (50%) of an amide of type C (see scheme 1).

Rf (EtOAc)=0.9

$^1$H NMR (CDCl$_3$, 400 MHz), 8.4 ppm (2H, d); 8.2 ppm (2H, d); 8.0 ppm (1H, m); 5.0 ppm (2H, d); 4.4 ppm (2H, q); 2.5 ppm (3H, s); 1.5 ppm (3H, t)

Step 8:

According to M11, 0.38 g (1.05 mmol) of the amide C (see scheme 1) is refluxed with 0.63 g of iron and 0.105 ml of 36% HCl in an ethanol/water mixture to give 0.12 g (40%) of the expected product D (see scheme 1).

m.p.: 212° C.

MS (ES$^+$), m/z=284

$^1$H NMR (DMSO, 400 MHz), 8.2 ppm (1H, t); 7.8 ppm (2H, d); 6.6 ppm (2H, d); 5.8 ppm (2H, s); 4.5 ppm (2H, q); 3.9 ppm (2H, d); 2.3 ppm (3H, s); 1.45 ppm (3H, t)

Example 13

1-Ethyl-5-(4-fluorophenyl)-3-methyl-6,7-dihydro-1H-pyrazolo[4,3-e][1,4]diazepin-8-one (R1=methyl; R2=ethyl; R3=4-fluorophenyl)

Step 7:

According to M8, 0.1 g (0.53 mmol) of 2-ethyl-5-methyl-4-nitro-2H-pyrazole-3-carboxylic acid is reacted with 0.1 g of 2-amino-4'-fluoroacetophenone hydrochloride to give 0.17 g (96%) of an amide of type C (see scheme 1).

Rf (5/5 cyclohexane/EtoAc)=0.45

$^1$H NMR (CDCl$_3$, 400 MHz), 8.0 ppm (2H, m); 7.9 ppm (1H, m); 7.15 ppm (2H, m); 4.95 ppm (2H, d); 4.3 ppm (2H, q); 2.5 ppm (3H, s); 1.5 ppm (3H, t)

Step 8:

According to M11, 0.16 g (0.48 mmol) of the amide C (see scheme 1) is refluxed with 0.287 g of iron and 0.048 ml of 36% HCl in an ethanol/water mixture to give 0.08 g of the expected product D (see scheme 1).

m.p.: 174° C.

MS (ES$^+$), m/z=287

$^1$H NMR (CDCl$_3$, 400 MHz) 8.0 ppm (2H, m); 7.15 ppm (2H, m), 6.7 ppm (1H, t); 4.5 ppm (2H, q); 4.1 ppm (2H, d); 2.4 ppm (3H, s); 1.5 ppm (3H, t)

Example 14

5-(3-Bromophenyl)-1-ethyl-3-methyl-6,7-dihydro-1H-pyrazolo-[4,3-e][1,4]diazepin-8-one (R1=methyl; R2=ethyl; R3=3-bromophenyl)

Step 7:

According to M8, 0.08 g (0.4 mmol) of 2-ethyl-5-methyl-4-nitro-2H-pyrazole-3-carboxylic acid is reacted with 0.1 g (1 eq.) of 2-amino-3'-bromoacetophenone hydrochloride to give 0.16 g (100%) of an amide of type C (see scheme 1).

Rf (98/2 CH$_2$Cl$_2$/MeOH)=0.29

$^1$H NMR (CDCl$_3$, 400 MHz), 8.15 ppm (1H, s); 7.9 ppm (2H, m); 7.8 ppm (1H, m); 7.4 ppm (1H, m); 5.0 ppm (2H, d); 4.3 ppm (2H, q); 2.6 ppm (3H, s); 1.5 ppm (3H, t)

Step 8:

According to M11, 0.16 g (0.4 mmol) of the amide C is refluxed with 0.24 g of iron and 0.04 ml of 36% HCl in an ethanol/water mixture to give 0.06 g (43%) of the expected product D (see scheme).

m.p.: 173° C.

MS (ES$^+$), m/z=348

$^1$H NMR (CDCl$_3$, 400 MHz), 8.1 ppm (1H, m); 7.9 ppm (1H, m), 7.6 ppm (1H, m), 7.4 ppm (1H, m), 7.25 ppm (1H, s), 6.3 ppm (1H, t); 4.6 ppm (2H, q); 4.1 ppm (2H, d); 2.4 ppm (3H, s); 1.5 ppm (3H, t)

Example 15

3-Methyl-5-phenyl-1-propyl-6,7-dihydro-1H-pyrazolo-[4,3-e][1,4]diazepin-8-one (R1=methyl; R2=propyl; R3=phenyl)

Step 7:

According to M8, 0.37 g (1.6 mmol) of 5-methyl-4-nitro-2-propyl-2H-pyrazole-3-carboxylic acid is reacted with 0.28 g (1.6 mmol) of 2-aminoacetophenone hydrochloride to give 0.54 g (96%) of an amide of type C (see scheme 1).

Rf (90/10) CH$_2$Cl$_2$/acetone)=0.7

$^1$H NMR (CDCl$_3$, 400 MHz), 8.0 ppm (2H, d); 7.85 ppm (1H, t); 7.65 ppm (1H, m); 7.55 ppm (2H, m); 5.0 ppm (2H, d); 4.25 ppm (2H, t); 2.55 ppm (3H, s); 1.9 ppm (2H, m); 0.9 ppm (3H, t)

Step 8:

According to M11, 0.138 g (0.42 mmol) of the amide C (see scheme 1) is refluxed with 0.28 g of iron and 0.05 ml of 36% HCl in an ethanol/water mixture to give 0.072 g (61%) of the expected product D (see scheme 1).

m.p.: 171° C.

MS (ES$^+$), m/z=283

$^1$H NMR (CDCl$_3$, 400 MHz), 8.0 ppm (2H, d); 7.55 ppm (3H, m); 6.65 ppm (1H, t); 4.5 ppm (2H, t); 4.15 ppm (2H, d); 2.4 ppm (3H, s); 1.9 ppm (2H, m); 0.9 ppm (3H, t)

Example 16

1-(2-Hydroxyethyl)-3-methyl-5-phenyl-6,7-dihydro-1H-pyrazolo[4,3-e][1,4]diazepin-8-one (R1=methyl; R2=2-hydroxyethyl; R3=phenyl)

Step 5:

6.3 g (33.8 mmol) of a pyrazole of type A4 (see scheme 1 and *J. Org. Chem.*, 21, 833–835, 1956; *Gazz. Chim. Ital.*, 75, 121–131, 1945) are reacted with 8.48 g (40.5 mmol) of 2-(2-bromoethoxy)tetrahydro-2H-pyran (commercial) to give 3.44 g (31%) of a pyrazole A5 (see scheme 1).

Rf (95/5 CH$_2$Cl$_2$/acetone)=0.47

$^1$H NMR (CDCl$_3$, 400 MHz), 4.55–4.35 ppm (5H, m); 4.0 ppm (1H, m); 3.7–3.4 ppm (3H, m); 2.5 ppm (3H, s); 1.8–1.55 ppm (6H, m); 1.5 ppm (3H, t)

Step 6:

1.1 g (3.4 mmol) of the pyrazole A5 (see scheme 1) are reacted with 0.2 g (5.1 mmol) of sodium hydroxide in a mixture of methanol and water to give 0.97 g (95%) of a pyrazole of type A (see scheme 1).

Rf (80/20 CH$_2$Cl$_2$/MeOH)=0.26

$^1$H NMR (CDCl$_3$, 400 MHz), 7.9 ppm (1H, s); 4.7–4.5 ppm (3H, m); 4.0 ppm (1H, m); 3.8–3.45 ppm (3H, m); 2.5 ppm 3H, s); 1.9–1.4 ppm (6H, m)

Step 7:

According to M8, 0.9 g (3 mmol) of 2-(2-hydroxyethyle)-5-methyl-4-nitro-2H-pyrazole-3-carboxylic acid is reacted with 0.52 g (3 mmol) of 2-aminoacetophenone hydrochloride to give 1.43 g (100%, crude) of an amide of type C (see scheme 1).

Rf (90/10 CH$_2$Cl$_2$/acetone)=0.51

$^1$H NMR (CDCl$_3$, 400 MHz), 8.3 ppm (1H, s); 8.0 ppm (2H, m); 7.6 ppm (1H, m); 7.5 ppm (2H, m); 4.7 ppm (1H, m); 4.5 ppm (2H, t); 4.1 ppm (1H, m); 3.85 ppm (1H, m); 3.7–3.4 ppm (2H, m); 2.55 ppm (3H, s); 1.9–1.4 ppm (6H, m)

Step 8:

According to M11, 1.4 g (3 mmol) of the amide C (see scheme 1) are refluxed with 1.8 g of iron and 0.31 ml of 36% HCl in a mixture of ethanol and water to give 0.09 g (11%) of the expected product D (see scheme 1).

m.p.: 75° C.

MS (ES$^+$), m/z=285

$^1$H NMR (CDCl$_3$, 400 MHz), 8.0 ppm (2H, m); 7.55 ppm (3H, m); 7.05 ppm (1H,t); 4.65 ppm (2H, t); 4.15 ppm (2H, d); 4.0 ppm (2H, m); 3.9 ppm (1H, OH); 2.4 ppm (3H, s).

Example 17

1-Ethyl-3-methyl-5-phenyl-6,7-dihydro-1H-pyrazolo[4,3-e][1,4]diazepin-8-thione (R1=methyl; R2=ethyl; R3=phenyl)

Step 9:

0.2 g (0.74 mmol) of a pyrazolodiazepine of type D (see scheme 1), in which R1, R2 and R3 are as defined in this example, is refluxed in toluene with 0.6 g (2 eq.) of Lawesson's reagent to give 188 mg (89%) of the expected product E (see scheme 1).

m.p.: 203.5° C.

MS (ES$^+$), m/z=285

$^1$H NMR (CDCl$_3$, 400 MHz), 8.0 ppm (2H, m); 7.8 ppm (1H, t), 7.5 ppm (3H, m); 4.8 ppm (2H, q); 4.25 ppm (2H, d); 2.5 ppm (3H, s); 1.6 ppm (3H, t)

Example 18

1-Ethyl-5-(3-methoxyphenyl)-3-methyl-6,7-dihydro-1H-pyrazolo[4,3-e][1,4]diazepin-8-one (R1=methyl; R2=ethyl; R3=3-methoxyphenyl)

Step 7:

According to M8, 0.5 g (2.51 mmol) of 2-ethyl-5-methyl-4-nitro-2H-pyrazole-3-carboxylic acid is reacted with 0.51 g (2.51 mmol) of 2-amino-3'-methoxyacetophenone hydrochloride (Patent, Brachwitz, Werner, DD65929, 1967) to give 0.8 g (92%) of an amide of type C (see scheme 1).

Rf (CH$_2$Cl$_2$/MeOH 90/10)=0.87

$^1$H NMR (CDCl$_3$, 400 MHz), 7.95 ppm (1H, s); 7.55 ppm (1H, m); 7.5 ppm (1H, m); 7.4 ppm (1H, m); 7.2 ppm (1H, m); 5.0 ppm (2H, d); 4.35 ppm (2H, q); 3.9 ppm (3H, s); 2.55 ppm (3H, s); 1.5 ppm (3H, t)

Step 8:

According to M11, 0.792 g (2.29 mmol) of the amide C (see scheme 1) is refluxed with 1.37 g of iron and 0.23 ml of 36% aqueous HCl in an ethanol/water mixture to give 0.312 g (46%) of the expected product D (see scheme 1).

m.p.: 120° C.

MS (ES$^+$), m/z=299

$^1$H NMR (CDCl$_3$, 400 MHz), 7.6–7.3 ppm (3H, m); 7.0 ppm (1H, m); 6.9 ppm (1H,s); 4.6 ppm (2H, q); 4.1 ppm (2H, d); 3.9 ppm (3H, s); 2.4 ppm (3H, s); 1.5 ppm (3H, t)

Example 19

5-(2-Aminophenyl)-1-ethyl-3-methyl-6,7-dihydro-1H-pyrazolo[4,3-e][1,4]diazepin-8-one (R1=methyl; R2=ethyl; R3=2-aminophenyl)

Step 7:

According to M8, 1.11 g (5.56 mmol) of 2-ethyl-5-methyl-4-nitro-2H-pyrazole-3-carboxylic acid are reacted with 0.5 g of 2-amino-2'-nitroacetophenone hydrochloride to give 0.246 g (44%) of an amide of type C (see scheme 1.

Rf (CH$_2$Cl$_2$/MeOH 90/10)=0.87

$^1$H NMR (CDCl$_3$, 400 MHz), 9.3 ppm (1H, s); 8.2 ppm (1H, m); 7.8 ppm (1H, m); 7.6–7.5 ppm (2H, m); 4.6 ppm (2H, d); 4.1 ppm (2H, q); 2.5 ppm (3H, s); 1.4 ppm (3H, t)

Step 8:

According to M11, 0.237 g (0.66 mmol) of the amide C (see scheme 1) is refluxed with 0.4 g of iron and 0.07 ml of 36% HCl in an ethanol/water mixture to give 0.08 g (43%) of the expected product D (see scheme 1).

m.p.: 156° C.

MS (ES$^+$), m/z=284

$^1$H NMR(CDCl$_3$, 400 MHz), 7.5 ppm (1H, m); 7.2 ppm (1H, m); 6.8–6.5 ppm (5H, m); 4.6 ppm (2H, q); 4.15 ppm (2H, d); 2.4 ppm (3H, s); 1.5 ppm (3H, t)

Example 20

1-Ethyl-5-(2-methoxyphenyl)-3-methyl-6,7-dihydro-1H-pyrazolo[4,3-e][1,4]diazepin-8-one (R1=methyl; R2=ethyl; R3=2-methoxyphenyl)

Step 7:

According to M8, 0.24 g (1.22 mmol) of 2-ethyl-5-methyl-4-nitro-2H-pyrazole-3-carboxylic acid is reacted with 0.245 g (1.22 mmol) of 2-amino-2'-methoxyacetophenone hydrochloride (J. Org. Chem., 37, 2494–2496, 1972) to give 0.197 g (47%) of an amide of type C (see scheme 1).

Rf (CH$_2$Cl$_2$/MeOH 95/5)=0.8

$^1$H NMR (CDCl$_3$, 400 MHz), 8.0 ppm (1H, m); 7.9 ppm (1H, CONH); 7.55 ppm (1H, m); 7.05 ppm (2H, m); 4.95 ppm (2H, d); 4.35 ppm (2H, q); 4.0 ppm (3H, s); 2.55 ppm (3H, s); 1.5 ppm (3H, t)

Step 8:

According to M8, 0.19 g (0.55 mmol) of the amide C (see scheme 1) is refluxed with 0.33 g of iron and 0.055 ml of 36% HCl in an ethanol/water mixture to give 0.07 g (43%) of the expected product D (see scheme 1).

m.p.: 214° C.

MS (ES$^+$), m/z: 299

$^1$H NMR (CDCl$_3$, 400 MHz), 7.75 ppm (1H, m); 7.4 ppm (1H, m); 7.1 ppm (1H, m); 7.0 ppm (1H, m); 6.45 ppm (1H,s); 4.6 ppm (2H, q); 4.0 ppm (2H, d); 3.9 ppm (3H, s); 2.4 ppm (3H, s); 1.5 ppm (3H, t)

Example 21

3-tert-Butyl-1-ethyl-5-phenyl-6,7-dihydro-1H-pyrazolo[4,3-e][1,4]diazepin-8-one (R1=tert-butyl; R2=ethyl; R3=phenyl)

Step 3:

According to M1, 9 g (46 mmol) of ethyl 5-tert-butyl-2H-pyrazole-3-carboxylate and 11.61 g of $NaNO_3$ are reacted in 90 ml of concentrated $H_2SO_4$ to give 4.5 g (41%, white powder) of a compound of type A4 (see scheme 1).

MS (ES−), m/z=240

Rf ($CH_2Cl_2$/acetone 90/10)=0.54

Step 5:

According to M5, 4.8 g (19.8 mmol) of compound A7 (see scheme 1) are reacted with 1.74 ml (22 mmol) of iodoethane to give 4 g of a compound of type A5 (see Scheme 1) (yellow oil, 75%).

MS (ES+), m/z=270

$^1$H NMR ($CDCl_3$, 400 MHz), 1.35 ppm (12H, m); 1.4 ppm (3H, t); 4.35 ppm (4H, q)

Step 6:

4 g (14.8 mmol) of compound A5 (see scheme 1) are reacted with 0.89 g (22 mmol) of sodium hydroxide dissolved in a methanol/water mixture to give 3.2 g of a compound of type A (see scheme 1)(white powder, 89%)

MS (ES−), m/z=240

$^1$H NMR (DMSO, 400 MHz), 1.05 ppm (9H, s); 1.1 ppm (3H, t); 4.05 ppm (2H, q); 14.4 ppm (1H, m)

Step 7:

According to M8, 1 g (4.1 mmol) of compound A (see scheme 1) is reacted with 0.7 g of 2-amino-acetophenone hydrochloride to give 1.3 g (88%) of a compound of type C (see scheme 1).

MS (ES+), m/z=359

$^1$H NMR ($CDCl_3$, 400 MHz) 1.45 ppm (9H, s); 1.5 ppm (3H, t); 4.2 ppm (2H, q); 4.95 ppm (2H, d); 7.4 ppm (1H, m); 7.55 ppm (2H, m); 7.65 ppm (1H, t); 8.0 ppm (2H, d)

Step 8:

According to M11, 1.3 g (3.6 mmol) of compound C (see scheme 1) are refluxed with 0.5 ml of HCl and 2.16 g of iron in an ethanol/water mixture to give 0.2 g (18%) of the expected product D (see scheme 1).

MS (ES+), m/z=311 m.p.=160° C.

$^1$H NMR ($CDCl_3$, 400 MHz), 1.5 ppm (12H, m); 4.1 ppm (2H, d); 4.55 ppm (2H, q); 6.7 ppm (1H, m); 7.45 ppm (3H, m); 8.0 ppm (2H, d)

Example 22

3-Methyl-5-phenyl-1-propyl-6,7-dihydro-1H-pyrazolo[4,3-e][1,4]diazepin-8-thione (R1=methyl; R2=propyl; R3=phenyl)

Step 9:

0.57 g (2 mmol) of 3-Methyl-5-phenyl-1-propyl-6,7-dihydro-1H-pyrazolo[4,3-e][1,4]diazepin-8-one is refluxed in toluene with 1.6 g (4 mmol) of Lawesson's reagent to give 0.58 g (97%) of a compound of type E (see scheme 1).

MS (ES+), m/z=299

$^1$H NMR ($CDCl_3$, 400 MHz) 0.9 ppm (3H, t); 1.95 ppm (2H, m); 2.4 ppm (3H, s); 4.2 ppm (2H, m); 4.75 ppm (2H, t); 7.4 ppm (3H, m); 7.95 ppm (2H, d); 8.65 ppm (1H, m)

m.p.: 156° C.

Example 23

1-Ethyl-3-methyl-5-p-tolyl-6,7-dihydro-1H-pyrazolo[4,3-e][1,4]diazepin-8-one (R1=methyl; R2=ethyl; R3=p-tolyl)

Step 7:

According to M8, 0.31 g (1.56 mmol) of 2-ethyl-5-methyl-4-nitro-2H-pyrazole-3-carboxylic acid is reacted with 0.29 g (1.56 mmol) of 2-amino-4'-methylacetophenone hydrochloride to give 0.5 g (98%) of an amide of type C (see scheme 1).

Rf ($CH_2Cl_2$/MeOH 90/10)=0.85

$^1$H NMR($CDCl_3$, 400 MHz), 7.9 ppm (3H, m); 7.3 ppm (2H, m); 4.95 ppm (2H, d); 4.35 ppm (2H, q); 2.55 ppm (3H, 9); 2.45 ppm (3H, s); 1.5 ppm (3H, t)

Step 8:

According to M11, 0.5 g (1.51 mmol) of the amide C (see scheme 1) is refluxed with 0.94 g of iron and 0.17 ml of 36% HCl in an ethanol/water mixture to give 0.15 g (34%) of the expected product D (see scheme 1).

m.p.: 185° C.

MS (ES+), m/z=283

$^1$H NMR ($CDCl_3$, 400 MHz), 7.9 ppm (2H, d); 7.25 ppm (2H, d); 6.5 ppm (1H, s); 4.6 ppm (2H, q); 4.1 ppm (2H, d); 2.4 ppm (6H, s); 1.5 ppm (3H, t)

Example 24

5-(3-Aminophenyl)-1-ethyl-3-methyl-6,7-dihydro-1H-pyrazolo[4,3-e][1,4]diazepin-8-one (R1=methyl; R2=ethyl; R3=3-aminophenyl)

Step 7:

According to M8, 0.92 g (4.62 mmol) of 2-ethyl-5-methyl-4-nitro-2H-pyrazole-3-carboxylic acid is reacted with 1 g (4.62 mmol) of 2-amino-3'-nitroacetophenone hydrochloride to give 1.3 g (78%) of an amide of type C (see scheme 1).

Rf ($CH_2Cl_2$/MeOH 90/10)=0.89

$^1$H NMR ($CDCl_3$, 400 MHz), 9.1 ppm (1H, s); 8.8 ppm (1H, s); 8.4 ppm (1H, m); 8.5 ppm (1H, m); 7.8 ppm (1H, m); 4.95 ppm (2H, d); 4.3 ppm (2H, q); 2.5 ppm (3H, s); 1.5 ppm (3H, t)

Step 8:

According to M11, 1.3 g (3.6 mmol) of the amide C (see scheme 1) are refluxed with 2.15 g of iron and 0.38 ml of 36% HCl in an ethanol/water mixture to give 0.34 g (34%) of the expected product D (see scheme 1).

m.p.: 80° C.

MS (ES+), m/z=284

$^1$H NMR ($CDCl_3$, 400 MHz), 7.35 ppm (1H, m); 7.2 ppm (2H, m); 6.8 ppm (2H,m); 4.6 ppm (2H, q); 4.05 ppm (2H, d); 3.8 ppm (2H, bs); 2.4 ppm (3H, s); 1.5 ppm (3H, t)

Example 25

3-tert-Butyl-1-ethyl-5-phenyl-6,7-dihydro-1H-pyrazolo[4,3-e][1,4]diazepin-8-thione (R1=tert-butyl; R2=ethyl; R3=phenyl)

Step 9:

0.37 g (2.2 mmol) of 3-tert-butyl-1-ethyl-5-phenyl-6,7-dihydro-1H-pyrazolo[4,3-e][1,4]diazepin-8-one is reacted with 0.96 g (4.4 mmol) of Lawesson's reagent to give 0.25 g of a yellow powder (66%).

MS (ES+), m/z=327 m.p.=230° C.

$^1$H NMR ($CDCl_3$, 400 MHz) 1.45 ppm (9H, s); 1.5 ppm (3H, m); 4.2 ppm (2H, m); 4.8 ppm (2H, q); 7.45 ppm (3H, m); 8.0 ppm (2H, d); 8.55 ppm (1H, m).

Example 26

5-(4-Aminophenyl)-3-tert-butyl-1-ethyl-6,7-dihydro-1H-pyrazolo[4,3-e][1,4]diazepin-8-one (R1=tert-butyl; R2=ethyl; R3=4-aminophenyl)
Step 7:
According to M8, 1.2 g (4.9 mmol) of 5-tert-butyl-2-ethyl-4-nitro-2H-pyrazole-3-carboxylic acid are reacted with 1.06 g of 2-amino-4'-nitroacetophenone hydrochloride to give 1.15 g (58%) of an amide of type C (see scheme 1).
MS (ES–), m/z=402
$^1$H NMR (CDCl$_3$, 400 MHz), 1.4 ppm (9H, s); 1.5 ppm (3H, t); 4.25 ppm (2H, q); 4.95 ppm (2H, d); 7.4 ppm (1H, m); 8.15 ppm (2H, d); 8.35 ppm (2H, d)
Step 8:
According to M11, 1.15 g (2.8 mmol) of the amide C (see scheme 1) are refluxed with 0.5 ml of HCl and 1.7 g of iron in an ethanol/water mixture to give 0.43 g (48%) of the expected compound D (see scheme 1).
MS (ES+), m/z=326
m.p.=189° C.
$^1$H NMR (CDCl$_3$, 400 MHz), 1.45 ppm (12H, m); 3.95 ppm (2H, s); 4.05 ppm (2H, d); 4.5 ppm (2H, q); 6.2 ppm (1H, m); 6.65 ppm (2H, d); 7.8 ppm (2H, d)

Example 27

5-(4-Aminophenyl)-1-ethyl-3-isopropyl-6,7-dihydro-1H-pyrazolo[4,3-e][1,4]diazepin-8-one (R1=isopropyl; R2=ethyl; R3=4-aminophenyl)
Step 7:
According to M8, 1.3 g (4.9 mmol) of 2-ethyl-5-isopropyl-4-nitro-2H-pyrazole-3-carboxylic acid are reacted with 1.23 g of 2-amino-4'-nitro-acetophenone hydrochloride to give 2 g (90%) of the amide of type C (see scheme 1).
MS (ES–), m/z=388
$^1$H NMR (CDCl$_3$, 400 MHz), 1.3 ppm (9H, s); 1.5 ppm (3H, t); 3.55 ppm (1H, q); 4.3 ppm (2H, q); 5 ppm (2H, d); 7.8 ppm (1H, m); 8.15 ppm (2H, d); 8.4 ppm (2H, d)
Step 8:
According to M11, 2 g (5.1 mmol) of the amide C (see scheme 1) are refluxed with 0.5 ml of HCl and 3.07 g of iron in an ethanol/water mixture to give 0.5 g (31%) of the compound of type D (see scheme 1).
MS (ES+), m/z=312
m.p.=191° C.
$^1$H NMR (DMSO, 400 MHz), 1.15 ppm (6H, m); 1.25 ppm (3H, m); 3.05 ppm (1H, q); 3.8 ppm (2H, d); 4.3 ppm (2H, q); 5.65 ppm (2H, m); 6.5 ppm (2H, d); 7.6 ppm (2H, d); 8 ppm (1H, m)

Example 28

1-Ethyl-5-(4-hydroxyphenyl)-3-methyl-6,7-dihydro-1H-pyrazolo[4,3-e][1,4]diazepin-8-one (R1=methyl; R2=ethyl; R3=4-hydroxyphenyl)
17 ml of a molar solution of BBr$_3$ in dichloromethane are added dropwise to a solution of 0.2 g of 1-ethyl-5-(4-methoxyphenyl)-3-methyl-6,7-dihydro-1H-pyrazolo[4,3-e][1,4]diazepin-8-one in 84 ml of dichloromethane. The resulting mixture is refluxed for 6 hours. After cooling to RT, the reaction medium is neutralized with sodium bicarbonate solution. The organic phase is dried and evaporated. The product is purified by flash chromatography (gradient: CH$_2$Cl$_2$, 90/10 CH$_2$Cl$_2$/acetone, 80/20 CH$_2$Cl$_2$/acetone). Evaporation of the solvent gives 0.103 g of compound D in the form of a beige powder (54%).
Rf (90/10 CH$_2$Cl$_2$/MeOH)=0.25
$^1$H NMR (DMSO, 400 MHz), 9.5 ppm (1H, OH); 7.9 ppm (2H, m); 7.8 ppm (1H, bs); 6.9 ppm (2H, m); 4.5 ppm (2H, q); 4 ppm (2H, d); 2.4 ppm (3H, s); 1.5 ppm (3H, t)
MS (ES+) m/z=285
m.p.=250° C.

Example 29

5-(4-Aminophenyl)-3-methyl-1-propyl-6,7-dihydro-1H-pyrazolo[4,3-e][1,4]diazepin-8-one (R1=methyl; R2=propyl; R3=4-aminophenyl)
Step 7:
According to M8, 1.5 g (7 mmol) of 5-methyl-4-nitro-2-propyl-2H-pyrazole-3-carboxylic acid (A) are reacted with 1.52 g (7 mmol) of 2-amino-4'-nitro-acetophenone hydrochloride to give 2.5 g (95%) of an amide of type C (see scheme 1).
Rf (5/5 cyclohexane/ethyl acetate)=0.5
$^1$H NMR (CDCl$_3$, 400 MHz), 8.4 ppm (2H, d); 8.2 ppm (2H, d); 8 ppm (1H, m); 5 ppm (2H, d); 4.25 ppm (2H, t); 2.55 ppm (3H, s); 1.9 ppm (2H, m); 0.95 ppm (3H, t)
Step 8:
According to M11, 2.5 g (6.7 mmol) of the amide C (see scheme 1) are refluxed with 4.1 g of iron and 0.83 ml of 36% HCl in an ethanol/water mixture to give 0.75 g (40%) of the expected product D (see scheme 1).
m.p.: 225° C.
MS (ES+), m/z=298
$^1$H NMR (CDCl$_3$, 400 MHz), 7.9 ppm (1H, m); 7.8 ppm (2H, d); 6.7 ppm (2H, d); 4.9 ppm (2H, s); 4.45 ppm (2H, t); 4 ppm (2H, d); 2.35 ppm (3H, s); 1.85 ppm (2H, m); 0.9 ppm (3H, t)

Example 30

3-Methyl-5-phenyl-1-(2.2.2-trifluoroethyl)-6,7-dihydro-1H-pyrazolo[4,3-e][1,4]diazepin-8-one (R1=methyl; R2=2,2,2-trifluoroethyl; R3=phenyl)
Step 7:
According to M8, 0.8 g (3.2 mmol) of 5-methyl-4-nitro-2-(2,2,2-trifluoroethyl)-2H-pyrazole-3-carboxylic acid (A) is reacted with 0.54 g (3.2 mmol) of 2-aminoacetophenone hydrochloride to give 0.14 g (12%) of an amide of type C (see scheme 1).
Rf (cyclohexane/EtOAc 5/5)=0.76
MS (ES+), m/z=371
$^1$H NMR (CDCl$_3$, 400 MHz), 8.5 ppm (1H, s); 8.0 ppm (2H, d); 7.7 ppm (1H, m); 7.55 ppm (2H, m); 5.2 ppm (2H, m); 5.0 ppm (2H, d); 2.6 ppm (3H, s)
Step 8:
According to M11, 0.14 g (0.38 mmol) of the amide C (see scheme 1) is refluxed with 0.23 g of iron and 0.046 ml of 36% HCl in an ethanol/water mixture to give 0.1 g (80.5%) of the expected product D (see scheme 1).
MS (ES+), m/z=323
$^1$H NMR (CDCl$_3$, 400 MHz), 9.0 ppm (2H, m); 7.5 ppm (3H, m); 6.6 ppm (1H, t); 5.3 ppm (2H, m); 4.2 ppm (2H, d); 2.5 ppm (3H, s)

Example 31

5-Cyclohexyl-1-ethyl-3-methyl-6,7-dihydro-1H-pyrazolo[4,3-e][1,4]diazepin-8-one (R1=methyl; R2=ethyl; R3=cyclohexyl)
Synthesis of the α-amino ketone:
According to M6, 2.7 g (13.2 mmol) of 2-bromo-1-cyclohexylethanone (*Tetrahedron*, 48, 1, 67–78, 1992) are mixed with 1.92 g (13.7 mmol) of hexamethylenetetramine in 20 ml of chloroform. The mixture is heated at 48° C. for 4 hours and then evaporated to dryness. The residue is taken up in 20 ml of ethanol and 9 ml of 36% hydrochloric acid. After leaving overnight at room temperature, the reaction medium is filtered. The filtrate is evaporated to dryness to give an oil which is crystallized from diethyl ether. After filtration and drying, 2.08 g (80%) of 2-amino-1-cyclohexylethanone hydrochloride are obtained in the form of a paste.

MS (ES+), m/z=141
Rf (80/20 $CH_2Cl_2$/MeOH): 0.31

Step 7:

According to M8, 1.8 g (8.9 mmol) of 2-ethyl-5-methyl-4-nitro-2H-pyrazole-3-carboxylic acid (A) are reacted with 1.6 g (8.9 mmol) of 2-amino-1-cyclohexylethanone hydrochloride to give 1.15 g (40%) of an amide of type C (see scheme 1).

Rf ($CH_2Cl_2$/MeOH 95/5)=0.48
$^1$H NMR ($CDCl_3$, 400 MHz), 7.6 ppm (1H, bs); 4.4 ppm (2H, d); 4.3 ppm (2H, q); 2.5 ppm (3H, s); 2.4 ppm (1H, m); 2.0 to 1.3 ppm (13H, m)

Step 8:

According to M11, 0.65 g (2 mmol) of the amide C (see scheme 1) is refluxed with 1.2 g of iron and 0.2 ml of 36% HCl in an ethanol/water mixture to give 0.35 g (64%) of the expected product D (see scheme 1).

m.p.: 50° C.
MS (ES+), m/z=275
$^1$H NMR ($C_6D_6$, 400 MHz), 6.6 ppm (1H, t); 4.6 ppm (2H, q); 3.6 ppm (2H, d); 2.5 ppm (1H, td); 2.4 ppm (3H, s); 1.9 to 1.3 ppm (1OH, m); 1.5 ppm (3H, t)

Example 32

1-Ethyl-3-methyl-5-pyrid-4-yl-6,7-dihydro-1H-pyrazolo[4,3-e][1,4]diazepin-8-one (R1=methyl; R2=ethyl; R3=4-pyridyl)

Step 7:

According to M8, 1.24 g (6.2 mmol) of 2-ethyl-5-methyl-4-nitro-2H-pyrazole-3-carboxylic acid (A) are reacted with 1.3 g (6.2 mmol) of 2-amino-1-pyrid-4-yl-ethanone hydrochloride (J. Med. Chem., 38, 17, 3342–3350, 1995; J. Amer. Chem. Soc., 67, 1468–1472, 1945) to give 0.77 g (39%) of an amide of type C (see scheme 1).

Rf (80/20 $CH_2Cl_2$/acetone)=0.39
$^1$H NMR (DMSO, 400 MHz), 9.4 ppm (1H, t); 8.7 ppm (2H, d); 7.8 ppm (2H, d); 4.8 ppm (2H, d); 4.1 ppm (2H, q); 2.3 ppm (3H, s); 1.2 ppm (3H, t)

Step 8:

According to M11, 0.76 g (2.4 mmol) of the amide C (see scheme 1) is refluxed with 1.43 g of iron and 0.24 ml of 36% HCl in an ethanol/water mixture to give 0.1 g (15%) of the expected product D (see scheme 1).

m.p.: 148° C.
MS (ES+), m/z=270
$^1$H NMR ($CDCl_3$, 400 MHz), 8.8 ppm (2H, d); 8.3 ppm (1H, t); 7.9 ppm (2H, d); 4.4 ppm (2H, q); 4.1 ppm (2H, d); 2.3 ppm (3H, s); 1.4 ppm (3H, t)

Example 33

5-tert-Butyl-1-ethyl-3-methyl-6,7-dihydro-1H-pyrazolo[4,3-e][1,4]diazepin-8-one (R1=methyl; R2=ethyl; R3=tert-butyl)

Step 7:

According to M8, 0.66 g (3.3 mmol) of 2-ethyl-5-methyl-4-nitro-2H-pyrazole-3-carboxylic acid (A) is reacted with 0.5 g (3.3 mmol) of 1-amino-3,3-dimethyl-butan-2-one hydrochloride (J. Org. Chem., 53, 5, 1113–1114, 1988) to give 0.72 g (73.5%) of an amide of type C (see scheme 1).

Rf (90/10 $CH_2Cl_2$/MeOH)=0.88
$^1$H NMR ($CDCl_3$, 400 MHz), 7.6 ppm (1H, bs); 4.5 ppm (2H, d); 4.3 ppm (2H, q); 2.6 ppm (3H, s); 1.5 ppm (3H, t); 1.3 ppm (9H, s)

Step 8:

According to M11, 0.71 g (2.4 mmol) of the amide C (see scheme 1) is refluxed with 1.43 g of iron and 0.24 ml of 36% HCl in an ethanol/water mixture to give 0.27 g (46%) of the expected product D (see scheme 1).

m.p.: 120° C.
MS (ES+), m/z=249
$^1$H NMR ($CDCl_3$, 400 MHz), 6.6 ppm (1H, t); 4.5 ppm (2H, q); 3.7 ppm (2H, d); 2.3 ppm (3H, s); 1.4 ppm (3H, t); 1.2 ppm (9H, s)

Example 34

3-Butyl-1-ethyl-5-phenyl-6,7-dihydro-1H-pyrazolo[4,3-e][1,4]diazepin-8-one (R1=butyl; R2=ethyl; R3=phenyl)

Step 7:

According to M8, 1 g (4.1 mmol) of 5-butyl-2-ethyl-4-nitro-2H-pyrazole-3-carboxylic acid (A) is reacted with 0.7 g (4.1 mmol) of 2-aminoacetophenone hydrochloride to give 1.25 g (86%) of an amide of type C (see scheme 1).

MS (ES+), m/z=359
$^1$H NMR ($CDCl_3$, 400 MHz), 8.0 ppm (2H, d); 7.8 ppm (1H, bs); 7.7 ppm (1H, m); 7.5 ppm (2H, m); 5.0 ppm (2H, d); 4.3 ppm (2H, q); 3.0 ppm (2H, m); 1.7 ppm (2H, m); 1.5 ppm (5H, m); 1.0 ppm (3H, t)

Step 8:

According to M11, 1.25 g (3.5 mmol) of the amide C (see scheme 1) are refluxed with 2.1 g of iron and 0.5 ml of 36% HCl in an ethanol/water mixture to give the expected product D (see scheme 1).

m.p.: 105.4° C.
MS (ES+), m/z=311
$^1$H NMR ($CDCl_3$, 400 MHz), 8.0 ppm (2H, m); 7.5 ppm (3H, m); 4.6 ppm (2H, q); 4.1 ppm (2H, d); 2.8 ppm (2H, m); 1.9 to 1.2 ppm (7H, m); 1.0 ppm (3H, t)

Example 35

5-tert-Butyl-1-ethyl-3-isopropyl-6,7-dihydro-1H-pyrazolo[4,3-e][1,4]diazepin-8-one (R1=isopropyl; R2=ethyl; R3=tert-butyl)

Step 7:

According to M9, 0.4 g (1.76 mmol) of 2-ethyl-5-isopropyl-4-nitro-2H-pyrazole-3-carboxylic acid (A) is reacted with 0.266 g (1.76 mmol) of 1-amino-3,3-dimethylbutan-2-one hydrochloride (J. Org. Chem., 53, 5, 1113–1114, 1988) to give 0.38 g (67%) of an amide of type C (see scheme 1).

MS (ES+), m/z=325

Step 8:

According to M12, 0.38 g (1.17 mmol) of the amide C (see scheme 1) is refluxed in ethanol with 1.32 g (5 eq.) of tin chloride dihydrate to give 0.22 g (68%) of the expected product D (see scheme 1).

MS (ES+), m/z=277
$^1$H NMR (DMSO, 400 MHz), 8.2 ppm (1H, t); 4.4 ppm (2H, q); 3.6 ppm (2H, d); 3.1 ppm (1H, m); 1.3 ppm (3H, t); 1.25 ppm (6H, d); 1.2 ppm (9H, s)

Example 36

1-Ethyl-3-isopropyl-5-p-tolyl-6,7-dihydro-1H-pyrazolo[4,3-e][1,4]diazepin-8-one (R1=isopropyl; R2=ethyl; R3=p-tolyl)

Step 7:

According to M9, 0.4 g (1.76 mmol) of 2-ethyl-5-isopropyl-4-nitro-2H-pyrazole-3-carboxylic acid (A) is reacted with 0.327 g (1.76 mmol) of 2-amino-1-p-tolylethanone hydrochloride to give 0.32 g (51%) of an amide of type C (see scheme 1).

MS (ES+), m/z=359

$^1$H NMR (CDCl$_3$, 400 MHz), 7.9 ppm (2H, d); 7.7 ppm (1H, bs); 7.3 ppm (2H, d); 5.0 ppm (2H, d); 4.3 ppm (2H, q); 3.6 ppm (1H, m); 2.4 ppm (3H, s); 1.5 ppm (3H, t); 1.3 ppm (6H, d)

Step 8:

According to M12, 0.32 g (1.17 mmol) of the amide C (see scheme 1) is refluxed in ethanol with 1.01 g of tin chloride dihydrate to give 0.13 g (47%) of the expected product D (see scheme 1).

MS (ES+), m/z=311

$^1$H NMR (DMSO, 400 MHz), 8.2 ppm (1H, t); 7.9 ppm (2H, d); 7.3 ppm (2H, d); 4.4 ppm (2H, q); 4.0 ppm (2H, d); 3.2 ppm (1H, m); 2.3 ppm (3H, s); 1.3 ppm (3H, t); 1.2 ppm (6H, d)

Example 37

4-(1-Ethyl-3-isopropyl-8-oxo-1,6,7,8-tetrahydro-pyrazolo[4,3-e][1,4]diazepin-5-yl)benzonitrile (R1=isopropyl; R2=ethyl; R3=4-cyanophenyl)

Step 7:

According to M9, 0.4 g (1.76 mmol) of 2-ethyl-5-isopropyl-4-nitro-2H-pyrazole-3-carboxylic acid (A) is reacted with 0.346 g (1.76 mmol) of 4-(2-aminoethanoyl)benzonitrile hydrochloride (*Yakugaku Zasshi*, 72, 305–307, 1952) to give 0.27 g (41%) of an amide of type C (see scheme 1).

MS (ES−), m/z=368

$^1$H NMR (CDCl$_3$, 400 MHz), 8.1 ppm (2H, d); 7.8 ppm (2H, d); 7.75 ppm (1H, bs); 5.0 ppm (2H, d); 4.3 ppm (2H, m); 3.5 ppm (1H, m); 1.5 ppm (3H, m); 1.3 ppm (6H, m)

Step 8:

According to M12, 0.27 g (0.7 mmol) of the amide C (see scheme 1) is refluxed in ethanol with 0.82 g of tin chloride dihydrate to give 0.077 g (33%) of the expected product D (see scheme 1)

MS (ES+), m/z=322

$^1$H NMR (CDCl$_3$, 400 MHz), 8.3 ppm (1H, t); 8.2 ppm (2H, m); 8.0 ppm (2H, m); 4.45 ppm (2H, q); 4.05 ppm (2H, m); 3.2 ppm (1H, m); 1.4 ppm (3H, t); 1.3 ppm (6H, d)

Example 38

1-Ethyl-3-isopropyl-5-(4-pyrrolidin-1-yl-phenyl)-6,7-dihydro-1H-pyrazolo[4,3-e][1,4]diazepin-8-one, (R1=isopropyl; R2=ethyl; R3=4-(1-pyrrolidyl)phenyl Synthesis of the α-amino ketone B with R3=4-(1-pyrrolidinyl)phenyl:

According to M6, 16.1 g (60 mmol) of 2-bromo-1-(4-(1-pyrrolidinyl)phenyl)ethanone are mixed with 8.75 g (62.4 mmol) of hexamethylenetetramine in 240 ml of chloroform. The mixture is heated at 48° C. for 4 hours and then filtered at room temperature. The precipitate is taken up in 88 ml of ethanol and 44 ml of 36% hydrochloric acid. After stirring overnight at room temperature, the reaction medium is filtered. The filtrate is evaporated to dryness to give an oil which is crystallized from ethanol. After filtration, washing of the precipitate with 20 ml of water and drying, 6.3 g (43%) of 2-amino-1-(4-(1-pyrrolidine)phenyl)-ethanone hydrochloride are obtained in the form of a beige powder containing 3% by weight of NH$_4$Cl.

$^1$H NMR (DMSO, 400 MHz), 8.1 ppm (3H, s); 7.65 ppm (2H, d); 6.45 ppm (2H, d); 4.2 ppm (2H, m); 3.2 ppm (4H, m); 1.8 ppm (4H, t)

Step 7:

According to M9, 0.4 g (1.76 mmol) of 2-ethyl-5-isopropyl-4-nitro-2H-pyrazole-3-carboxylic acid (A) is reacted with 0.437 g (1.76 mmol) of 2-amino-1-(4-(1-pyrrolidine)phenyl)-ethanone hydrochloride (97%) to give 0.36 g (49%) of an amide of type C (see scheme 1).

MS (ES+), m/z=414

Step 8:

According to M12, 0.36 g (0.87 mmol) of the amide C (see scheme 1) is refluxed in ethanol with 0.98 g (5 eq.) of tin chloride dihydrate to give 0.143 g (45%) of the expected product D (see scheme 1).

MS (ES+), m/z=366

$^1$H NMR (DMSO, 400 MHz), 8.2 ppm (1H, t); 7.9 ppm (2H, d); 6.6 ppm (2H, d); 4.4 ppm (2H, q); 3.95 ppm (2H, d); 3.3 ppm (4H, m); 3.2 ppm (1H, m); 2 ppm (4H, m); 1.35 ppm (3H, t); 1.3 ppm (6H, d)

Example 39

5-(2,4-Dimethoxyphenyl)-1-ethyl-3-isopropyl-6,7-dihydro-1H-pyrazolo[4,3-e][1,4]diazepin-8-one (R1=isopropyl; R2=ethyl; R3=2,4-dimethoxyphenyl)

Step 7:

According to M9, 0.4 g (1.76 mmol) of 2-ethyl-5-isopropyl-4-nitro-2H-pyrazole-3-carboxylic acid (A) is reacted with 0.408 g (1.76 mmol) of 2-amino-1-(2,4-dimethoxyphenyl)-ethanone hydrochloride to give 0.47 g (66%) of an amide of type C (see scheme 1).

MS (ES+), m/z=40

Step 8:

According to M12, 0.47 g (1.16 mmol) of the amide C (see scheme 1) is refluxed in ethanol with 1.31 g of tin chloride dihydrate to give 0.152 g (37%) of the expected product D (see scheme 1).

MS (ES+), m/z=357

$^1$H NMR (DMSO, 400 MHz), 8.3 ppm (1H, t); 7.6 ppm (1H, d); 6.7 ppm (2H, m); 4.45 ppm (2H, q); 3.9 ppm (3H, s); 3.85 ppm (2H,d); 3.8 ppm (3H, s); 3.2 ppm (1H, m); 1.4 ppm (3H, t); 1.2 ppm (6H, d)

Example 40

5-tert-Butyl-3-isopropyl-1-propyl-6,7-dihydro-1H-pyrazolo[4,3-e][1,4]diazepin-8-one (R1=isopropyl; R2=propyl; R3=tert-butyl)

Step 7:

According to M9, 0.425 g (1.76 mmol) of 5-isopropyl-4-nitro-2-propyl-2H-pyrazole-3-carboxylic acid (A) is reacted with 0.267 g (1.76 mmol) of 1-amino-3,3-dimethylbutan-2-one hydrochloride (*J. Org. Chem.*, 53, 5, 1113–1114, 1988) to give 0.43 g (72%) of an amide of type C (see Scheme 1).

MS (ES+), m/z=33

Step 8:

According to M12, 0.43 g (1.27 mmol) of the amide C (see scheme 1) is refluxed in ethanol with 1.43 g of tin chloride dihydrate to give 0.236 g (64%) of the expected product D (see Scheme 1).

MS (ES+), m/z=291

¹H NMR (DMSO, 400 MHz), 8.25 ppm (1H, bs); 4.4 ppm (2H, bs); 3.6 ppm (2H, s); 3.2 ppm (1H, m); 1.8 ppm (2H, m); 1.3 ppm (6H, d); 1.25 ppm (9H, s); 0.85 ppm (3H, t)

Example 41

3-Isopropyl-1-propyl-5-p-tolyl-6,7-dihydro-1H-pyrazolo[4,3-e][1,4]diazepin-8-one (R1=isopropyl; R2=propyl; R3=p-tolyl)
Step 7:
According to M9, 0.425 g (1.76 mmol) of 5-isopropyl-4-nitro-2-propyl-2H-pyrazole-3-carboxylic acid (A) is reacted with 0.327 g (1.76 mmol) of 2-amino-1-p-tolylethanone hydrochloride to give 0.37 g (57%) of an amide of type C (see scheme 1).
MS (ES+), m/z=373
Step 8:
According to M12, 0.37 g (1 mmol) of the amide C (see scheme 1) is refluxed in ethanol with 1.12 g of tin chloride dihydrate to give 0.176 g (55%) of the expected product D (see scheme 1).
MS (ES+), m/z=325
¹H NMR (DMSO, 400 MHz), 8.1 ppm (1H, t); 7.7 ppm (2H, d); 7.1 ppm (2H, d); 4.25 ppm (2H, t); 3.8 ppm (2H, d); 3.1 ppm (1H, m); 2.2 ppm (3H, s); 1.6 ppm (2H, m); 1.1 ppm (6H, d); 0.7 ppm (3H, t)

Example 42

4-(3-Isopropyl-8-oxo-1-propyl-1,6,7,8-tetrahydro-pyrazolo[4,3-e][1,4]diazepin-5-yl)benzonitrile (R1=isopropyl; R2=propyl; R3=4-cyanophenyl)
Step 7:
According to M9, 0.425 g (1.76 mmol) of 5-isopropyl-4-nitro-2-propyl-2H-pyrazole-3-carboxylic acid (A) is reacted with 0.346 g (1.76 mmol) of 4-(2-aminoethanoyl)benzonitrile hydrochloride (*Yakugaku Zasshi*, 72, 305–307, 1952) to give 0.32 g (48%) of an amide of type C (see Scheme 1).
MS (ES+), m/z=384
¹H NMR (CDCl₃, 400 MHz), 8.1 ppm (2H, d); 7.85 ppm (2H, d); 7.7 ppm (1H, bs); 5.0 ppm (2H, d); 4.3 ppm (2H, m); 3.6 ppm (1H, m); 1.9 ppm (2H, m); 1.3 ppm (6H, d); 0.9 ppm (3H, m)
Step 8:
According to M12, 0.32 g (0.834 mmol) of the amide C (see scheme 1) is refluxed in ethanol with 0.94 g of tin chloride to give 0.076 g (27%) of the expected product D (see Scheme 1).
MS (ES+), m/z=336
¹H NMR (DMSO, 400 MHz), 8.3 ppm (1H, bs); 8.15 ppm (2H, m); 8.0 ppm (2H, m); 4.4 ppm (2H, q); 4.05 ppm (2H, m); 3.2 ppm (1H, m); 1.8 ppm (2H, m); 1.3 ppm (6H, d); 0.9 ppm (3H, t)

Example 43

5-(2,4-Dimethoxyphenyl)-3-isopropyl-1-propyl-6,7-dihydro-1H-pyrazolo[4,3-e][1,4]diazepin-8-one (R1=isopropyl; R2=propyl; R3=2,4-dimethoxyphenyl)
Step 7:
According to M9, 0.425 g (1.76 mmol) of 5-isopropyl-4-nitro-2-propyl-2H-pyrazole-3-carboxylic acid (A) is reacted with 0.407 g (1.76 mmol) of 2-amino-1-(2,4-dimethoxy-phenyl)ethanone hydrochloride to give 0.54 g (73%) of an amide of type C (see Scheme 1).
MS (ES+), m/z=41
Step 8:
According to M12, 0.54 g (1.29 mmol) of the amide C (see scheme 1) is refluxed in ethanol with 1.46 g (5 eq.) of tin chloride dihydrate to give 0.246 g (51%) of the expected product D (see Scheme 1).
MS (ES+), m/z=371
¹H NMR (DMSO, 400 MHz), 8.3 ppm (1H, bs); 7.55 ppm (1H, m); 6.7 ppm (2H, m); 4.4 ppm (2H, t); 3.9 ppm (3H, s); 3.8 ppm (5H, m); 3.2 ppm (1H, m); 1.8 ppm (2H, m); 1.3 ppm (6H, m); 0.8 ppm (3H, m)

Example 44

3,5-Di-tert-butyl-1-ethyl-6,7-dihydro-1H-pyrazolo[4,3-e][1,4]diazepin-8-one (R1=tert-butyl; R2=ethyl; R3=tert-butyl)
Step 7:
According to M9, 0.425 g (1.76 mmol) of 5-tert-butyl-2-ethyl-4-nitro-2H-pyrazole-3-carboxylic acid (A) is reacted with 0.267 g (1.76 mmol) of 1-amino-3,3-dimethylbutan-2-one hydrochloride to give 0.37 g (62%) of an amide of type C (see Scheme 1).
MS (ES+), m/z=339
Step 8:
According to M12, 0.37 g (1.09 mmol) of the amide C (see scheme 1) is refluxed in ethanol with 1.23 g of tin chloride dihydrate to give 0.17 g (54%) of the expected product D (see Scheme 1).
MS (ES+), m/z=291
¹H NMR (DMSO, 400 MHz), 8.2 ppm (1H, t); 4.4 ppm (2H, q); 3.5 ppm (2H, d); 1.35 ppm (9H, s); 1.3 ppm (3H, t); 1.2 ppm (9H, s)

Example 45

3-tert-Butyl-1-ethyl-5-p-tolyl-6,7-dihydro-1H-pyrazolo[4,3-e][1,4]diazepin-8-one (R1=tert-butyl; R2=ethyl; R3=p-tolyl)
Step 7:
According to M9, 0.425 g (1.76 mmol) of 5-tert-butyl-2-ethyl-4-nitro-2H-pyrazole-3-carboxylic acid (A) is reacted with 0.327 g (1.76 mmol) of 2-amino-1-p-tolylethanone hydrochloride to give 0.39 g (60%) of an amide of type C (see Scheme 1).
MS (ES+), m/z=373
Step 8:
According to M12, 0.39 g (1.05 mmol) of the amide C (see scheme 1) is refluxed in ethanol with 1.18 g of tin chloride dihydrate to give 0.181 g (53%) of the expected product D (see Scheme 1).
MS (ES+), m/z=325
¹H NMR (DMSO, 400 MHz), 8.25 ppm (1H, t); 7.9 ppm (2H, d); 7.3 ppm (2H, d); 4.4 ppm (2H, q); 4.0 ppm (2H, d); 2.35 ppm (3H, s); 1.4 ppm (9H, s); 1.35 ppm (3H, t)

Example 46

4-(3-tert-Butyl-1-ethyl-8-oxo-1,6,7,8-tetrahydro-pyrazolo[4,3-e][1,4]diazepin-5-yl)benzonitrile (R1=tert-butyl; R2=ethyl; R3=4-cyanophenyl)
Step 7:
According to M9, 0.425 g (1.76 mmol) of 5-tert-butyl-2-ethyl-4-nitro-2H-pyrazole-3-carboxylic acid (A) is reacted with 0.346 g (1.76 mmol) of 4-(2-aminoethanoyl)benzonitrile hydrochloride (*Yakugaku Zasshi*, 72, 305–307, 1952) to give 0.33 g (49%) of an amide of type C (see scheme 1).
MS (ES+), m/z=384

¹H NMR (CDCl₃, 400 MHz), 8.1 ppm (2H, d); 7.8 ppm (2H, d); 5.0 ppm (2H, d); 4.3 ppm (2H, m); 1.5 to 1.4 ppm (12H, m)

Step 8:
According to M12, 0.33 g (0.86 mmol) of the amide C (see scheme 1) is refluxed in ethanol with 0.97 g of tin chloride dihydrate to give 0.091 g (32%) of the expected product D (see Scheme 1).
MS (ES+), m/z=336
¹H NMR (DMSO, 400 MHz), 8.3 ppm (1H, t); 8.2 ppm (2H, d); 8.0 ppm (2H, d); 4.45 ppm (2H, m); 4.0 ppm (2H, d); 1.4 ppm (9H, s); 1.35 ppm (3H, t)

Example 47

3-tert-Butyl-5-(2,4-dimethoxyphenyl)-1-ethyl-6,7-dihydro-1H-pyrazolo[4,3-e][1,4]diazepin-8-one (R1=tert-butyl; R2=ethyl; R3=2,4-dimethoxyphenyl)
Step 7:
According to M9, 0.425 g (1.76 mmol) of 5-tert-butyl-2-ethyl-4-nitro-2H-pyrazole-3-carboxylic acid (A) is reacted with 0.407 g (1.76 mmol) of 2-amino-1-(2,4-dimethoxyphenyl)ethanone hydrochloride (*J. Chem. Res. Miniprint*, 7, 1581–1597, 1989) to give 0.56 g (76%) of an amide of type C (see Scheme 1).
MS (ES+), m/z=419
Step 8:
According to M12, 0.56 g (1.34 mmol) of the amide C (see scheme 1) is refluxed in ethanol with 1.51 g of tin chloride dihydrate to give 0.112 g (23%) of the expected product D (see Scheme 1).
MS (ES+), m/z=371
¹H NMR (DMSO, 400 MHz), 8.2 ppm (1H, t); 7.4 ppm (1H, s); 6.5 ppm (2H, m); 4.3 ppm (2H, m); 3.75 ppm (3H, s); 3.65 ppm (5H, bs); 1.2 ppm (9H, s); 1.15 ppm (3H, t)

Example 48

3,5-Di-tert-butyl-1-propyl-6,7-dihydro-1H-pyrazolo[4,3-e][1,4]diazepin-8-one (R1=tert-butyl; R2=propyl; R3=tert-butyl)
Step 7:
According to M9, 0.449 g (1.76 mmol) of 5-tert-butyl-2-ethyl-4-nitro-2H-pyrazole-3-carboxylic acid (A) is reacted with 0.267 g (1.76 mmol) of 1-amino-3,3-dimethylbutan-2-one hydrochloride (*J. Org. Chem.*, 53, 5, 1113–1114, 1988) to give 0.42 g (68%) of an amide of type C (see scheme 1).
MS (ES+), m/z=353
Step 8:
According to M12, 0.42 g (1.2 mmol) of the amide C (see scheme 1) is refluxed in ethanol with 1.34 g of tin chloride dihydrate to give 0.154 g (42%) of the expected product D (see Scheme 1).
MS (ES+), m/z=305
¹H NMR (DMSO, 400 MHz), 8.2 ppm (1H, t); 4.3 ppm (2H, t); 3.55 ppm (2H, d); 1.7 ppm (2H, m); 1.4 ppm (9H, s); 1.2 ppm (9H, s); 0.8 ppm (3H, t)

Example 49

3-tert-Butyl-1-propyl-5-p-tolyl-6,7-dihydro-1H-pyrazolo[4,3-e][1,4]diazepin-8-one (R1=tert-butyl; R2=propyl; R3=p-tolyl)
Step 7:
According to M9, 0.449 g (1.76 mmol) of 5-tert-butyl-4-nitro-2-propyl-2H-pyrazole-3-carboxylic acid (A) is reacted with 0.327 g (1.76 mmol) of 2-amino-1-p-tolylethanonehydrochloride to give 0.43 g (63%) of an amide of type C (see Scheme 1).
MS (ES+), m/z=387

Step 8:
According to M12, 0.43 g (1.11 mmol) of the amide C (see scheme 1) is refluxed in ethanol with 1.26 g of tin chloride to give 0.163 g (43%) of the expected product D (see Scheme 1).
MS (ES+), m/z=339
¹H NMR (DMSO, 400 MHz), 8.3 ppm (1H, t); 7.9 ppm (2H, m); 7.3 ppm (2H, m); 4.4 ppm (2H, t); 4.0 ppm (2H, d); 2.4 ppm (3H, s); 1.8 ppm (2H, t); 1.4 ppm (9H, s); 0.85 ppm (3H, t)

Example 50

4-(3-tert-Butyl-8-oxo-1-propyl-1,6,7,8-tetrahydro-1H-pyrazolo[4,3-e][1,4]diazepin-5-yl)benzonitrile (R1=tert-butyl; R2=propyl; R3=4-cyanophenyl)
Step 7:
According to M9, 0.449 g (1.76 mmol) of 5-tert-butyl-4-nitro-2-propyl-2H-pyrazole-3-carboxylic acid (A) is reacted with 0.346 g (1.76 mmol) of 4-(2-aminoethanoyl)benzonitrile hydrochloride (*Yakagaku Zasshi*, 72, 305–307, 1952) to give 0.36 g (51%) of an amide of type C (see Scheme 1).
MS (ES–), m/z=396
Step 8:
According to M12, 0.36 g (0.9 mmol) of the amide C (see scheme 1) is refluxed in ethanol with 1.02 g of tin chloride to give 0.116 g (37%) of the expected product D (see Scheme 1).
MS (ES+), m/z=350
¹H NMR (DMSO, 400 MHz), 8.35 ppm (1H, t); 8.2 ppm (2H, m); 8.0 ppm (2H, m); 4.4 ppm (2H, t); 4.0 ppm (2H, d); 1.8 ppm (2H, m); 1.4 ppm (9H, s); 0.85 ppm (3H, t)

Example 51

3-tert-Butyl-5-(2,4-dimethoxyphenyl)-1-propyl-6,7-dihydro-1H-pyrazolo[4,3-e][1,4]diazepin-8-one (R1=tert-butyl; R2=propyl; R3=2,4-dimethoxyphenyl)
Step 7:
According to M9, 0.449 g (1.76 mmol) of 5-tert-butyl-4-nitro-2-propyl-2H-pyrazole-3-carboxylic acid (A) is reacted with 0.407 g (1.76 mmol) of 2-amino-1-(2,4-dimethoxyphenyl)ethanone (*J. Chem. Res. Miniprint*, 7, 1581–1597, 1989) to give 0.59 g (77%) of an amide of type C (see Scheme 1).
MS (ES+), m/z=433
Step 8:
According to M12, 0.59 g (1.36 mmol) of the amide C (see scheme 1) is refluxed in ethanol with 1.54 g of tin chloride dihydrate to give 0.184 g (35%) of the expected product D (see scheme 1).
MS (ES+), m/z=385
¹H NMR (DMSO, 400 MHz), 8.4 ppm (1H, t); 7.55 ppm (1H, m); 6.6 ppm (2H, m); 4.35 ppm (2H, q); 3.9 ppm (3H, s); 3.8 ppm (5H, m); 1.8 ppm (2H, m); 1.35 ppm (9H, s); 0.8 ppm (3H, t)

Example 52

3-Butyl-1-ethyl-5-phenyl-6,7-dihydro-1H-pyrazolo[4,3-e][1,4]diazepin-8-thione (R1=butyl; R2=ethyl; R3=phenyl)
Step 9:
0.65 g (2 mmol) of 3-butyl-1-ethyl-5-phenyl-6,7-dihydro-1H-pyrazolo[4,3-e][1,4]diazepin-8-one is reacted with 1.77 g (4 mmol) of Lawesson's reagent and refluxed in toluene overnight to give 0.4 g (60%) of the desired thiolactam of type E (see Scheme 1).

Rf (95/5 CH₂Cl₂/acetone)=0.65
m.p.: 151.5° C.
MS (ES+), m/z=327
$^1$H NMR (CDCl₃, 400 MHz), 8.8 ppm (1H, t); 8.0 ppm (2H, m); 7.4 ppm (3H, m); 4.8 ppm (2H, q); 4.2 ppm (2H, d); 2.8 ppm (2H, m); 1.7 ppm (2H, m); 1.5 ppm (3H, m); 1.4 ppm (2H, m); 0.9 ppm (3H, t)

Example 53

1-Ethyl-3-methyl-5-pyrid-3-yl-6,7-dihydro-1H-pyrazolo[4,3-e][1,4]diazepin-8-one (R1=methyl; R2=ethyl; R3=3-pyridyl)
Step 7:
According to M8, 1.9 g (9.5 mmol) of 2-ethyl-5-methyl-4-nitro-2H-pyrazole-3-carboxylic acid (A) are reacted with 2 g (9.5 mmol) of 2-amino-1-pyrid-3-ylethanone hydrochloride (*Chem. Pharm. Bull.*, 32, 7, 2536–2543, 1984; *J. Amer. Chem. Soc.*, 67, 1468–1472, 1945) to give 2.2 g (73%) of an amide of type C (see Scheme 1).

Rf (90/10 CH₂Cl₂/acetone)=0.27
$^1$H NMR (CDCl₃, 400 MHz), 9.55 ppm (1H, t); 9.2 ppm (1H, s); 8.8 ppm (1H, d); 7.95 ppm (2H, m); 5.0 ppm (2H, d); 4.2 ppm (2H, q); 2.4 ppm (3H, s); 1.4 ppm (3H, t)
Step 8:
According to M12, 1.1 g (3.47 mmol) of the amide C (see scheme 1) are refluxed in ethanol with 3.9 g (5 eq.) of tin chloride dihydrate to give 0.26 g (28%) of the expected product D (see scheme 1).

m.p.=178° C.
MS (ES+), m/z=270
$^1$H NMR (DMSO, 400 MHz), 9.2 ppm (1H, s); 8.7 ppm (1H, d); 8.4 ppm (1H, d); 8.3 ppm (1H, t); 7.5 ppm (1H, dd); 4.4 ppm (2H, q); 4.1 ppm (2H, d); 2.3 ppm (3H, s); 1.4 ppm (3H, t)

Example 54

1-Ethyl-3-methyl-5-pyrid-2-yl-6,7-dihydro-1H-pyrazolo[4,3-e][1,4]diazepin-8-one (R1=methyl; R2=ethyl; R3=2-pyridyl)
Step 7:
According to M8, 1.9 g (9.5 mmol) of 2-ethyl-5-methyl-4-nitro-2H-pyrazole-3-carboxylic acid (A) are reacted with 2 g (9.5 mmol) of 2-amino-1-pyrid-2-ylethanone hydrochloride (*J. Amer. Chem. Soc.*, 67, 1468–1472, 1945; *J. Chem. Soc.*, 753, 1938) to give 2.2 g (73%) of an amide of type C (see Scheme 1).

Rf (90/10 CH₂Cl₂/acetone)=0.38
MS (ES+), m/z=318
$^1$H NMR (CDCl₃, 400 MHz), 9.5 ppm (1H, bs); 8.8 ppm (1H, m); 8.0 ppm (2H, m); 7.7 ppm (1H, m); 5.0 ppm (2H, d); 4.2 ppm (2H, q); 2.4 ppm (3H, s); 1.4 ppm (3H, t)
Step 8:
According to M12, 1.1 g (3.47 mmol) of the amide C (see scheme 1) are refluxed in ethanol with 3.9 g (5 eq.) of tin chloride dihydrate to give 0.19 g (20%) of the expected product D (see Scheme 1).

m.p.=153° C.
MS (ES+), m/z=270
$^1$H NMR (DMSO, 400 MHz), 8.7 ppm (H, d); 8.3 ppm (21H, m); 8.0 ppm (1H, t); 7.5 ppm (1H, dd); 4.5 ppm (2H, q); 4.4 ppm (2H, d); 2.3 ppm (3H, s); 1.4 ppm (3H, t)

Example 55

1-Ethyl-3-methyl-5-phenyl-6,7-dihydro-1H-pyrazolo[4,3-e][1,4]diazepin-8-ylidenecyanamide (R1=methyl; R2=ethyl; R3=phenyl)
Step 10:
According to M13, 2 g (7 mmol) of 1-ethyl-3-methyl-5-phenyl-6,7-dihydro-1H-pyrazolo[4,3-e][1,4]diazepin-8-thione are reacted with 0.21 g of 80% sodium hydride in refluxing THF for 1 h, followed by addition of 0.52 ml of methyl iodide, at room temperature. The mixture is refluxed for 2 h to give 2.1 g (100%) of the expected methylsulphanyl G (see scheme 1).

MS (ES+), m/z=299
$^1$H NMR (CDCl₃, 400 MHz), 8.1 ppm (2H, d); 7.5 ppm (3H, m); 4.5 ppm (4H, m); 2.5 ppm (3H, s); 2.4 ppm (3H, s); 1.5 ppm (3H, t)
Step 11: 0.5 g (1.67 mmol) of the methylsulphanyl G is reacted with 0.14 g (2 eq.) of cyanamide to give 0.29 g (60%) of the desired product F (see scheme 1).

Rf (95/5 CH₂Cl₂/MeOH)=0.32
m.p.=280° C.
MS (ES+), m/z=293
$^1$H NMR (DMSO, 400 MHz), 9.5 ppm (1H, s); 8.2 ppm (2H, m); 7.5 ppm (3H, m); 4.5 ppm (2H, q); 4.2 ppm (2H, s); 2.3 ppm (3H, s); 1.4 ppm (3H, t)

Example 56

N-[4-(1-Ethyl-3-methyl-8-oxo-1,6,7,8-tetrahydropyrazolo[4,3-e][1,4]diazepin-5-yl)phenyl]-(phenylsulphonyl)benzenesulphonamide, (R1=methyl; R2=ethyl; R3=4-N-(phenylsulphonyl)benzenesulphonamidephenyl)

0.2 g (0.7 mmol) of 5-(4-aminophenyl)-1-ethyl-3-methyl-6,7-dihydro-1H-pyrazolo[4,3-e][1,4]diazepin-8-one, is introduced into a round-bottomed flask and 10 ml of acetonitrile are added, followed by 0.158 g (1.41 mmol) of 1,4-diazabicyclo[2.2.2]octane, and 0.116 ml (0.91 mmol) of benzenesulphonyl chloride. The reaction mixture is stirred overnight at room temperature and then evaporated to dryness to give 0.54 g of an oily compound. The crude product is purified by flash chromatography using the following elution gradient: from CH₂Cl₂ to 98/2 CH₂Cl₂/methanol. After evaporation and crystallization from methanol, 0.19 g (48%) of a yellow powder are obtained.

MS (ES+), m/z=564
m.p.=>230° C.
$^1$H NMR (CDCl₃, 400 MHz), 1.5 ppm (3H, t); 2.4 ppm (3H, s); 4.1 ppm (2H, m); 4.55 ppm (2H, q); 6.25 ppm (1H, m); 7.1 ppm (2H, m); 7.6 ppm (4H, m); 7.7 ppm (2H, m); 7.85 ppm (6H, m)

Example 57

3-tert-Butyl-1-ethyl-5-phenyl-6,7-dihydro-1H-pyrazolo[4,3-e][1,4]diazepin-8-ylidene-cyanamide (R1=tert-butyl; R2=ethyl; R3=phenyl)
Step 10:
According to M13, 1.65 g (5.05 mmol) 3-tert-butyl-1-ethyl-5-phenyl-6,7-dihydro-1H-pyrazolo[4,3-e][1,4]diazepin-8-thione are reacted with 0.15 g of 80% sodium hydride in refluxing THF for 1 hour, followed by addition of 0.38 ml of methyl iodide, at room temperature. The mixture is refluxed for 2 h to give 1.55 g (90%) of the expected methylsulphanyl G (see scheme 1).
Step 11:
0.5 g (1.47 mmol) of the methylsulphanyl G is reacted with 0.12 g (2 eq.) of cyanamide to give 0.185 g (38%) of the expected product of type F (see Scheme 1).

Rf (95/5 CH$_2$Cl$_2$/methanol)=0.57
m.p.=250° C.
MS (ES+), m/z=335
$^1$H NMR (DMSO, 400 MHz), 9.5 ppm (1H, s); 8.1 ppm (2H, d); 7.5 ppm (3H, d); 4.5 ppm (2H, q); 4.2 ppm (2H, bs); 1.4 ppm (6H, s); 1.35 ppm (3H, m)

Example 58

1-Cyclopropylmethyl-3-methyl-5-phenyl-6,7-dihydro-1H-pyrazolo[4,3-e][1,4]diazepin-8-one,
(R1=methyl; R2=cyclopropylmethyl; R3=phenyl)
Step 5:
According to M5, 1.9 g (9.5 mmol) of ethyl-3-methyl-4-nitro-1H-5-pyrazolecarboxylate (commercial) are reacted with 5 g (37 mmol) of (bromomethyl)cyclopropane (commercial) in the presence of 1.43 g (9.5 mmol) of sodium iodide to give 1.14 g (48%) of a pyrazole A5 (see scheme 1).
Rf (80/20 cyclohexane/EtOAc)=0.47
$^1$H NMR (CDCl$_3$, 400 MHz), 4.45 ppm (2H, q); 4.05 ppm (2H, d); 2.5 ppm (3H, s); 1.4 ppm (3H, t); 1.3 ppm (1H, m); 0.6 ppm (2H, m); 0.4 ppm (2H, m)
Step 6:
1.14 g (4.5 mmol) of the pyrazole A5 (see scheme 1) are reacted with 0.27 g (6.75 mmol) of sodium hydroxide in a mixture of methanol and water to give 0.93 g (91%) of a pyrazole of type A (see Scheme 1).
MS (ES−), m/z=224
Step 7:
According to M9, 0.5 g (2.22 mmol) of 2-(cyclopropylmethyl)-5-methyl-4-nitro-2H-pyrazole-3-carboxylic acid is reacted with 0.38 g (2.22 mmol) of 2-aminoacetophenone hydrochloride to give 1 g of the compound C (see Scheme 1).
MS (ES+), m/z=343
Step 8:
According to M12, 1 g (2.9 mmol) of compound C (see scheme 1) is refluxed in ethanol with 2.5 g (11 mmol), of tin chloride dihydrate to give 0.17 g (27%) of the expected product D (see scheme 1).
Rf (90/10 CH$_2$Cl$_2$/acetone)=0.42
MS (ES+), m/z=295
$^1$H NMR (CDCl$_3$, 400 MHz), 7.95 ppm (2H, m); 7.5 ppm (3H, m); 6.15 ppm (1H, t); 4.4 ppm (2H, d); 4.1 ppm (2H, d); 2.45 ppm (3H, s); 1.45 ppm (1H, m); 0.5 ppm (2H, m); 0.45 ppm (2H, m)

Example 59

1-Allyl-3-methyl-5-phenyl-6,7-dihydro-1H-pyrazolo[4,3-e][1,4]diazepin-8-one
(R1=methyl; R2=allyl; R3=phenyl)
Step 5:
According to M5, 2.5 g (12.5 mmol) of ethyl-3-methyl-4-nitro-1H-5-pyrazolecarboxylate (commercial) are reacted with 1.09 ml (12.5 mmol) of allyl bromide (commercial) in the presence of 0.38 g (12.5 mmol) of 80% sodium hydride in 1,2-dimethoxyethane to give 0.35 g (12%) of a pyrazole A5 (see Scheme 1).
Rf (70/30 cyclohexane/EtOAc)=0.53
$^1$H NMR (CDCl$_3$, 400 MHz), 5.9-6 ppm (1H, m); 5.3 ppm (1H, d); 5.2 ppm (1H, d); 4.8 ppm (2H, d); 4.45 ppm (2H, q); 2.5 ppm (3H, s); 1.4 ppm (3H, t)
Step 6:
0.35 g (1.46 mmol) of the pyrazole A5 (see scheme 1) is reacted with 0.09 g (2.25 mmol) of sodium hydroxide in a mixture of methanol and water, to give 0.071 g (23%) of a pyrazole of type A (see Scheme 1).
MS (ES−), m/z=210
Step 7:
According to M9, 0.071 g (0.34 mmol) of 2-allyl-5-methyl-4-nitro-2H-pyrazole-3-carboxylic acid is reacted with 0.058 g (0.34 mmol) of 2-aminoacetophenone hydrochloride to give 0.174 g of compound C (see Scheme 1).
Step 8:
According to M12, 0.174 g (0.5 mmol) of compound C (see scheme 1) is refluxed in ethanol with 0.38 g (1.68 mmol) of tin chloride dihydrate to give 0.01 g (11%) of the expected product D (see Scheme 1).
Rf (90/10 CH$_2$Cl$_2$/acetone)=0.30
MS (ES+), m/z=281

Example 60

1-Ethyl-3-methyl-5-(4-trifluoromethylphenyl)-6,7-dihydro-1H-pyrazolo[4,3-e][1,4]diazepin-8-one
(R1=methyl; R2=ethyl; R3=4-trifluoromethylphenyl)
Step 7:
According to M9, 0.33 g (1.67 mmol) of 2-ethyl-5-methyl-4-nitro-2H-pyrazole-3-carboxylic acid (A) is reacted with 0.4 g (1.67 mmol) of 2-amino-1-(4-trifluoromethylphenyl)ethanone hydrochloride (*J. Amer. Chem. Soc.*, 75, 5884–5886, 1953; *J. Org. Chem.*, 42, 5, 868–871, 1977) to give a crude amide of type C (see scheme 1).
MS (ES−), m/z=383
Step 8:
According to M12, 0.64 g (1.67 mmol) of the amide C (see scheme 1) is refluxed in ethanol with 1.9 g (5 eq.) of tin chloride dihydrate to give 0.153 g (27%) of the expected product of type D (see Scheme 1).
Rf (90/10 CH$_2$Cl$_2$/acetone)=0.22
m.p.=195° C.
MS (ES+), m/z=337
$^1$H NMR (DMSO, 400 MHz), 8.4 ppm (1H, t); 8.3 ppm (2H, d); 8.0 ppm (2H, d); 4.5 ppm (2H, q); 4.1 ppm (2H, d); 2.4 ppm (3H, s); 1.4 ppm (3H, t)

Example 61

1-Ethyl-3-isopropyl-5-(4-trifluoromethylphenyl)-6,7-dihydro-1H-pyrazolo[4,3-e][1,4]diazepin-8-one
(R1=isopropyl; R2=ethyl; R3=4-trifluoromethylphenyl)
Step 7:
According to M9, 0.38 g (1.67 mmol) of 2-ethyl-5-isopropyl-4-nitro-2H-pyrazole-3-carboxylic acid (A) is reacted with 0.4 g (1.67 mmol) of 2-amino-1-(4-trifluoromethylphenyl)ethanone hydrochloride (*J. Amer. Chem. Soc.*, 75, 5884–5886, 1953; *J. Org. Chem.*, 42, 5, 868–871, 1977) to give a crude amide of type C (see Scheme 1).
MS (ES−), m/z=411
Step 8:
According to M12, 0.69 g (1.67 mmol) of the amide C (see scheme 1) is refluxed in ethanol with 1.9 g (5 eq.) of tin chloride dihydrate to give 0.161 g (26.5%) of the expected product D (see Scheme 1).
Rf (90/10 CH$_2$Cl$_2$/acetone)=0.28
m.p.=133
MS (ES+), m/z=364
$^1$H NMR (DMSO, 400 MHz), 8.3 ppm (1H, t); 8.2 ppm (2H, d); 7.9 ppm (2H, d); 4.4 ppm (2H, q); 4.0 ppm (2H, d); 3.3 ppm (1H, m); 1.4 to 1.3 ppm (9H, m)

Example 62

1-Ethyl-3-methyl-5-(4-trifluoromethylphenyl)-6,7-dihydro-1H-pyrazolo[4,3-e][1,4]diazepin-8-one (R1=tert-butyl; R2=ethyl; R3=4-trifluoromethylphenyl)
Step 7:

According to M9, 0.4 g (1.67 mmol) of 5-tert-butyl-2-ethyl-4-nitro-2H-pyrazole-3-carboxylic acid (A) is reacted with 0.4 g (1.67 mmol) of 2-amino-1-(4-trifluoromethylphenyl)ethanone hydrochloride (*J. Amer. Chem. Soc.*, 75, 5884–5886, 1953; *J. Org. Chem.*, 42, 5, 868–871, 1977) to give a crude amide of type C (see Scheme 1).

MS (ES−), m/z=425
Step 8:

According to M12, 0.712 g (1.67 mmol) of the amide C (see scheme 1) is refluxed in ethanol with 1.9 g (5 eq.) of tin chloride dihydrate to give 0.14 g (22%) of the expected product D (see Scheme 1).

Rf (90/10 $CH_2Cl_2$/acetone)=0.33
m.p.=144° C.
MS (ES+), m/z=379
$^1$H NMR (DMSO, 400 MHz), 8.3 ppm (1H, t); 8.2 ppm (2H, d); 7.9 ppm (2H, d); 4.4 ppm (2H, q); 4.1 ppm (2H, d); 1.4 ppm (9H, s); 1.35 ppm (3H, t)

Example 63

3-Isopropyl-1-propyl-5-p-tolyl-6,7-dihydro-1H-pyrazolo[4,3-e][1,4]diazepin-8-thione (R1=isopropyl; R2=propyl; R3=p-tolyl)
Step 9:

0.9 g (2.7 mmol) of 3-isopropyl-1-propyl-5-p-tolyl-6,7-dihydro-1H-pyrazolo[4,3-e][1,4]diazepin-8-one is reacted with 2.24 g (5.53 mmol) of Lawesson's reagent and refluxed in toluene overnight to give 0.73 g (77%) of the thiolactam of type E (see scheme 1).

Rf ($CH_2Cl_2$)=0.22
m.p.=162.9° C.
MS (ES+), m/z=340.9
$^1$H NMR (CDCl$_3$, 400 MHz) 0.9 ppm (3H, t); 1.35 ppm (6H, m); 1.9 ppm (2H, m); 2.4 ppm (3H, s); 3.3 ppm (1H, m); 4.15 ppm (2H, m); 4.75 ppm (2H, m); 7.2 ppm (2H, d); 7.9 ppm (2H, d); 8.65 ppm (1H, m)

Example 64

3,5-Di-tert-butyl-1-propyl-6,7-dihydro-1H-pyrazolo[4,3-e][1,4]diazepin-8-thione (R1=tert-butyl; R2=propyl; R3=tert-butyl)
Step 9:

1.5 g (4.9 mmol) of 3,5-di-tert-butyl-1-propyl-6,7-dihydro-1H-pyrazolo[4,3-e][1,4]diazepin-8-one are reacted with 4 g (9.8 mmol) of Lawesson's reagent and refluxed in toluene overnight to give 1.4 g (90%) of the thiolactam of type E (see Scheme 1).

Rf (80/20 cyclohexane/EtOAc)=0.54
m.p.: 205° C.
MS (ES+), m/z=321
$^1$H NMR (CDCl$_3$, 400 MHz), 9.0 ppm (1H, m); 4.7 ppm (2H, m); 1.9 ppm (2H, m); 1.4 ppm (9H, s); 1.25 ppm (9H, s); 0.9 ppm (3H, t)

Example 65

5-tert-Butyl-3-isopropyl-1-propyl-6,7-dihydro-1H-pyrazolo[4,3-e][1,4]diazepin-8-thione (R1=isopropyl; R2=propyl; R3=tert-butyl)
Step 9:

0.35 g (1.2 mmol) of 5-tert-butyl-3-isopropyl-1-propyl-6,7-dihydro-1H-pyrazolo[4,3-e][1,4]diazepin-8-one is reacted with 0.98 g (2.4 mmol) of Lawesson's reagent and refluxed in toluene overnight to give 0.25 g (68%) of the thiolactam of type E (see Scheme 1).

Rf (70/30 cyclohexane/EtOAc)=0.67
m.p.: 165° C.
MS (ES+), m/z=307
$^1$H NMR (CDCl$_3$, 400 MHz), 8.8 ppm (1H, m); 4.7 ppm (2H, m); 3.75 ppm (2H, m); 3.2 ppm (1H, m); 1.9 ppm (2H, m); 1.3 ppm (6H, d); 1.25 ppm (9H, s); 0.9 ppm (3H,t)

Example 66

1-Ethyl-3-isopropyl-5-p-tolyl-6,7-dihydro-1H-pyrazolo[4,3-e][1,4]diazepin-8-thione (R1=isopropyl; R2=ethyl; R3=p-tolyl)
Step 9:

0.62 g (2 mmol) of 1-ethyl-3-isopropyl-5-p-tolyl-6,7-dihydro-1H-pyrazolo[4,3-e][1,4]diazepin-8-one is reacted with 1.62 g (4 mmol) of Lawesson's reagent and refluxed in toluene overnight to give 0.567 g (87%) of the desired thiolactam of type E (see Scheme 1).

Rf (98/2 $CH_2Cl_2$/MeOH)=0.46
m.p.: 178° C.
MS (ES+), m/z=327
$^1$H NMR (CDCl$_3$, 400 MHz), 8.5 ppm (1H, bs); 7.8 ppm (2H, d); 7.15 ppm (2H, d); 4.75 ppm (2H, q); 4.1 ppm (2H, bs); 3.2 ppm (1H, m); 2.3 ppm (3H, s); 1.4 ppm (3H, t); 1.3 ppm (6H, d)

Example 67

5-tert-Butyl-1-ethyl-3-isopropyl-6,7-dihydro-1H-pyrazolo[4,3-e][1,4]diazepin-8-thione (R1=isopropyl; R2=ethyl; R3=tert-butyl)
Step 9:

0.4 g (1.45 mmol) of 5-tert-butyl-1-ethyl-3-isopropyl-6,7-dihydro-1H-pyrazolo[4,3-e][1,4]diazepin-8-one is reacted with 1.17 g (2.9 mmol) of Lawesson's reagent and refluxed in toluene overnight to give 0.193 g (46%) of the desired thiolactam of type E (see Scheme 1).

Rf (98/2 $CH_2Cl_2$/MeOH)=0.43
m.p.: 218° C.
MS (ES+), m/z=293
$^1$H NMR (DMSO, 400 MHz), 10.35 ppm (1H, bs); 4.65 ppm (2H, q); 3.9–3.3 ppm (2H, bs); 3.1 ppm (1H, m); 1.3 ppm (3H, t); 1.2 ppm (6H, d); 1.15 ppm (9H, s)

Example 68

(±)3-sec-Butyl-1-ethyl-5-phenyl-6,7-dihydro-1H-pyrazolo[4,3-e][1,4]diazepin-8-one (R1=sec-butyl; R2=ethyl; R3=phenyl)
Synthesis of the Pyrazole (Following Steps 1, 2, 3, 5 and 6):
Step 1:

3.44 g (149.8 mmol) of sodium are dissolved portionwise in 200 ml of anhydrous ethanol under nitrogen, at room temperature. 20.35 ml (149.8 mmol) of diethyl oxalate in 60 ml of anhydrous ethanol are added. 15 g (149.8 mmol) of 3-methyl-2-pentanone are added. The reaction mixture is refluxed for 3 h, under nitrogen and with stirring, and is then evaporated to dryness; the residue is taken up in 300 ml; of HCl (1.2N) and then extracted with diethyl ether (3 times 200 ml). The organic phase is dried over sodium sulphate and then concentrated to give 26.1 g (89%) of a colourless oil (compound A1, see scheme 1).

Rf (60/40 $CH_2Cl_2$/heptane)=0.4

$^1$H NMR ($CDCl_3$, 400 MHz), 0.9 ppm (3H, t); 1.1 ppm (3H, d); 1.4 ppm (3H1, t); 1.5 ppm (1H, m); 1.7 ppm (1H, m); 2.4 ppm (2H, m); 4.3 ppm (2H, q); 6.4 ppm (1H, s); 14.6 ppm (1H, m).

Step 2:

8.25 g (125 mmol) of potassium hydroxide are dissolved in 120 ml of water and the reaction medium is cooled to 0° C. 25 g (125 mmol) of compound A1 (see scheme 1) are added portionwise and the mixture is stirred for 15 min at 0° C. 16.3 g (130.11 mmol) of hydrazine sulphate are added and the mixture is then stirred for 20 min at 0° C. It is stirred at room temperature overnight, after which 200 ml of water are added and the mixture is extracted with dichloromethane (3×200 ml). The organic phase obtained is washed with saturated NaCl solution (1×200 ml) and then dried over sodium sulphate and concentrated. 24.5 g of an powder are obtained.

The product is purified by flash chromatography (95/5 $CH_2Cl_2$/acetone) to give 17.6 g (68%) of a white powder (compound A6, see scheme 1).

Rf (95/5 $CH_2Cl_2$/acetone)=0.3

$^1$H NMR ($CDCl_3$, 400 MHz), 0.85 ppm (3H, t); 1.3 ppm (3H, d); 1.35 ppm (3H, t); 1.6 ppm (1H, m); 2.8 ppm (1H, m); 4.4 ppm (2H, m); 6.6 ppm (1H, s); 11.6 ppm (1H, m).

Step 3:

According to M3, 20.7 g (89.95 mmol) of copper(II) nitrate hemipentahydrate (2.5 $H_2O$) and 100 ml of trifluoroacetic anhydride are introduced into a round-bottomed flask, the mixture is stirred under nitrogen for 5 min and 17 g of compound A6 (see scheme 1) (80.87 mmol) dissolved in 100 ml of chloroform are then added. This mixture is refluxed with stirring and under nitrogen for 5 hours. This product is purified by flash chromatography (98/2 $CH_2Cl_2$/acetone) to give 20 g of a blueish oil. This product is taken up in 200 ml of HCl (10%) and then extracted with diethyl ether (3 times 300 ml), and the organic phase is dried and concentrated to give 16.81 g (70%) of a colourless oil (compound A7, see scheme 1).

MS (ES-), m/z=239.91

Rf (97/3 $CH_2Cl_2$/acetone)=0.3

$^1$H NMR ($CDCl_3$, 400 MHz), 0.9 ppm (3H, t); 1.4 ppm (6H, m); 1.7 ppm (2H, m); 3.4 ppm (1H, m); 4.4 ppm (2H, q); 11.6 ppm (1H, m).

Step 5:

According to M4, 0.92 g (3.81 mmol) of compound A7 (see scheme 1) and 0.5 ml (3.81 mmol) of diethyl sulphate are introduced into a round-bottomed flask and the mixture is then refluxed with stirring and under nitrogen for 1 h 30 min. After cooling to room temperature, 6 g of ice and 15 ml of HCl (10%) are added and the mixture is stirred and then extracted with dichloromethane (3 times 40 ml). The organic phase is dried and concentrated to give 1.1 g of a colourless oil. This product is purified by flash chromatography (gradient: 9/1 to 7/3 cyclohexane/ethyl acetate) to give 0.8 g (78%) of a white powder (compound A5, see scheme 1).

Rf (80/20 cyclohexane/ethyl acetate)=0.3

$^1$H NMR ($CDCl_3$, 400 MHz), 0.9 ppm (3H, t); 1.35 ppm (3H, m); 1.45 ppm (6H, m); 1.6 ppm (1H, m); 1.8 ppm (1H, m); 3.3 ppm (1H, m); 4.25 ppm (2H, q); 4.5 ppm (2H, q).

Step 6:

8.3 g (33.80 mmol) of compound A5 (see scheme 1) are dissolved in 40 ml of methanol, followed by addition of a solution of 2 g (50.7 mmol) of sodium hydroxide in 40 ml of water. The mixture is stirred at RT for 2 h. After evaporating off the methanol, the residue is taken up in $CH_2Cl_2$, an identical volume of water is added, followed by addition of concentrated (36%) hydrochloric acid to acidic pH, with stirring. The organic phase is dried over $Na_2SO_4$ and concentrated to give 7.5 g (98%) of a white powder (compound A, see scheme 1).

$^1$H NMR ($CDCl_3$, 400 MHz), 0.9 ppm (3H, m); 1.3 ppm (3H, m); 1.5 ppm (3H, m); 1.6 ppm (1H, m); 1.8 ppm (1H, m); 3.3 ppm (1H, m); 4.5 ppm (2H, q); 9.3 ppm (1H, m).

Step 7:

According to M9, 0.434 g (1.8 mmol) of 5-sec-butyl-2-ethyl-4-nitro-2H-pyrazole-3-carboxylic acid (A) is reacted with 0.309 g (1.8 mmol) of 2-aminoacetophenone hydrochloride to give a crude amide of type C (see Scheme 1).

MS (ES+), m/z=359

Step 8:

According to M12, 0.65 g (1.8 mmol) of the amide C (see scheme 1) is refluxed in ethanol with 3.25 g (5 eq.) of tin chloride dihydrate to give 0.14 g (25%) of the expected product D (see scheme 1).

MS (ES+), m/z=311

$^1$H NMR ($CDCl_3$, 400 MHz), 7.9 ppm (2H, m); 7.4 ppm (3H, m); 7.2 ppm (1H, m); 4.5 ppm (2H, q); 4.1 ppm (2H, t); 3.1 ppm (1H, m); 1.8 ppm (1H, m); 1.7 ppm (1H, m); 1.4 ppm (3H, t); 1.3 ppm (3H, d); 0.8 ppm (3H, t)

Example 69

(±)3-sec-Butyl-1-ethyl-5-pyrid-4-yl-6,7-dihydro-1H-pyrazolo[4,3-e][1,4]diazepin-8-one (R1=sec-butyl; R2=ethyl; R3=4-pyridyl)

Synthesis of the Pyrazole: See Steps 1, 2, 3, 5 and 6 of Example 68.

Step 7:

According to M9, 0.434 g (1.8 mmol) of 5-sec-butyl-2-ethyl-4-nitro-2H-pyrazole-3-carboxylic acid is reacted with 0.376 g (1.8 mmol) of 2-amino-1-pyrid-4-ylethanone hydrchloride (*J. Med. Chem.*, 38, 17, 3342–3350, 1995; *J. Amer. Chem. Soc.*, 67, 1468–1472, 1945) to give a crude amide of type C (see scheme 1).

MS (ES+), m/z=359.8

Step 8:

According to M12, 0.65 g (1.8 mmol) of the amide C (see scheme 1) is refluxed in ethanol with 3.25 g (5 eq.) of tin chloride dihdyrate to give 0.135 g (24%) of the expected product D (see scheme 1).

m.p.: 86–88.5° C.

MS (ES+), m/z=312

$^1$H NMR ($CDCl_3$, 400 MHz), 8.8 ppm (2H, d); 7.8 ppm (2H, d); 7.2 ppm (1H, m); 4.6 ppm (2H, q); 4.1 ppm (2H, d); 3.1 ppm (1H, m); 1.9 ppm (1H, m); 1.7 ppm (1H, m); 1.5 ppm (3H, t); 1.4 ppm (3H, d); 0.9 ppm (3H, q)

Example 70

(±)3-sec-Butyl-5-phenyl-1-propyl-6,7-dihydro-1H-pyrazolo-[4,3-e][1,4]diazepin-8-one (R1=sec-butyl; R2=propyl; R3=phenyl)

Synthesis of the Pyrazole: See Steps 1, 2 and 3 of Example 68 and the Following Steps 5 and 6.

Step 5:

According to M5, 4.90 g (66.32 mmol) of $Li_2CO_3$ are added, under a stream of nitrogen, to a solution of 6.4 g (26.53 mmol) of compound A7 (see scheme 1) in 110 ml of anhydrous DMF, followed by addition of 6.5 ml (66.32 mmol) of iodopropane. The reaction medium is heated at 60°

C. for 24 h. It is cooled to room temperature and then poured into 100 ml of HCl (1.2N), the exothermicity being controlled by an ice bath. After extracting with dichloromethane (3 times 100 ml), the organic phase obtained is washed with saturated NaCl solution (100 ml), dried over $Na_2SO_4$ and evaporated to dryness to give 7 g of an oily compound. The product is purified by flash chromatography (gradient: 70/30 to 60/40 heptane/$CH_2Cl_2$) to give 5 g (66%) of a colourless oil which crystallizes (compound A5, see scheme 1).

Rf (50/50 heptane/$CH_2Cl_2$)=0.3

$^1$H NMR ($CDCl_3$, 400 MHz), 0.90 ppm (6H, m); 1.25 ppm (3H, m); 1.40 ppm (3H, m); 1.60 ppm (1H, m); 1.80 ppm (3H, m); 3.30. ppm (1H, m); 4.25 ppm (2H, q); 4.40 ppm (2H, q).

Step 6:

4.94 g (18.41 mmol) of compound A5 (see scheme 1) are dissolved in 21 ml of methanol, followed by addition of a solution of 1.1 g (27.61 mmol) of sodium hydroxide in 21 ml of water. This mixture is stirred at RT for 2 h. After evaporating off the methanol, the residue is taken up in $CH_2Cl_2$ and an identical volume of water is added, followed by addition of concentrated (36%) hydrochloric acid to acidic pH, with stirring. The organic phase is dried over $Na_2SO_4$ and concentrated to give 4.5 g (96%) of a white powder (compound A, see scheme 1).

$^1$H NMR ($CDCl_3$, 400 MHz), 0.9 ppm (6H, m); 1.3 ppm (3H, d); 1.6 ppm (1H, m); 1.8 ppm (1H, m); 1.9 ppm (2H, m); 3.3 ppm (1H, m); 4.4 ppm (2H, q); 7.6 ppm (1H, m).

Step 7:

According to M9, 0.46 g (1.8 mmol) of 5-sec-butyl-4-nitro-2-propyl-2H-pyrazole-3-carboxylic acid (A) is reacted with 0.31 g (1.8 mmol) of 2-aminoacetophenone hydrochloride to give a crude amide of type C (see scheme 1).

MS (ES+), m/z=373

Step 8:

According to M12, 0.67 g (1.8 mmol) of the amide C (see scheme 1) is refluxed in ethanol with 3.35 g (5 eq.) of tin chloride dihydrate to give 0.035 g (6%) of the expected product D (see scheme 1).

MS (ES+), m/z=325

$^1$H NMR ($CDCl_3$, 400 MHz), 7.9 ppm (2H, m); 7.5 ppm (3H, m); 6.7 ppm (1H, m); 4.5 ppm (2H, m); 4.1 ppm (2H, m); 3.1 ppm (1H, m); 2.0 ppm to 1.6 ppm (4H, m); 1.4 ppm (3H, d); 0.9 ppm (6H, m).

Example 71

(±)3-sec-Butyl-1-propyl-5-pyrid-4-yl-6,7-dihydro-1H-pyrazolo[4,3-e][1,4]diazepin-8-one (R1=sec-butyl; R2=propyl; R3=4-pyridyl)

Synthesis of the Pyrazole: See Steps 1, 2, 3, 5, 6 of Example 70.

Step 7:

According to M9, 0.46 g (1.8 mmol) of 5-sec-butyl-4-nitro-2-propyl-2H-pyrazole-3-carboxylic acid is reacted with 0.376 g (1.8 mmol) of 2-amino-1-pyrid-4-ylethanone hydrochloride (*J. Med. Chem.*, 38, 17, 3342–3350, 1995; *J. Amer. Chem. Soc.*, 67, 1468–1472, 1945) to give a crude amide of type C (see scheme 1).

MS (ES+), m/z=373.6

Step 8:

According to M12, 0.62 g (1.66 mmol) of the amide C (see scheme 1) is refluxed in ethanol with 3.36 g (5 eq.) of tin chloride dihydrate to give 0.1 g (17.3%) of the expected product D (see scheme 1).

m.p.: 110° C.

MS (ES+), m/z=325.8

$^1$H NMR ($CDCl_3$, 400 MHz), 8.7 ppm (2H, d); 7.7 ppm (2H, d); 7.0 ppm (1H, t); 4.5 ppm (2H, d); 4.0 ppm (2H, d); 3.1 ppm (1H, m); 1.9 ppm (2H, m); 1.8 ppm (1H, m); 1.7 ppm (1H, m); 1.3 ppm (3H, d); 0.9 ppm (3H, m); 0. 8 ppm (3H, m).

Example 72

3-Cyclohexyl-1-ethyl-5-phenyl-6,7-dihydro-1H-pyrazolo-[4,3-e][1,4]diazepin-8-one (R1=cyclohexyl; R2=ethyl; R3=phenyl)

Synthesis of the Pyrazole: See the Following Steps 1, 2, 3, 5 and 6.

Step 1:

2.46 g (107 mmol) of sodium are dissolved portionwise in 250 ml of anhydrous ethanol under nitrogen at room temperature. 14.52 ml (107 mmol) of diethyl oxalate in 60 ml of anhydrous ethanol are added. 15 g (107 mmol) of acetylcyclohexane are added. The reaction mixture is refluxed for 3 h, under nitrogen and with stirring, and then evaporated to dryness, the residue is taken up in 300 ml of HCl (1.2 N) and is then extracted with diethyl ether (3 times 200 ml). The organic phase is dried over sodium sulphate and then concentrated to give 23.2 g (96%) of a colourless oil (compound A1, see scheme 1).

Rf (60/40 $CH_2Cl_2$/n-heptane)=0.1

$^1$H NMR ($CDCl_3$, 400 MHz), 1.3 ppm (8H, m); 1.8 ppm (5H, m); 2.35 ppm(1H, m); 4.3 ppm (2H, q); 6.4 ppm (1H, s); 14.6 ppm (1H, m).

Step 2:

7 g (104 mmol) of potassium hydroxide are dissolved in 110 ml of water and the reaction medium is cooled to 0° C. 25 g (110 mmol) of compound A1 (see scheme 1) are added portionwise and the mixture is stirred for 15 min at 0° C. 13.5 g (104 mmol) of hydrazine sulphate are added and the mixture is then stirred for 20 min at 0° C. The resulting mixture is stirred overnight, 200 ml of water are then added and this mixture is extracted with dichloromethane (3 times 200 ml). The organic phase obtained is washed with saturated NaCl solution (1×200 ml) and then dried over sodium sulphate and concentrated. 23.4 g of a powder are obtained.

The product is purified by flash chromatography (gradient: 97/3 to 90/10 $CH_2Cl_2$/acetone) to give 15 g (61%) of a white powder (compound A6, see scheme 1).

Rf (95/5 $CH_2Cl_2$/acetone)=0.3

$^1$H NMR ($CDCl_3$, 400 MHz), 1.35 ppm (8H, m); 1.7 ppm (3H, m); 1.95 ppm (2H, m); 2.7 ppm (1H, m); 4.3 ppm (2H, q); 6.6 ppm (1H, s); 11.8 ppm (1H, m).

Step 3:

According to M3, 12.77 g (54.93 mmol) of copper(II) nitrate hemipentahydrate (2.5 $H_2O$) and 100 ml of trifluoroacetic anhydride are introduced into a round-bottomed flask, the mixture is stirred under nitrogen for 5 min and 11.1 g of compound A6 (see scheme 1) (49.93 mmol) dissolved in 100 ml of chloroform are then added. This mixture is refluxed, with stirring and under nitrogen, for 5 hours. After evaporation to dryness, 18.6 g of a blueish oil are obtained. This product is taken up in 200 ml of HCl (10%) and then extracted with ether (3 times 300 ml) and the organic phase is dried and concentrated to give 16.1 g of a colourless oil. This product is purified by flash chromatography (98/2 $CH_2Cl_2$/acetone) to give 7.1 g (53%) of a white powder (compound A7, see scheme 1).

Rf (97/3 $CH_2Cl_2$/acetone)=0.3

$^1$H NMR ($CDCl_3$, 400 MHz), 1.40 ppm (8H, m); 1.8 ppm (3H, m); 2.0 ppm (2H, m); 3.3 ppm (1H, m); 4.4 ppm (2H, q); 8.85 ppm (1H, m).

Step 5:

According to M4, 1.02 g (3.81 mmol) of compound A7 (see scheme 1) and 0.5 ml (3.81 mmol) of diethyl sulphate are introduced into a round-bottomed flask and the mixture is then refluxed, with stirring and under nitrogen, for 1 h 30 min. After cooling to room temperature, 6 g of ice and 15 ml of HCl (1.2N) are added and this mixture is stirred and then extracted with dichloromethane (3 times 40 ml). The organic phase is dried and concentrated to give 1.1 g of a colourless oil. The product is purified by flash chromatography (5/5 $CH_2Cl_2$/heptane) to give 0.53 g (53%) of a white powder (compound A5, see scheme 1).

Rf (9/1 cyclohexane/ethyl acetate)=0.3

$^1$H NMR ($CDCl_3$, 400 MHz), 1.4 ppm (11H, m); 1.8 ppm (3H, m); 1.95 ppm (2H, m); 3.1 ppm (1H, m); 4.25 ppm (2H, q); 4.5 ppm (2H, q).

Step 6:

5.07 g (17.16 mmol) of compound A5 (see scheme 1) are dissolved in 20 ml of methanol, followed by addition of a solution of 1.03 g (25.75 mmol) of sodium hydroxide in 20 ml of water. This mixture is stirred at RT for 2 h. After evaporating off the methanol, the residue is taken up in $CH_2Cl_2$ and an identical volume of water is added, followed by addition of concentrated (36%) hydrochloric acid to acidic pH, with stirring. The organic phase is dried over $Na_2SO_4$ and concentrated to give 4.6 g (100%) of a white powder (compound A, see scheme 1).

$^1$H NMR ($CDCl_3$, 400 MHz), 1.1 ppm to 1.5 ppm (8H, m); 3.0 ppm (1H, m); 4.5 ppm (2H, q); 8.4 ppm (1H, m)

Step 7:

According to M9, 0.48 g (1.8 mmol) of 5-cyclohexy1-2-ethyl-4-nitro-2H-pyrazole-3-carboxylic acid (A) is reacted with 0.31 g (1.8 mmol) of 2-aminoacetophenone hydrochloride to give a crude amide of type C (see scheme 1).

MS (ES+), m/z=384.9

Step 8:

According to M12, 0.69 g (1.8 mmol) of the amide C (see scheme 1) is refluxed in ethanol with 3.46 g (5 eq.) of tin chloride dihydrate to give 0.103 g (17%) of the expected product D (see Scheme 1).

MS (ES+), m/z=337

$^1$H NMR ($CDCl_3$, 400 MHz), 8.0 ppm (2H, m); 7.4 ppm (3H, m); 7.1 ppm (1H, m); 4.5 ppm (2H, q); 4.1 ppm (2H, d); 3.0 ppm (1H, m); 2.0 ppm (2H, m); 1.8 ppm (2H, m); 1.7 ppm (2H, m); 1.5 ppm to 1.2 ppm (7H, m).

Example 73

3-Cyclohexyl-1-ethyl-5-pyrid-4-yl-6,7-dihydro-1H-pyrazolo-[4,3-e][1,4]diazepin-8-one (R1=cyclohexyl; R2=ethyl; R3=4-pyridyl)

Synthesis of the Pyrazole: See Steps 1, 2, 3, 5 and 6 of Example 72

Step 7:

According to M9, 0.48 g (1.8 mmol) of 5-cyclohexylethyl-4-nitro-2H-pyrazole-3-carboxylic acid is reacted with 0.376 g (1.8 mmol) of 2-amino-1-pyrid-4-ylethanone hydrochloride (J. Med. Chem., 38, 17, 3342–3350, 1995; J. Amer. Chem. Soc., 67, 1468–1472, 1945) to give a crude amide of type C (see scheme 1).

MS (ES+), m/z=385.9

Step 8:

According to M12, 0.63 g (1.63 mmol) of the amide C (see scheme 1) is refluxed in ethanol with 3.12 g (5 eq.) of tin chloride dihydrate to give 0.092 g (15%) of the expected product D (see Scheme 1).

m.p.: 126–127° C.

MS (ES+), m/z=338

$^1$H NMR ($CDCl_3$, 400 MHz), 8.6 ppm (2H, d); 7.7 ppm (2H, d); 7.4 ppm (1H, t); 4.5 ppm (2H, q); 4.0 ppm (2H, d); 2.9 ppm (1H, m); 1.9 ppm (2H, m); 1.8 ppm (2H, m); 1.6 ppm (2H, m); 1.4 ppm (3H, m); 1.3 ppm (4H, m).

Example 74

3-Cyclohexyl-5-phenyl-1-propyl-6,7-dihydro-1H-pyrazolo-[4,3-e][1,4]diazepin-8-one (R1=cyclohexyl; R2=propyl; R3=phenyl)

Synthesis of the Pyrazole: See Steps 1, 2 and 3 of Example 72 and the Following Steps 5 and 6.

Step 5:

According to M5, 2.07 g (28.06 mmol) of $Li_2CO_3$ are added, under a stream of nitrogen, to a solution of 3 g (11.22 mmol) of compound A7 (see scheme 1) in 60 ml of anhydrous DMF, followed by addition of 2.73 ml (28.06 mmol) of iodopropane. The reaction medium is heated at 60° C. for 48 h. After cooling to room temperature, the mixture is poured into 100 ml of HCl (1.2N) and the exothermicity is controlled by an ice bath. This mixture is extracted with dichloromethane (3 times 100 ml) and the organic phase obtained is washed with saturated NaCl solution (100 ml), dried over $Na_2SO_4$ and concentrated to give 3.6 g of an oily compound. This product is purified by flash (gradient: 70/30 to 30/70 heptane/$CH_2Cl_2$) to give 2.85 g (82%) of a colourless oil which crystallizes (compound A5, see scheme 1).

Rf (60/40 heptane/$CH_2Cl_2$)=0.3

$^1$H NMR ($CDCl_3$, 400 MHz), 0.9 ppm (3H, t); 1.45 ppm (6H, m); 1.5 ppm (2H, m); 2.85 ppm (7H, m); 3.1 ppm (1H, q); 4.1 ppm (2H, q); 4.4 ppm (2H, q)

Step 6:

2.85 g (9.21 mmol) of compound A5 (see scheme 1) are dissolved in 10 ml of methanol, followed by addition of a solution of 0.55 g (13.81 mmol) of sodium hydroxide in 10 ml of water. The mixture is stirred at RT for 2 h. After evaporating off the methanol, the residue is taken up in $CH_2Cl_2$ and an identical volume of water is added, followed by addition of concentrated (36%) hydrochloric acid to acidic pH, with stirring. The organic phase is dried over $Na_2SO_4$ and concentrated to give 2.52 g (97%) of a white powder (compound A, see scheme 1).

$^1$H NMR ($CDCl_3$, 400 MHz), 0.9 ppm (3H, m); 1.2 ppm to 1.6 ppm (5H, m); 1.7 ppm to 2.0 ppm (7H, m); 3.1 ppm (1H, m); 4.4 ppm (2H, q); 8.7 ppm (1H, m)

Step 7:

According to M9, 0.5 g (1.8 mmol) of 5-cyclohexyl-4-nitro-2-propyl-2H-pyrazole-3-carboxylic acid is reacted with 0.31 g (1.8 mmol) of 2-aminoacetophenone hydrochloride to give a crude amide of type C (see Scheme 1).

MS (ES+), m/z=399

Step 8:

According to M12, 0.72 g (1.8 mmol) of the amide C (see scheme 1) is refluxed in ethanol with 3.59 g (5 eq.) of tin chloride dihydrate to give 0.172 g (27%) of the expected product D (see Scheme 1).

MS (ES+), m/z=351

$^1$H NMR ($CDCl_3$, 400 MHz ), 7.8 ppm (2H, m); 7.4 ppm (4H, m); 4.5 ppm (2H, q); 4.0 ppm (2H, d); 2.9 ppm (1H, m); 1.9 ppm to 1.7 ppm (10H, m); 1.3 ppm (2H, m); 0.9 ppm (3H, t).

Example 75

3-Cyclohexyl-1-propyl-5-pyrid-4-yl-6, 7-dihydro-1H-pyrazolo-[4,3-e][1,4]diazepin-8-one (R1=cyclohexyl; R2=propyl; R3=4-pyridyl)

Synthesis of the Pyrazole: See Steps 1, 2, 3, 5 and 6 of Example 74

Step 7:

According to M9, 0.5 g (1.8 mmol) of 5-cyclohexyl-4-nitro-2-propyl-2H-pyrazole-3-carboxylic acid is reacted with 0.376 g (1.8 mmol) of 2-amino-1-pyrid-4-ylethanone hydrochloride (*J. Med. Chem.*, 38, 17, 3342–3350, 1995; *J. Amer. Chem. Soc.*, 67, 1468–1472, 1945) to give a crude amide of type C (see Scheme 1).

MS (ES+), m/z=400

Step 8:

According to M12, 0.65 g (1.63 mmol) of the amide C (see scheme 1) is refluxed in ethanol with 3.24 g (5 eq.) of tin chloride dihydrate to give 0.055 g (8.6%) of the expected product D (see Scheme 1).

m.p.: 152–1530° C.

MS (ES+), m/z=352

$^1$H NMR (CDCl$_3$, 400 MHz), 8.7 ppm (2H, d); 7.7 ppm (2H, d); 6.9 ppm (1H, t); 4.4 ppm (2H, m); 4.5 ppm (2H, d); 2.9 ppm (1H, m); 1.9 ppm to 1.6 ppm (1OH, m); 1.3 ppm (2H, m); 0.8 ppm (3H, t).

Example 76

3-Cyclohexylmethyl-1-ethyl-5-pyrid-4-yl-6,7-dihydro-1H-pyrazolo[4,3-e][1,4]diazepin-8-one (R1=cyclohexylmethyl; R2=ethyl; R3=4-pyridyl)

Synthesis of the Pyrazole: See the Following Steps 1, 2, 5, 3 and 6.

Step 1:

4.33 g (188.26 mmol) of sodium are dissolved portionwise in 200 ml of anhydrous ethanol under nitrogen at room temperature. 25.6 ml (188.26 mmol) of diethyl oxalate in 50 ml of anhydrous ethanol are added. 24 g (171.11 mmol) of acetonylcyclohexane are added. The reaction mixture is refluxed for 3 h under nitrogen and with stirring, and is then evaporated to dryness and the residue is taken up in 300 ml of HCl (1.2 N) and then extracted with diethyl ether (3 times 200 ml). The organic phase is dried over sodium sulphate and then concentrated to give 42.6 g (92%) of a colourless oil (compound A1, see scheme 1).

Rf (99/1 CH$_2$Cl$_2$/acetone)=0.5

$^1$H NMR (CDCl$_3$, 400 MHz), 1.0 ppm (2H, m); 1.25 ppm (3H, m); 1.4 ppm (3H, m); 1.7 ppm (6H, m); 1.8 ppm (1H, m); 2.35 ppm (2H, d); 4.4 ppm (2H, q); 6.3 ppm (1H, s); 14.6 ppm (1H, m).

Step 2:

12.9 g (195.4 mmol) of potassium hydroxide are dissolved in 250 ml of water and the reaction medium is cooled to 0° C. 42.6 g (177 mmol) of compound A1 (see scheme 1) are added portionwise and the mixture is stirred for 30 min at 0° C. 25.37 g (195 mmol) of hydrazine sulphate are added and the mixture is then stirred for 45 min at 0° C. The resulting mixture is stirred overnight at room temperature, 200 ml of water are then added and this mixture is extracted with dichloromethane (3 times 200 ml). The organic phase obtained is washed with saturated NaCl solution (1×200 ml) and then dried over sodium sulphate and concentrated. 40 g of an powder are obtained.

The product is purified by flash chromatography (99/1 to 95/5 CH$_2$Cl$_2$/acetone) to give 20.7 g (50%) of a white powder (compound A6, see scheme 1).

Rf (97/3 CH$_2$Cl$_2$/acetone)=0.3

$^1$H NMR (CDCl$_3$, 400 MHz), 0.9 ppm (2H, m); 1.2 ppm (4H, m); 1.4 ppm (3H, m); 1.65 ppm (6H, m); 2.6 ppm (H, d); 6.6 ppm (1H, s); 10.5 ppm (1H, m)

Step 5:

According to M4, 8.5 g (36 mmol) of compound A6 (see scheme 1) and 2.38 ml (18 mmol) of diethyl sulphate are introduced into a round-bottomed flask and the mixture is then heated at 125–130° C., with stirring and under nitrogen, for 4 h. After cooling to room temperature, 120 g of ice and 120 ml of HCl (1.2N) are added with stirring and the resulting mixture is then extracted with dichloromethane (3 times 250 ml). The organic phase is dried and concentrated to give 10.81 g of a brown oil. This product is purified by flash chromatography (9/1 cyclohexane/ethyl acetate) to give 5.76 g (60%) of a white powder (compound A8, see scheme 1).

Rf (80/20 cyclohexane/ethyl acetate)=0.3

$^1$H NMR (CDCl$_3$, 400 MHz), 0.9 ppm (2H, m); 1.2 ppm (4H, m); 1.4 ppm (5H, m); 1.60 ppm (6H, m); 2.5 ppm (2H, d); 4.35 ppm (2H, q); 4.5 ppm (2H, q); 6.6 ppm (1H, s)

Step 3:

According to M3, 20.7 g (89.95 mmol) of copper(II) nitrate hemipentahydrate (2.5 H$_2$O) and 100 ml of trifluoroacetic anhydride are introduced into a round-bottomed flask and the mixture is stirred under nitrogen for 5 min, followed by addition of 17 g of compound A8 (80.87 mmol) dissolved in 100 ml of chloroform. This mixture is refluxed, with stirring and under nitrogen, for 5 hours. This product is purified by flash chromatography (98/2 CH$_2$Cl$_2$/acetone) to give 20 g of a blueish oil. This product is taken up in 200 ml of HCl (1.2N) and then extracted with ether (3 times 300 ml) and the organic phase is dried and concentrated to give 16.81 g (70%) of a colourless oil (compound A5, see scheme 1).

MS (ES+), m/z=309.90

Rf (70/30 heptane/CH$_2$Cl$_2$)=0.3

$^1$H NMR (CDCl$_3$, 400 MHz), 1.0 ppm (2H, m); 1.2 ppm (3H, m); 1.4 ppm (3H, m); 1.45 ppm (3H, m); 1.7 ppm (6H, m); 2.8 ppm (2H, d); 4.3 ppm (2H, q); 4.5 ppm (2H, q)

Step 6:

8.3 g (33.80 mmol) of compound A5 (see scheme 1) are dissolved in 40 ml of methanol, followed by addition of a solution of 2 g (50.7 mmol) of sodium hydroxide in 40 ml of water. This mixture is stirred at RT for 2 h. After evaporating off the methanol, the residue is taken up in CH$_2$Cl$_2$ and an identical volume of water is added, followed by addition of concentrated (36%) HCl to acidic pH, with stirring. The organic phase is dried over Na$_2$SO$_4$ and concentrated to give 7.5 g (98%) of a white powder (compound A, see scheme 1).

$^1$H NMR (CDCl$_3$, 400 MHz), 1.0 ppm (2H, m); 1.2 ppm (3H, m); 1.5 ppm (3H, t); 1.7 ppm (6H, m); 2.8 ppm (2H, d); 4.6 ppm (2H, q); 8.55 ppm (1H, m).

Step 7:

According to M9, 0.281 g (1.8 mmol) of 5-cyclohexylmethyl-2-ethyl-4-nitro-2H-pyrazole-3-carboxylic acid (A) is reacted with 0.376 g (1.8 mmol) of 2-amino-1-pyrid-4-ylethanone hydrochloride (*J. Med. Chem.*, 38, 17, 3342–3350, 1995; *J. Amer. Chem. Soc.*, 67, 1468–1472, 1945) to give a crude amide of type C (see Scheme 1).

MS (ES+), m/z=400.01

Step 8:

According to M12, 0.61 g (1.53 mmol) of the amide C (see scheme 1) is refluxed in ethanol with 3.02 g (5 eq.) of tin chloride dihydrate to give 0.073 g (12%) of the expected product D (see scheme 1).

MS (ES+), m/z=352.32

$^1$H NMR (CDCl$_3$, 400 MHz), 8.7 ppm (2H, d); 7.8 ppm (2H, d); 7.3 ppm (1H, t); 4.6 ppm (2H, q); 4.1 ppm (2H, d); 2.7 ppm (2H, d); 1.7 ppm (6H, m); 1.5 ppm (3H, t); 1.3 ppm to 1.0 ppm (5H, m).

Example 77

3-Cyclohexylmethyl-5-phenyl-1-propyl-6,7-dihydro-1H-pyrazolo[4,3-e][1,4]diazepin-8-one (R1=cyclohexylmethyl; R2=propyl; R3=phenyl)

Synthesis of the Pyrazole: See Steps 1 and 2 of Example 76 and the Following Steps 5, 3 and 6.

Step 5:

According to M5, 3.9 g (52.89 mmol) of Li$_2$CO$_3$ are added, under a stream of nitrogen, to a solution of 5 g (21.16 mmol) of compound A6 (see scheme 1) in 100 ml of anhydrous DMF, followed by addition of 5.2 ml (52.89 mmol) of iodopropane. The reaction medium is heated at 70° C. for 48 h. After cooling to room temperature, the mixture is poured into 100 ml of HCl (1.2N) and the exothermicity is controlled with an ice bath. This mixture is extracted with dichloromethane (3 times 200 ml) and the organic phase obtained is washed with saturated NaCl solution (200 ml), dried over Na$_2$SO$_4$ and evaporated to dryness to give 5.8 g of a brown oil. This product is purified by flash chromatography (gradient: 50/50 to 30/70 heptane/CH$_2$Cl$_2$) to give 1.15 g (20%) of a colourless oil which crystallizes (compound A8, see scheme 1).

Rf (60/40 heptane/CH$_2$Cl$_2$)=0.3

$^1$H NMR (CDCl$_3$, 400 MHz), 0.9 ppm (5H, m); 1.2 ppm (3H, m); 1.4 ppm (3H, m); 1.7 ppm (6H, m); 1.8 ppm (2H, m); 2.5 ppm (2H, d); 4.3 ppm (2H, q); 4.5 ppm (2H, q); 6.6 ppm (1H, s)

Step 3:

According to M3, 0.96 g (4.13 mmol) of copper(II) nitrate hemipentahydrate (2.5 H$_2$O) and 20 ml of trifluoroacetic anhydride are introduced into a round-bottomed flask and the mixture is stirred under nitrogen for 5 min, followed by addition of 1.15 g of compound A8 (see scheme 1) (4.13 mmol) dissolved in 20 ml of chloroform. This mixture is refluxed, with stirring and under nitrogen, for 3 hours. This product is taken up in 10 g of ice and 40 ml of HCl (10%) and then extracted with dichloromethane (3 times 100 ml) and the organic phase is dried and concentrated to give 1.3 g of a colourless oil. The product is purified by flash chromatography (gradient: 70/30 to 50/50 heptane/CH$_2$Cl$_2$) to give 1.08 g (80%) of a white powder (compound A5, see scheme 1).

Rf (60/40 heptane/CH$_2$Cl$_2$)=0.3

$^1$H NMR (CDCl$_3$, 400 MHz), 0.9 ppm (3H, m); 1.0 ppm to 1.3 ppm (5H, m); 1.4 ppm (3H, m); 1.7 ppm (6H, m); 1.9 ppm (2H, m); 2.7 ppm (2H, d); 4.1 ppm (2H, t); 4.5 ppm (2H, q)

Step 6:

1 g (3.09 mmol) of compound A5 (see scheme 1) is dissolved in 5 ml of methanol, followed by addition of a solution of 0.185 g (4.64 mmol) of sodium hydroxide in 5 ml of water. This mixture is stirred at RT for 2 h. After evaporating off the methanol, the residue is taken up in CH$_2$Cl$_2$ and an identical volume of water is added, followed by addition of concentrated (36%) hydrochloric acid to acidic pH, with stirring. The organic phase is dried over Na$_2$SO$_4$ and concentrated to dryness to give 0.89 g (97%) of a white powder (compound A, see scheme 1).

$^1$H NMR (CDCl$_3$, 400 MHz), 0.9 ppm to 1.0 ppm (5H, m); 1.2 ppm (3H, m); 1.4 ppm (3H, m); 1.6 ppm (6H, m); 1.9 ppm (2H, m); 2.7 ppm (2H, d); 4.1 ppm (2H, t); 4.5 ppm (2H, q)

Step 7:

According to M9, 0.463 g (1.57 mmol) of 5-cyclohexylmethyl-4-nitro-2-propyl-2H-pyrazole-3-carboxylic acid (A) is reacted with 0.269 g (1.57 mmol) of 2-aminoacetophenone hydrochloride to give a crude amide of type C (see scheme 1).

MS (ES+), m/z=413.04

Step 8:

According to M12, 0.65 g (1.57 mmol) of the amide C (see scheme 1) is refluxed in ethanol with 3.24 g (5 eq.) of tin chloride dihydrate to give 0.092 g (14%) of the expected product D (see scheme 1).

MS (ES+), m/z=364.90

$^1$H NMR (CDCl$_3$, 400 MHz), 8.0 ppm (2H, m); 7.5 ppm (3H, m); 6.4 ppm (1H, s); 4.5 ppm (2H, m); 4.1 ppm (2H, d); 2.7 ppm (2H, d); 1.9 ppm (2H, m); 1.7 ppm (6H, m); 1.3 ppm to 0.8 ppm (8H, m).

Example 78

3-Cyclohexylmethyl-1-propyl-5-pyrid-4-yl-6,7-dihydro-1H-pyrazolo[4,3-e][1,4]diazepin-8-one (R1=cyclohexylmethyl; R2=propyl; R3=4-pyridyl)

Synthesis of the Pyrazole: See Steps 1, 2, 5, 3 and 6 of Example 77

Step 7:

According to M9, 0.464 g (1.57 mmol) of 5-cyclohexylmethyl-4-nitro-2-propyl-2H-pyrazole-3-carboxylic acid (A) is reacted with 0.328 g (1.57 mmol) of 2-amino-1-pyrid-4-ylethanone hydrochloride (*J. Med. Chem.*, 38, 17, 3342–3350, 1995; *J. Amer. Chem. Soc.*, 67, 1468–1472, 1945) to give a crude amide of type C (see Scheme 1).

MS (ES+), m/z=414.02

Step 8:

According to M12, 0.59 g (1.43 mmol) of the amide C (see scheme 1) is refluxed in ethanol with 2.92 g (5 eq.) of tin chloride dihydrate to give 0.101 g (15.4%) of the expected product D (see Scheme 1).

MS (ES+), m/z=366.38

$^1$H NMR (CDCl$_3$, 400 MHz), 8.7 ppm (2H, d); 7.7 ppm (2H, d); 6.9 ppm (1H, m); 4.5 ppm (2H, m); 4.0 ppm (2H, d); 2.7 ppm (2H, d); 1.8 ppm (3H, m); 1.7 ppm (5H, m); 1.0 ppm to 0.8 ppm (8H, m).

Example 79

3-Cyclohexylmethyl-1-ethyl-5-phenyl-6,7-dihydro-1H-pyrazolo[4,3-e][1,4]diazepin-8-one (R1=cyclohexylmethyl; R2=ethyl; R3=phenyl)

Synthesis of the Pyrazole: See Steps 1, 2, 5, 3 and 6 of Example 76

Step 5:

According to M4, 8.5 g (36 mmol) of compound A6 (see scheme 1) and 2.38 ml (18 mmol) of diethyl sulphate are introduced into a round-bottomed flask and the mixture is then heated at 125–130° C., with stirring and under nitrogen, for 4 h. After cooling to room temperature, 120 g of ice and 120 ml of HCl (1.2N) are added and the resulting mixture is stirred and then extracted with dichloromethane (3 times 250 ml). The organic phase is dried and concentrated to give 10.81 g of a brown oil. This product is purified by flash chromatography (9/1 cyclohexane/ethyl acetate) to give 5.76 g (60%) of a white powder (compound A8, see scheme 1).

Rf (80/20 cyclohexane/ethyl acetate)=0.3

$^1$H NMR (CDCl$_3$, 400 MHz), 0.9 ppm (2H, m); 1.2 ppm (4H, m); 1.4 ppm (5H, m); 1.6 ppm (6H, m); 2.5 ppm (2H, d); 4.35 ppm (2H, q); 4.5 ppm (2H, q); 6.6 ppm (1H, s)

Step 3:

According to M3, 20.7 g (89.95 mmol) of copper(II) nitrate hemipentahydrate (2.5 H$_2$O) and 100 ml of trifluoroacetic anhydride are introduced into a round-bottomed flask, this mixture is stirred under nitrogen for 5 min and 17 g of compound A8 (see scheme 1) (80.87 mmol) dissolved in 100 ml of chloroform are then added. This mixture is refluxed, with stirring and under nitrogen, for 5 hours. This product is purified by flash chromatography (98/2 CH$_2$Cl$_2$/acetone) to give 20 g of a blueish oil. This product is taken up in 200 ml of HCl (10%) and then extracted with ether (3 times 300 ml) and the organic phase is dried and concentrated to give 16.81 g (70%) of a colourless oil (compound A5, see scheme 1).

MS (ES+), m/z=309.90

Rf (70/30 heptane/$CH_2Cl_2$)=0.3

$^1$H NMR ($CDCl_3$, 400 MHz), 1.0 ppm (2H, m); 1.2 ppm (3H, m); 1.4 ppm (3H, m); 1.45 ppm (3H, m); 1.7 ppm (6H, m); 2.8 ppm (2H, d); 4.3 ppm (2H, q); 4.5 ppm (2H, q)

Step 6:

8.3 g (33.80 mmol) of compound A5 (see scheme 1) are dissolved in 40 ml of methanol, followed by addition of a solution of 2 g (50.7 mmol) of sodium hydroxide in 40 ml of water. This mixture is stirred at RT for 2 h. After evaporating off the methanol, the residue is taken up in $CH_2Cl_2$ and an identical volume of water is added, followed by addition of concentrated (36%) of hydrochloric acid to acidic pH, with stirring. The organic phase is dried over $Na_2SO_4$ and concentrated to dryness to give 7.5 g (98%) of a white powder (compound A, see scheme 1).

$^1$H NMR ($CDCl_3$, 400 MHz), 1.0 ppm (2H, m); 1.2 ppm (3H, m); 1.5 ppm (3H, t); 1.7 ppm (6H, m); 2.8 ppm (2H, d); 4.6 ppm (2H, q); 8.55 ppm (1H, m)

Step 7:

According to M9, 0.281 g (1.8 mmol) of 5-cyclohexylmethyl-2-ethyl-4-nitro-2H-pyrazole-3-carboxylic acid (A) is reacted with 0.309 g (1.8 mmol) of 2-aminoacetophenone hydrochloride to give a crude amide of type C (see scheme 1).

MS (ES+), m/z=399.60

Step 8:

According to M12, 0.72 g (1.8 mmol) of the amide C (see scheme 1) is refluxed in ethanol with 3.59 g (5 eq.) of tin chloride dihydrate to give 0.132 g (21%) of the expected product D (see scheme 1).

MS (ES+), m/z=350.9

$^1$H NMR ($CDCl_3$, 400 MHz), 7.9 ppm (2H, m); 7.4 ppm (3H, m); 7.1 ppm (1H, m); 4.5 ppm (2H, t); 4.0 ppm (2H, d); 2.6 ppm (2H, d); 1.9 ppm (3H, m); 1.6 ppm (5H, m); 1.4 ppm (3H, m); 1.1 ppm (3H, m); 0.9 ppm (2H, m).

Example 80

5-tert-Butyl-1-ethyl-3-isopropyl-6,7-dihydro-1H-pyrazolo-[4,3-e][1,4]diazepin-8-ylidenecyanamide (R1=isopropyl; R2=ethyl; R3=tert-butyl)

Step 10:

According to M13, 0.96 g (3.28 mmol) of 5-tert-butyl-1-ethyl-3-isopropyl-6,7-dihydro-1H-pyrazolo[4,3-e][1,4]-diazepin-8-thione is reacted with 0.0984 g of 80% sodium hydride in refluxing THF for 1 h, followed by addition, at room temperature, of 0.245 ml of methyl iodide. The mixture is refluxed for 2 h to give 1.14 g of the expected methylsulphanyl G (see scheme 1).

Rf (95/5 $CH_2Cl_2$/acetone)=0.85

MS (ES+), m/z=307

Step 11:

1 g (3.26 mmol) of the methylsulphanyl G (see scheme 1) is reacted with 0.27 g (2 eq.) of cyanamide to give 0.825 g (84%) of the expected product of type F (see Scheme 1).

Rf (95/5 $CH_2Cl_2$/methanol)=0.56 m.p.=243° C.

MS (ES+), m/z=301

$^1$H NMR ($CDCl_3$, 400 MHz), 8.6 ppm (1H, bs); 4.5 ppm (2H, q); 3.7 ppm (2H, bs); 3.2 ppm (1H, m); 1.4 ppm (3H, t); 1.3 ppm (6H, d); 1.25 ppm (9H, s)

Example 81

1-Ethyl-3-isopropyl-5-p-tolyl-6,7-dihydro-1H-pyrazolo-[4,3-e][1,4]diazepin-8-ylidenecyanamide (R1=isopropyl; R2=ethyl; R3=p-tolyl)

Step 10:

According to M13, 0.61 g (1.87 mmol) of 1-ethyl-3-isopropyl-5-p-tolyl-6,7-dihydro-1H-pyrazolo[4,3-e][1,4]-diazepin-8-thione is reacted with 0.056 g of 80% sodium hydride in refluxing THF for 1 h, followed by addition, at room temperature, of 0.14 ml of methyl iodide. The mixture is refluxed for 2 h to give 0.71 g of the expected methylsulphanyl G (see scheme 1).

Rf (95/5 $CH_2Cl_2$/acetone)=0.78

MS (ES+), m/z=341

Step 11:

0.64 g (1.87 mmol) of the methylsulphanyl G (see scheme 1) is reacted with 0.16 g (2 eq.) of cyanamide to give 0.43 g (69%) of the expected product of type F (see Scheme 1).

Rf (95/5 $CH_2Cl_2$/methanol)=0.48 m.p.=245° C.

MS (ES+), m/z=335

$^1$H NMR ($CDCl_3$, 400 MHz), 8.8 ppm (1H, bs); 8.0 ppm (2H, d); 7.3 ppm (2H, d); 4.6 ppm (2H, q); 4.15 ppm (2H, bs); 3.3 ppm. (1H, m); 2.4 ppm (3H, s); 1.5 ppm (3H, t); 1.4 ppm (6H, d)

Example 82

1-Ethyl-3-isopropyl-5-(4-methoxyphenyl)-6,7-dihydro-1H-pyrazolo[4,3-e][1,4]diazepin-8-one (R1=isopropyl; R2=ethyl; R3=4-methoxyphenyl)

Step 7:

According to M10, 3.18 g (14 mmol) of 2-ethyl-5-isopropyl-4-nitro-2H-pyrazole-3-carboxylic acid (A) are reacted with 2.82 g (14 mmol) of 2-amino-1-(4-methoxyphenyl)ethanone hydrochloride to give 4.7 g (90%) of an amide of type C (see Scheme 1).

MS (ES+), m/z=375

$^1$H NMR ($CDCl_3$, 400 MHz), 8.0 ppm (2H, d); 7.7 ppm (1H, t); 7.0 ppm (2H, d); 4.95 ppm (2H, d); 4.25 ppm (2H, q); 3.9 ppm (3H, s); 3.55 ppm (1H, m); 1.5 ppm (3H, t); 1.3 ppm (GH, d)

Step 8:

According to M12, 4.7 g (12.5 mmol) of the amide C (see scheme 1) are refluxed in ethanol with 14.2 g of tin chloride dihydrate to give 2.84 g (70%) of the expected product D (see Scheme 1).

MS (ES+), m/z=327

Rf (95/5 $CH_2Cl_2$/MeOH)=0.22 m.p.=150° C.

$^1$H NMR (DMSO, 400 MHz), 8.25 ppm (1H, t); 8.0 ppm (2H, d); 7.05 ppm (2H, d); 4.45 ppm (2H, q); 4 ppm (2H, d); 3.85 ppm (3H, s); 3.2 ppm (1H, m); 1.35 ppm (3H, t); 1.3 ppm (6H, d)

Example 83

Step 9:

1-Ethyl-5-(4-methoxyphenyl)-3-methyl-6,7-dihydro-1H-pyrazolo[4,3-e][1,4]diazepin-8-thione (R1=methyl; R2=ethyl; R3=4-methoxyphenyl) 2.2 g (7.4 mmol) of 1-ethyl-5-(4-methoxyphenyl)-3-methyl-6,7-dihydro-1H-pyrazolo[4,3-e][1,4]diazepin-8-one are refluxed in toluene with 6 g (14.8 mmol) of Lawesson's reagent to give 2 g (87%) of an expected compound of type E (see Scheme 1).

Rf (95/5 $CH_2Cl_2$/methanol)=0.7 m.p.: 209° C.

MS (ES+), m/z=315

¹H NMR (CDCl₃, 400 MHz), 8.35 ppm (1H, bs); 7.95 ppm (2H, d); 6.95 ppm (2H, d); 4.8 ppm (2H, q); 4.15 ppm (2H, bs); 3.9 ppm (3H, s); 2.4 ppm (3H, s); 1.5 ppm (3H, t)

Example 84

1-Ethyl-3-methyl-5-(4-methoxyphenyl)-6,7-dihydro-1H-pyrazolo[4,3-e][1,4]diazepin-8-ylidenecyanamide (R1=methyl; R2=ethyl; R3=4-methoxyphenyl)
Step 10:

According to M13, 1.75 g (5.6 mmol) of 1-ethyl-5-(4-methoxyphenyl)-3-methyl-6,7-dihydro-1H-pyrazolo[4,3-e][1,4]diazepin-8-thione are reacted with 0.23 g of 60% sodium hydride in refluxing THF for 1 h, followed by addition, at room temperature, of 0.42 ml of methyl iodide. The mixture is refluxed for 2 h to give 2 g (100%) of the expected methylsulphanyl G (see Scheme 1).

Rf (95/5 CH₂Cl₂/methanol)=0.86
MS (ES+), m/z=329
Step 11:

2g (6.1 mmol) of the methylsulphanyl G (see Scheme 1) are reacted with 0.52 g (2 eq.) of cyanamide to give 1.33 g (68%) of the expected product of type F (see scheme 1).

Rf (95/5 CH₂Cl₂/methanol)=0.5
m.p.=265° C.
MS (ES+), m/z=323
¹H NMR (DMSO, 400 MHz), 9.45 ppm (1H, bs); 8.1 ppm (2H, d); 7.1 ppm (2H, d); 4.45 ppm (2H, q); 4.15 ppm (2H, bs); 3.85 ppm (3H, s); 2.3 ppm (3H, s); 1.35 ppm (3H, t)

Example 85

3-Isopropyl-5-(4-methoxyphenyl)-1-propyl-6,7-dihydro-1H-pyrazolo[4,3-e][1,4]diazepin-8-one (R1=isopropyl; R2=propyl; R3=4-methoxy-phenyle)
Step 7:

According to M10, 3.38 g (14 mmol) of 5-isopropyl-4-nitro-2-propyl-2H-pyrazole-3-carboxylic acid (A) are reacted with 2.82 g (14 mmol) of 2-amino-1-(4-methoxyphenyl)ethanone hydrochloride to give 4.58 g (84%) of an amide of type C (see scheme 1).

MS (ES+), m/z=389
¹H NMR (CDCl₃, 400 MHz), 8.0 ppm (2H, d); 7.7 ppm (1H, t); 7.0 ppm (2H, d); 4.95 ppm (2H, d); 4.2 ppm (2H, q); 3.9 ppm (3H, s); 3.55 ppm (1H, m); 1.9 ppm (2H, m); 1.3 ppm (6H, d); 0.95 ppm (3H, t)
Step 8:

According to M12, 4.58 g (16 mmol) of the amide C (see scheme 1) are refluxed in ethanol with 13.3 g of tin chloride dihydrate to give 2.92 g (73%) of the expected product D (see scheme 1).

MS (ES+), m/z=341
¹H NMR (DMSO, 400 MHz), 8.2 ppm (1H, t); 8.0 ppm (2H, d); 7.05 ppm (2H, d); 4.4 ppm (2H, q); 4.0 ppm (211, d); 3.85 ppm (3H, s); 3.2 ppm (1H, m); 1.8 ppm (2H, m); 1.3 ppm (6H, d); 0.85 ppm (3H, t)
Rf (90/10 CH₂Cl₂/acetone)=0.37
m.p.=142° C.

Example 86

3-tert-Butyl-1-ethyl-5-(4-methoxyphenyl)-6,7-dihydro-1H-pyrazolo[4,3-e][1,4]diazepin-8-one (R1=tert-butyl; R2=ethyl; R3=4-methoxyphenyl)
Step 7:

According to M10, 3.38 g (14 mmol) of 5-tert-butyl-2-ethyl-4-nitro-2H-pyrazole-3-carboxylic acid (A) are reacted with 2.82 g (14 mmol) of 2-amino-1-(4-methoxyphenyl)ethanone hydrochloride to give 4.92 g (90%) of an amide of type C (see scheme 1).

MS (ES+), m/z=389
¹H NMR (CDCl₃, 400 MHz), 8.0 ppm (2H, d); 7.4 ppm (1H, bs); 7.0 pm (2H, d); 4.9 ppm (2H, d); 4.2 ppm (2H, q); 3.9 ppm (3H, s); 1.5 ppm (3H, t); 1.4 ppm (9H, s)
Step 8:

According to M12, 4.92 g (13 mmol) of the amide C (see scheme 1) are refluxed in ethanol with 14.3 g of tin chloride hydrate to give 2.1 g (49%) of the expected product D (see scheme 1).

MS (ES+), m/z=341
Rf (90/10 CH₂Cl₂/acetone)=0.32
m.p.=180° C.
¹H NMR (DMSO, 400 MHz), 8.3 ppm (1H, t); 8.0 ppm (2H, d); 7.1 ppm (2H, d); 4.4 ppm (2H, q); 4.0 ppm (2H, d); 3.85 ppm (3H, s); 1.45 ppm (9H, s); 1.35 ppm (3H, t)

Example 87

3-tert-Butyl-5-(4-methoxyphenyl)-1-propyl-6,7-dihydro-1H-pyrazolo[4,3-e][1,4]diazepin-8-one (R1=tert-butyl; R2=propyl; R3=4-methoxyphenyl)
Step 7:

According to M10, 3.57 g (14 mmol) of 5-tert-butyl-4-nitro-2-propyl-2H-pyrazole-3-carboxylic acid (A) are reacted with 2.82 g (14 mmol) of 2-amino-1-(4-methoxyphenyl)ethanone hydrochloride to give 5 g (89%) of an amide of type C (see scheme 1).

MS (ES+), m/z =403
¹H NMR (CDCl₃, 400 MHz), 8.0 ppm (2H, d); 7.4 ppm (1H, t); 6.95 ppm (2H, d); 4.9 ppm (2H, d); 4.1 ppm (2H, q); 3.9 ppm (3H, s); 1.9 ppm (2H, m); 1.4 ppm (9H, s); 0.9 ppm (3H, t)
Step 8:

According to M12, 5 g (12 mmol) of the amide C (see scheme 1) are refluxed in ethanol with 14 g of tin chloride dihydrate to give 2.77 g (63%) of the expected product D (see scheme 1).

MS (ES+), m/z =355
Rf (90/10 CH₂Cl₂/acetone)=0.37
m.p.=167° C.
¹H NMR (DMSO, 400 MHz), 8.3 ppm (1H, t); 8.0 ppm (2H, d); 7.1 ppm (2H, d); 4.4 ppm (2H, q); 4.0 ppm (2H, d); 3.85 ppm (3H, s); 1.8 ppm (2H, m); 1.4 ppm (9H, s); 0.85 ppm (3H, t)

Example 88

1-Ethyl-3-methyl-5-(4-hydroxyphenyl)-6,7-dihydro-1H-pyrazolo[4,3-e][1,4]diazepin-8-ylidenecyanamide (R1=methyl; R2=ethyl; R3=4-hydroxyphenyl)

0.4 g (1.24 mmol) of 1-ethyl-3-methyl-5-(4-methoxyphenyl)-6,7-dihydro-1H-pyrazolo[4,3-e][1,4]diazepin-8-ylidene-cyanamide is refluxed in dichloromethane with 31 ml of a molar solution of BBr₃ in dichloromethane to give 0.14 g (37%) of the expected product.

MS (ES+) m/z=309
m.p.=300° C.
Rf (90/10 CH₂Cl₂/MeOH)=0.55
¹H NMR (DMSO, 400 MHz), 10.15 ppm (1H, s); 9.45 ppm (1H, bs); 8.0 ppm (2H, d); 6.9 ppm (2H, d); 4.45 ppm (2H, q); 4.1 ppm (2H, bs); 2.3 ppm (3H, s); 1.35 ppm (3H, t);

Example 89

(±)3-sec-Butyl-1-ethyl-5-(4-methoxyphenyl)-6,7-dihydro-1H-pyrazolo[4,3-e][1,4]diazepin-8-one
(R1=sec-butyl; R2=ethyl; R3=4-methoxyphenyl)
Step 7:

According to M10, 3.38 g (14 mmol) of 2-ethyl-5-sec-butyl-4-nitro-2H-pyrazole-3-carboxylic acid (A) are reacted with 2.82 g (14 mmol) of 2-amino-1-(4-methoxyphenyl)ethanone hydrochloride to give 4.69 g (86%) of an amide of type C (see scheme 1).

MS (ES+), m/z=389
$^1$H NMR (CDCl$_3$, 400 MHz), 8.0 ppm (2H, d); 7.7 ppm (1H, t); 7.0 ppm (2H, d); 4.95 ppm (2H, d); 4.3 ppm (2H, q); 3.9 ppm (3H, s); 3.4 ppm (1H, m); 1.85 ppm (1H, m); 1.65 ppm (1H, m); 1.5 ppm (3H, t); 1.3 ppm (3H, d); 0.9 ppm (3H, t)
Step 8:

According to M12, 4.69 g (12 mmol) of the amide C (see scheme 1) are refluxed in ethanol with 13.6 g of tin chloride dihydrate to give 2.85 g (69%) of the expected product D (see scheme 1).

MS (ES+), m/z=341
$^1$H NMR (DMSO, 400 MHz), 8.25 ppm (1H, t); 8 ppm (2H, d); 7.05 ppm (2H, d); 4.45 ppm (2H, q); 4 ppm (2H, d); 3.8 ppm (3H, s); 3 ppm (1H, m); 1.75 ppm (1H, m); 1.65 ppm (1H, m); 1.35 ppm (3H, t); 1.25 ppm (3H, d); 0.8 ppm (3H, t)
Rf (90/10 CH$_2$Cl$_2$/acetone)=0.29
m.p.=50° C.

Example 90

(±)3-sec-Butyl-5-(4-methoxyphenyl)-1-propyl-6,7-dihydro-1H-pyrazolo[4,3-e][1,4]diazepin-8-one
(R1=sec-butyl; R2=propyl; R3=4-methoxy-phenyle)
Step 7:

According to M10, 3.57 g (14 mmol) of 5-sec-butyl-4-nitro-2-propyl-2H-pyrazole-3-carboxylic acid (A) are reacted with 2.82 g (14 mmol) of 2-amino-1-(4-methoxyphenyl)ethanone hydrochloride to give 4.77 g (85%) of an amide of type C (see scheme 1).

MS (ES+), m/z=403
$^1$H NMR (CDCl$_3$, 400 MHz), 8.0 ppm (2H, d); 7.7 ppm (1H, t); 7.0 ppm (2H, d); 4.95 ppm (2H, d); 4.2 ppm (2H, q); 3.9 ppm (3H, s),; 3.4 ppm (1H, m); 1.9 ppm (3H, m); 1.6 ppm (1H, m); 1.3 ppm (3H, d); 0.9 ppm (6H, m)
Step 8:

According to M12, 4.77 g (12 mmol) of the amide C (see scheme 1) are refluxed in ethanol with 13.4 g of tin chloride dihydrate to give 2.37 g (56%) of the expected product D (see scheme 1).

Rf (90/10 CH$_2$Cl$_2$/acetone)=0.37
m.p.=85° C.
MS (ES+), m/z=355
$^1$H NMR (DMSO, 400 MHz), 8.25 ppm (1H, t); 8.0 ppm (2H, d); 7.05 ppm (2H, d); 4.4 ppm (2H, q); 4.0 ppm (2H, m); 3.8 ppm (3H, s); 3.0 ppm (1H, m); 1.75 ppm (3H, m); 1.65 ppm (1H, m); 1.25 ppm (3H, d); 0.8 ppm (6H, m)

Example 91

1-Ethyl-3-methyl-5-(3,4,5-trimethoxyphenyl)-6,7-dihydro-1H-pyrazolo[4,3-e][1,4]diazepin-8-one
(R1=methyl; R2=ethyl; R3=3,4,5-trimethoxyphenyl)
Step 7:

According to M10, 0.153 g (0.77 mmol) of 2-ethyl-5-methyl-4-nitro-2H-pyrazole-3-carboxylic acid (A) is reacted with 0.246 g (0.77 mmol) of 2-amino-1-(3,4,5-trimethoxyphenyl)-ethanone hydrochloride (78%) (*J. Org. Chem.*, 38, 3571–3575, 1973) to give 0.313 g (83%) of an amide of type C (see scheme 1).

Rf (CH$_2$Cl$_2$/MeOH 95/5)=0.78
$^1$H NMR (CDCl$_3$, 400 MHz), 8.0 ppm (1H, bs); 7.2 ppm (2H, d); 5.0 ppm (2H, d); 4.3 ppm (2H, q); 3.9 ppm (9H, s); 2.6 ppm (3H, s); 1.5 ppm (3H, t)
Step 8:

According to M12, 0.26 g (0.64 mmol) of the amide C (see scheme 1) is refluxed in ethanol with 0.72 g of tin chloride dihydrate to give 0.13 g (57%) of the expected product D (see scheme 1).

Rf (95/5 CH$_2$Cl$_2$/MeOH)=0.52
m.p.=208° C.
MS (ES+), m/z=359
$^1$H NMR (DMSO, 400 MHz), 8.25 ppm (1H, t); 7.3 ppm (2H, s); 4.45 ppm (2H, q); 4.0 ppm (2H, d); 3.9 ppm (6H, s); 3.7 ppm (3H, s); 2.3 ppm (3H, s); 1.35 ppm (3H, t)

Example 92

1-Ethyl-5-(3-hydroxyphenyl)-3-methyl-6,7-dihydro-1H-pyrazolo[4,3-e][1,4]diazepin-8-one
(R1=methyl; R2=ethyl; R3=3-hydroxyphenyl)

0.4 g (1.34 mmol) of 1-ethyl-5-(3-methoxyphenyl)-3-methyl-6,7-dihydro-1H-pyrazolo[4,3-e][1,4]diazepin-8-one is refluxed in dichloromethane with 33.5 ml of a molar solution of BBr$_3$ in dichloromethane to give 0.075 g (20%) of the expected product.

MS (ES+) m/z=285
m.p.=204° C.
Rf (90/10 CH$_2$Cl$_2$/MeOH)=0.55
$^1$H NMR (DMSO, 400 MHz), 9.65 ppm (1H, s); 8.25 ppm (1H, m); 7.45 ppm (2H, m); 7.3 ppm (1H, m); 6.9 ppm (1H, m); 4.4 ppm (2H, q); 3.95 ppm (2H, d); 2.3 ppm (3H, s); 1.35 ppm (3H, t)

Example 93

1-Ethyl-5-(2-hydroxyphenyl)-3-methyl-6,7-dihydro-1H-pyrazolo[4,3-e][1,4]diazepin-8-one
(R1=methyl; R2=ethyl; R3=2-hydroxyphenyl)

0.4 g (1.34 mmol) of 1-ethyl-5-(2-methoxyphenyl)-3-methyl-6,7-dihydro-1H-pyrazolo[4,3-e][1,4]diazepin-8-one is refluxed in dichloromethane with 33.5 ml of a molar solution of BBr$_3$ in dichloromethane to give 0.070 g (19%) of the expected product.

MS (ES+) m/z=285
m.p.=220° C.
Rf (90/10 CH$_2$Cl$_2$/MeOH)=0.7
$^1$H NMR (DMSO, 400 MHz), 14.0 ppm (1H, s); 8.35 ppm (1H, m); 7.8 ppm (1H, m); 7.4 ppm (1H, m); 7.0 ppm (2H, m); 4.45 ppm (2H, q); 4.2 ppm (2H, d); 2.3 ppm (3H, s); 1.35 ppm (3H, t)

Example 94

1-Ethyl-5-(4-hydroxyphenyl)-3-isopropyl-6,7-dihydro-1H-pyrazolo[4,3-e][1,4]diazepin-8-one
(R1=isopropyl; R2=ethyl; R3=4-hydroxyphenyl)

0.5 g (1.53 mmol) of 1-ethyl-5-(4-methoxy-phenyl)-3-isopropyl-6,7-dihydro-1H-pyrazolo[4,3-e][1,4]diazepin-8-one is refluxed in dichloromethane with 38 ml of a molar solution of BBr$_3$ in dichloromethane to give 0.23 g (48%) of the expected product.

MS (ES+) m/z=313
m.p.=230° C.

Rf (90/10 CH$_2$Cl$_2$/MeOH)=0.27

$^1$H NMR (DMSO, 400 MHz), 10.0 ppm (1H, s); 8.2 ppm (1H, t); 7.85 ppm (2H, d); 6.85 ppm (2H, d); 4.4 ppm (2H, q); 3.9 ppm (2H, d); 3.2 ppm (1H, m); 1.35 ppm (3H, t); 1.3 ppm (6H, d)

Example 95

5-(4-Hydroxyphenyl)-3-isopropyl-1-propyl-6,7-dihydro-1H-pyrazolo[4,3-e][1,4]diazepin-8-one (R1=isopropyl; R2=propyl; R3=4-hydroxyphenyl)

0.5 g (1.47 mmol) of 5-(4-methoxyphenyl)-3-isopropyl-1-propyl-5-6,7-dihydro-1H-pyrazolo[4,3-e][1,4]diazepin-8-one is refluxed in dichloromethane with 37 ml of a molar solution of BBr$_3$ in dichloromethane to give 0.2 g (42%) of the expected product.

MS (ES+) m/z=327 m.p.=230° C.

Rf (90/10 CH$_2$Cl$_2$/MeOH)=0.38

$^1$H NMR (DMSO, 400 MHz), 10.0 ppm (1H, s); 8.2 ppm (1H, t); 7.85 ppm (2H, d); 6.85 ppm (2H, d); 4.4 ppm (2H, q); 3.9 ppm (2H, d); 3.2 ppm (1H, m); 1.8 ppm (2H, m); 1.3 ppm (6H, d); 0.85 ppm (3H, t)

Example 96

3-tert-Butyl-1-ethyl-5-(4-hydroxyphenyl)-6,7-dihydro-1H-pyrazolo[4,3-e][1,4]diazepin-8-one (R1=tert-butyl; R2=ethyl; R3=4-hydroxyphenyl)

0.5 g (1.47 mmol) of 1-tert-butyl-5-(4-methoxyphenyl)-3-isopropyl-6,7-dihydro-1H-pyrazolo[4,3-e][1,4]diazepin-8-one is refluxed in dichloromethane with 1.4 ml of BBr$_3$ to give 0.29 g (60%) of the expected product.

MS (ES+) m/z=327 m.p.=264° C.

Rf (90/10 CH$_2$Cl$_2$/MeOH)=0.4

$^1$H NMR (DMSO, 400 MHz), 10.0 ppm (1H, s); 8.2 ppm (1H, t); 7.85 ppm (2H, d); 6.85 ppm (2H, d); 4.4 ppm (2H, q); 3.9 ppm (2H, d); 1.4 ppm (9H, s); 1.3 ppm (3H, t)

Example 97

3-Ethoxymethyl-1-ethyl-5-phenyl-6,7-dihydro-1H-pyrazolo-[4,3-e][1,4]diazepin-8-one (R1=ethoxymethyl ; R2=ethyl; R3=phenyl)

Step 19:

8.1 g (22 mmol) of compound R (see scheme 3) are reacted with 49 ml of ethylene glycol and 0.81 g (4.3 mmol) of para-toluenesulphonic acid monohydrate in 170 ml of toluene. After 48 hours, about 40 ml of water have been removed (Dean-Stark apparatus). The reaction mixture is treated with saturated NaHCO$_3$ solution and water and the phases are then allowed to separate by settling. The organic phase is dried over Na$_2$SO$_4$ and concentrated. The oil obtained is chromatographed on silica with an 80/20 cyclohexane/EtOAc mixture to give 6.6 g (73%) of the expected compound S (see scheme 3).

Rf (70/30 cyclohexane/EtOAc)=0.28

MS (ES+), m/z=418.9

$^1$H NMR (CDCl$_3$, 400 MHz), 7.3–7.55 ppm (6H, m); 4.4–4.5 ppm (4H, m); 4.1 ppm (2H, q); 3.8 ppm (4H, m); 1.5 ppm (3H, t); 1.4 ppm (3H, t)

Step 20:

1.5 g (3.6 mmol) of compound S (see scheme 3) are reacted with 4.3 ml (8.6 mmol) of a 2M solution of lithium borohydride in THF, in 25 ml of anhydrous THF. After 12 hours at room temperature, the reaction mixture is extracted with water and diethyl ether. The organic phase is dried over Na$_2$SO$_4$ and concentrated to give 1.2 g (96%) of the expected compound T (see scheme 3).

Rf (95/5 CH$_2$Cl$_2$/MeOH)=0.17

MS (ES+), m/z=347

$^1$H NMR (DMSO, 400 MHz), 8.65 ppm (1H, m); 7.3–7.5 ppm (5H, m); 4.9 ppm (1H, t); 4.4 ppm (2H, d); 4.3 ppm (2H, q); 4.05 ppm (2H, t); 4.0 ppm (2H, s); 3.8 ppm (2H, t); 3.7 ppm (2H, d); 1.2 ppm (3H, t)

Step 21:

0.3 g (0.9 mmol) of compound T (see scheme 3) is reacted with 15 ml of ethanol and 15 ml of 6N HCl at 80° C. After 12 hours, the reaction mixture is concentrated and the residue obtained is extracted with water and dichloromethane. The organic phase is dried over Na$_2$SO$_4$ and concentrated and then chromatographed on silica using an elution gradient of from 100% dichloromethane to a 95/5 dichloromethane/MeOH mixture to give 0.023 g (8.5%) of the compound D (see scheme 3) (RB=ethyl).

Rf (95/5 CH$_2$Cl$_2$/MeOH)=0.27

MS (ES+), m/z=313

$^1$H NMR (CDCl$_3$, 400 MHz), 7.9 ppm (2H, m); 7.45 ppm (3H, m); 6.0 ppm (1H, m); 4.75 ppm (2H, s); 4.6 ppm (2H, q); 4.15 ppm (2H, d); 3.65 ppm (2H, q); 1.5 ppm (3H, t); 1.25 ppm (3H, t)

Evaluation of the Biological Activity of the Compounds of the Present Invention

Evaluation of the in vitro Activity of the Compounds of the Examples

The capacity of the compounds of formula (I) of the invention to inhibit cyclic nucleotide phosphodiesterases is evaluated by measuring their IC$_{50}$ (concentration needed to inhibit 50% of the enzymatic activity). In the case of PDE4 enzymes, this value is compared to the IC$_{50}$ value for rolipram, a reference inhibitor for PDE4 enzymes.

The type 4 phosphodiesterases are obtained from a cytosolic preparation extracted from a cell line of human origin, U937, according to the method adapted from T. J. Torphy et al., 1992, J. Pharm. Exp. Ther. 263: 1195–1205.

The other types of phosphodiesterase are obtained during a partial purification by FPLC on a Mono Q column (anion exchange column) according to a method adapted from Lavan B. E., Lakey T., Houslay M. D. Biochemical Pharmacology, 1989, 38(22), 4123–4136, and Silver P. J et al., 1988, Eur. J. Pharmacol. 150: 85–94, either starting with cell lines of human origin for PDE1 (monocyte line TPH1) and PDE5 (line derived from an adenocarcinoma MCF7), or starting with dog aorta for PDE3, or, for human PDE3A, starting with a cloning of genes in SF21 insect cells into baculovirus, according to the method adapted from Luckow, V. A. et al., 1991 in Recombinant DNA Technology & Applications., eds. Prokop, Bajpai, R. K. & Ho, C. S., pp 97–152.

The measurement of the enzymatic activity for the various types of PDE, and in particular the PDE4 enzymes, is carried out according to a method adapted from W. J. Thomson et al. 1979, Advances in Cyclic Nucleotide Research, Vol. 10: 69–92, ed. G. Brooker et al. Raven Press, NY.

For the determination of the IC$_{50}$ value, the enzymatic activity is measured in the presence of the inhibitor in a concentration range from 0.1 to 100 μM.

Table 1 below illustrates the inhibitory activity of PDE4 compared with that of rolipram on an enzyme preparation obtained from the U937 line.

TABLE 1

| Example | IC$_{50}$ ($\mu$M) |
|---|---|
| 1 | 0.0049 |
| 2 | 0.00098 |
| 3 | 0.00012 |
| 4 | 0.0084 |
| 5 | 0.39 |
| 6 | 0.42 |
| 7 | 0.13 |
| 8 | 0.21 |
| 9 | 0.15 |
| 10 | 1.29 |
| 11 | 0.12 |
| 12 | 0.10 |
| 13 | 0.13 |
| 14 | 0.081 |
| 15 | 0.52 |
| 16 | 0.42 |
| 17 | 0.0059 |
| 18 | 0.10 |
| 19 | 0.087 |
| 20 | 0.099 |
| 21 | 0.0026 |
| 22 | 0.028 |
| 23 | 0.042 |
| 24 | 0.078 |
| 25 | 0.0024 |
| 26 | 0.0056 |
| 27 | 0.0038 |
| 28 | 0.090 |
| 29 | 0.33 |
| 30 | 0.30 |
| 31 | 0.19 |
| 32 | 0.13 |
| 33 | 0.11 |
| 34 | 0.0047 |
| 35 | 0.00070 |
| 36 | 0.00039 |
| 37 | 0.00097 |
| 38 | 0.65 |
| 39 | 0.0091 |
| 40 | 0.0082 |
| 41 | 0.011 |
| 42 | 0.010 |
| 43 | 0.048 |
| 44 | 0.0011 |
| 45 | 0.0026 |
| 46 | 0.00084 |
| 47 | 0.021 |
| 48 | 0.0081 |
| 49 | 0.032 |
| 50 | 0.016 |
| 51 | 0.06 |
| 52 | 0.00065 |
| 53 | 0.26 |
| 54 | 0.24 |
| 55 | 0.0017 |
| 56 | 0.50 |
| 57 | 0.00013 |
| 58 | 0.14 |
| 59 | 0.51 |
| 60 | 0.58 |
| 61 | 0.0079 |
| 62 | 0.26 |
| 63 | 0.0050 |
| 64 | 0.0046 |
| 65 | 0.0015 |
| 66 | 0.00063 |
| 67 | 0.0010 |
| 68 | 0.0062 |
| 69 | 0.013 |
| 70 | 0.011 |
| 71 | 0.035 |
| 72 | 0.0018 |
| 73 | 0.00073 |
| 74 | 0.0054 |
| 75 | 0.0049 |
| 76 | 0.0082 |
| 77 | 0.21 |
| 78 | 0.021 |
| 79 | 0.011 |
| 80 | 0.00022 |
| 81 | 0.00054 |
| 82 | 0.062 |
| 83 | 0.10 |
| 84 | 0.060 |
| 85 | 0.20 |
| 86 | 0.31 |
| 87 | 0.041 |
| 88 | 0.0021 |
| 89 | 0.033 |
| 90 | 0.193 |
| 91 | 0.90 |
| 92 | 0.092 |
| 93 | 0.0074 |
| 94 | 0.0021 |
| 95 | 0.015 |
| 96 | 0.0049 |
| 97 | 1.58 |
| Rolipram | 0.859 |

Examination of the results of Table 1 shows that the products of the invention tested in the study generally inhibit the PDE4 enzyme of human origin much more effectively than rolipram, and in certain cases these products are between 3 000 and 4 000 times more active than rolipram.

Evaluation of the in vivo Activity of the Compounds of the Invention in vivo TNFα Model in Wistar Rats TNFα is a cytokine which plays a central role in the mechanisms of inflammation. Its production can be induced by an injection of lipopolysaccharide (LPS). It has been shown that the increase in intracellular cAMP, produced in particular by PDE4 inhibitors, decreases the production of TNFα in in vitro and in vivo models. It is thus a matter here of quantifying in vivo the anti-inflammatory potential of the compounds of the invention, administered orally (p.o.) by measuring the inhibition of the production of TNFα in the plasma of rats, these rats having received an intraperitoneal (i.p.) injection of lipopolysaccharide (LPS). The treatment with the compounds of the invention or the vehicle are [sic] administered orally to male Wistar rats, 30 min before the injection of LPS. The rats are sacrificed 90 min after the stimulation with LPS, the blood is collected onto EDTA and the TNFα concentration is measured in each plasma sample. Most of the compounds of the invention and in particular the compounds hereinbelow showed excellent activity in this model.

1-Ethyl-5-(4-methoxyphenyl)-3-methyl-6,7-dihydro-1H-pyrazolo[4,3-e][1,4]diazepin-8-one, 5-(4-Aminophenyl)-1-ethyl-3-methyl-6,7-dihydro-1H-pyrazolo[4,3-e][1,4]diazepin-8-one, 3-Methyl-5-phenyl-1-propyl-6,7-dihydro-1H-pyrazolo[4,3-e][1,4]diazepin-8-one, 1-(2-Hydroxyethyl)-3-methyl-5-phenyl-6,7-dihydro-1H-pyrazolo[4,3-e][1,4]diazepin-8-one, 1-Ethyl-3-methyl-5-phenyl-6,7-dihydro-1H-pyrazolo-[4,3-e][1,4]diazepin-8-thione, 1-Ethyl-3-isopropyl-5-phenyl-6,7-dihydro-1H-pyrazolo-[4,3-e][1,4]diazepin-8-one, 3-tert-Butyl-1-ethyl-5-phenyl-6,7-dihydro-1H-pyrazolo-[4,3-e][1,4]diazepin-8-one, 1-Ethyl-3-methyl-5-p-tolyl-6,7-dihydro-1H-pyrazolo-[4,3-e][1,4]diazepin-8-one, 5-(3-Aminophenyl)-1-ethyl-3-methyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-thione,
1-Ethyl-3-isopropyl-5-phenyl-6,7-dihydro-1H-pyrazolo-[4,3-e][1,4]diazepin-8-thione,
5-(4-Aminophenyl)-3-tert-butyl-1-ethyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-one,
5-Cyclohexyl-1-ethyl-3-methyl-6,7-dihydro-1H-pyrazolo-[4,3-e][1,4]diazepin-8-one,
1-Ethyl-3-methyl-5-pyrid-4-yl-6,7-dihydro-1H-pyrazolo-[4,3-e][1,4]diazepin-8-one,
5-tert-Butyl-1-ethyl-3-methyl-4,5,6,7-tetrahydro-1H-pyrazolo[4,3-e][1,4]diazepin-8-one,
3-Butyl-1-ethyl-5-phenyl-6,7-dihydro-1H-pyrazolo-[4,3-e][1,4]diazepin-8-one,
5-tert-Butyl-1-ethyl-3-isopropyl-6,7-dihydro-1H-pyrazolo[4,3-e][1,4]diazepin-8-one,
1-Ethyl-3-isopropyl-5-p-tolyl-6,7-dihydro-1H-pyrazolo-[4,3-e][1,4]diazepin-8-one,
4-(1-Ethyl-3-isopropyl-8-oxo-1,6,7,8-tetrahydro-pyrazolo[4,3-e][1,4]diazepin-5-yl)benzonitrile,
5-(2,4-Dimethoxyphenyl)-1-ethyl-3-isopropyl-6,7-dihydro-1H-pyrazolo[4,3-e][1,4]diazepin-8-one,
5-tert-Butyl-3-isopropyl-1-propyl-6,7-dihydro-1H-pyrazolo-[4,3-e][1,4]diazepin-8-one,
3-Isopropyl-1-propyl-5-p-tolyl-6,7-dihydro-1H-pyrazolo[4,3-e][1,4]diazepin-8-one,
4-(3-Isopropyl-8-oxo-1-propyl-1,6,7,8-tetrahydro-pyrazolo-[4,3-e][1,4]diazepin-5-yl)benzonitrile,
3-tert-Butyl-1-ethyl-5-p-tolyl-6,7-dihydro-1H-pyrazolo[4,3-e][1,4]diazepin-8-one,
4-(3-tert-Butyl-1-ethyl-8-oxo-1,6,7,8-tetrahydropyrazolo-[4,3-e][1,4]diazepin-5-yl)benzonitrile,
1-Ethyl-3-methyl-5-phenyl-1,6-dihydropyrazolo-[4,3-e][1,4]diazepin-8-ylcyanamide,
1-Ethyl-3-isopropyl-5-phenyl-6,7-dihydro-1H-pyrazolo-[4,3-e][1,4]diazepin-8-ylidenecyanamide,
(±)3-sec-Butyl-1-ethyl-5-phenyl-6,7-dihydro-1H-pyrazolo-[4,3-e][1,4]diazepin-8-one,
(±)3-sec-Butyl-1-ethyl-5-pyrid-4-yl-6,7-dihydro-1H-pyrazolo[4,3-e][1,4]diazepin-8-one,
(±)3-sec-Butyl-1-propyl-5-pyrid-4-yl-6,7-dihydro-1H-pyrazolo[4,3-e][1,4]diazepin-8-one,
3-Cyclohexyl-1-ethyl-5-pyrid-4-yl-6,7-dihydro-1H-pyrazolo-[4,3-e][1,4]diazepin-8-one,
3-Cyclohexyl-1-propyl-5-pyrid-4-yl-6,7-dihydro-1H-pyrazolo-[4,3-e][1,4]diazepin-8-one.

References

Chen, Y. L., Le Vraux, V., Giroud, J. P. and Chauvelot-Moachon L. (1994). Anti-tumor necrosis factor properties of non-peptide drugs in acute-phase responses. Eur. J. Pharmacol., 271 (2–3), 319–27.

Prabhakar, U., Lipshutz, D., O'Leary Barthus, J., Slivjak, J., Smith III E. F., Lee, J. C. and Esser K. M. (1994). Characterization of cAMP-dependent inhibition of LPS-induced TNFα production by rolipram, a specific phosphodiesterase IV (PDE IV) inhibitor. Int. J. Immunopharmacol., 16 (10), 805–816.

Model of Eosinophilia in Rats

The studies carried out using this experimental model have the aim of evaluating the inhibitory activity of the compounds of the invention on the afflux of inflammatory cells and in particular of eosinophils in the lumen of the bronchotracheal tree of rats. Eosinophils play a major role in the physiopathology of asthma in man by releasing into the pulmonary parenchyma pro-inflammatory mediators such as leukotrienes, specific proteins and enzymes (ECP, EPO, MBP) and cytokines. The massive recruitment of this cell type in the aerial pathways of an asthmatic leads to a gradual degradation of the pulmonary tissue, which explains the bronchial hyperreactivity, the chronic aspect of the disease and the exacerbations in the absence of treatment. This model uses Brown Norway rats, which have the particular feature of producing, like atopic patients, high levels of immunoglobulin E (IgE) in response to a sensitization by an antigen. The protocol used involves two sensitizations with ovalbumin with a fourteen-day interval, followed by a challenge seven days later with an ovalbumin aerosol. 48 hours after the antigenic challenge, the animals undergo bronchoalveolar lavage under anaesthesia in order to collect the infiltrate of inflammatory cells on the lungs. These cells are then counted and differentiated according to morphological criteria. The products of the invention are administered orally, 1 hour before the antigenic challenge. Most of the compounds of the present invention tested in this model also demonstrated excellent activity.

References

Corrigan et al. (1992) Immunology today 13: 501–507
Elwood et al. (1995) Inflamm Res 44: 83–86

Model of Neutrophilia in Mice

The studies carried out using this experimental protocol have the aim of evaluating the modulatory action of the compounds of the invention on the afflux of pro-inflammatory cells (early phase) in the lumen of the bronchotracheal tree of mice. This cellular afflux follows a stimulation mimicking a bacterial infection (bacterial lipopoly-saccharide or LPS). This early inflammatory stage is the result of a combination of events, the main ones of which are the synthesis and release of stimulatory factors (TNFα[i]) and chemotactic factors (IL-8[ii]), the increase in vascular permeability in the bronchotracheal microcirculation, and the infiltration of polymorphonuclear neutrophils, concomitant with the exudation of plasma proteins into the pulmonary tissues.

This pathological process is found in chronic obstructive bronchopneumopathy (or COPD), in which the neutrophil, in concert with the macrophage, plays a key role in establishing the amplification of the recruitment of the neutrophils themselves, but also in the destructuring of pulmonary tissues (decline in pulmonary functions), the hypersecretion of bronchotracheal mucus (congestion of the aerial pathways), tissue inflammation (release of inflammatory mediators and free radicals) and increase in the basal tonus of pulmonary smooth muscle fibres (chronic respiratory gene). Most of the compounds of the present invention tested in this model demonstrated excellent activity.

References

[i]SUTER P. M., SUTER S., GIRARDIN E., ROUX-LOMBARD P., GRAU G. E. and DAYER J. -M. 1992. High bronchoalveolar levels of tumor necrosis factor and its inhibitors, interleukin-1, interferon and elastase, in patients with adult respiratory distress syndrome after trauma, shock or sepsis. Am. Rev. Respir. Dis. 145: 1016–1022.

[ii]MARTIN T. R. and GOODMAN R. B. 1999. The role of chemokines in the pathology of the acute respiratory distress syndrome. Chapter 6 in Chemokines in disease: Biology and clinical research edited by: C. A. Hebert, Humana Press Inc., Totowa, N.J.

[iii]REPINE J. E. and BEEHLER C. J. 1991. Neutrophils and the adult respiratory distress syndrome: two interlocking perspectives. Am. Rev. Respir. Dis. 144: 251–252.

Jejunal Inflammation and Septic Shock Induced by *E. coli* Lipopolysaccharide in Rats Lipopolysaccharide (LPS) from *Escherichia coli* administered intravenously to fasted male Wistar rats induces an inflammation of the jejunum two hours later.

Male Wistar rats (200–280 g), fasted (18 h), from the Sté Janvier, Le-genest-St Isle, Mayenne, France are used in these experiments.

The compounds to be tested are suspended in a vehicle (1% methylcellulose (95% v/v)+polyethylene glycol 400 (5% v/v)). They are then administered orally (5 ml/kg) using a stainless steel probe, one hour before administration of the inducing agent (LPS). The groups of animals are distributed in the following manner:

Negative controls: p.o. vehicle+serum i.v. physiological saline

Positive controls: p.o. vehicle+LPS

Treated: p.o. compound+LPS

The lipopolysaccharide (LPS), endotoxin from *Escherichia coli* (serotype 0127:B8), is then injected intravenously (caudal vein) at a dose of 40 mg/kg (5 ml/kg) to conscious rats maintained under slight support.

Two hours later, the animals are sacrificed, the abdomen is opened and a 10 cm section of jejunum (30th to 40th after the pylorus) is taken, cut in the direction of its length, mopped and weighed.

The macroscopic attack is evaluated (0=none, 1=slight, 2=moderate, 3=severe).

After weighing, the segment is fixed onto a flat surface and measurements of the percentage of hyperhemiated surfaces are made using an image analyser.

Immediately after analysis, the tissue is deposited in 10 ml of Drabkin reagent to determine the haemoglobin content of the tissue (calorimetric assay 24 hours later). Most of the compounds of the present invention tested in this model demonstrated excellent activity.

Lipopolysaccharide (LPS): Sigma, reference L-3880, France.

Polyethylene glycol: M.W. 400, Sigma, reference P-3265

Haemoglobin content of the jejunum: Sigma kit, Total haemoglobin, reference 525-A.

Main Reference:

Cardelus Ignasi et al. European Journal of Pharmacology 299 (1996); 153–159

What is claimed is:

1. A method of treating chronic obstructive bronchopneumopathy or asthma in a mammal, which method comprises administering to said mammal a compound of formula:

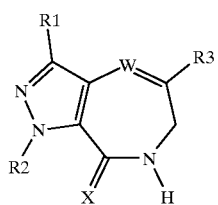

I in which:
R1 is:
  hydrogen;
  linear or branched ($C_1$–$C_6$)alkyl;
  ($C_3$–$C_6$)cycloalkyl;
  ($C_1$–$C_6$)alkyl($C_3$–$C_6$)cycloalkyl;
  ($C_5$–$C_{10}$)aryl optionally interrupted with one nitrogen, oxygen or sulphur;
  ($C_6$–$C_{10}$)arylalkyl optionally interrupted with one nitrogen, oxygen or sulphur;
  ($C_6$–$C_{10}$)alkylaryl optionally interrupted with one nitrogen, oxygen or sulphur;
  linear or branched ($C_2$–$C_6$)alkenyl; or
  $(CH_2)_nOR_B$, $(CH_2)_nCF_3$, $(CH_2)_nC(O)R_B$, $(CH_2)_nCOOR_B$, $(CH_2)_nOC(O)R_A$, $(CH_2)_nSR_B$, $(CH_2)_nC(S)R_B$, $(CH_2)_nC(S)OR_B$, $(CH_2)_nC(S)SR_B$, $(CH_2)_nNR_BR_C$, $(CH_2)_nC(O)NR_BR_C$, $(CH_2)_nNR_CC(O)R_B$, $(CH_2)_nNR_DC(O)NR_DR_B$ or $(CH_2)_nZ$;
  $R_A$ is linear or branched ($C_1$–$C_6$)alkyl;
  ($C_3$–$C_6$)cycloalkyl;
  ($C_1$–$C_6$)alkyl($C_3$–$C_6$)cycloalkyl;
  ($C_5$–$C_{10}$)aryl optionally interrupted with one nitrogen, oxygen or sulphur;
  ($C_6$–$C_{10}$)arylalkyl optionally interrupted with one nitrogen, oxygen or sulphur;
  ($C_6$–$C_{10}$)alkylaryl optionally interrupted with one nitrogen, oxygen or sulphur; or
  linear or branched ($C_2$–$C_6$)alkenyl;
  $R_B$ and $R_C$, which are identical or different, are:
  hydrogen;
  linear or branched ($C_1$–$C_6$)alkyl;
  ($C_3$–$C_6$)cycloalkyl;
  ($C_1$–$C_6$)alkyl($C_3$–$C_6$)cycloalkyl;
  ($C_5$–$C_{10}$)aryl optionally interrupted with one nitrogen, oxygen or sulphur;
  ($C_6$–$C_{10}$)arylalkyl optionally interrupted with one nitrogen, oxygen or sulphur;
  ($C_6$–$C_{10}$)alkylaryl optionally interrupted with one nitrogen, oxygen or sulphur; or
  linear or branched ($C_2$–$C_6$)alkenyl;
    it being possible for $R_B$ and $R_C$ to form ring containing from 5 to 7 atoms which can include one to three sulphur, nitrogen or oxygen;
    $R_D$ is hydrogen or linear or branched ($C_1$–$C_6$) alkyl;
    Z is a halogen; and
    n is 0, 1, 2, 3 or 4;
R2 is:
  linear or branched ($C_1$–$C_6$)alkyl;
  ($C_1$–$C_6$)alkyl($C_3$–$C_6$)cycloalkyl;
  ($C_3$–$C_6$)cycloalkyl;
  ($C_5$–$C_{10}$)aryl optionally interrupted with one nitrogen, oxygen or sulphur;
  ($C_6$–$C_{10}$)alkylaryl optionally interrupted with one nitrogen oxygen or sulphur;
  linear or branched ($C_2$–$C_6$)alkenyl; or
  $(CH_2)_mOR_B$, $(CH_2)_nCF_3$, $(CH_2)_mC(O)R_B$, $(CH_2)_mCOOR_B$,
  $(CH_2)_mOC(O)R_A$,
  $(CH_2)_mSR_B$, $(CH_2)_mC(S)R_B$, $(CH_2)_mC(S)OR_B$, $(CH_2)_mC(S)SR_B$,
  $(CH_2)_mNR_BR_C$, $(CH_2)_mC(O)NR_BR_C$, $(CH_2)_mNR_CC(O)R_B$,
  $(CH_2)_mNR_DC(O)NR_DR_B$ or $(CH_2)_mZ$;
  m is 0, 1, 2, 3 or 4;
R3 is:
  hydrogen;
  linear or branched ($C_1$–$C_6$)alkyl;
  ($C_3$–$C_6$)cycloalkyl;
  ($C_1$–$C_6$)alkyl($C_3$–$C_6$)cycloalkyl;
  ($C_5$–$C_{10}$)aryl optionally interrupted with one nitrogen, oxygen or sulphur;
  ($C_6$–$C_{10}$)arylalkyl optionally interrupted with one nitrogen, oxygen or sulphur;

($C_6$–$C_{10}$)alkylaryl optionally interrupted with one nitrogen, oxygen or sulphur;

linear or branched ($C_2$–$C_6$)alkenyl; or $(CH_2)_nOR_B$, $(CH_2)_nCF_3$, $(CH_2)_nC(O)R_B$, $(CH_2)_n COOR_B$, $(CH_2)_nOC(O)R_A$, $(CH_2)_nSR_B$, $(CH_2)_nC(S)R_B$, $(CH_2)_nC(S)OR_B$, $(CH_2)_nC(S)SR_B$, $(CH_2)_nNR_BR_C$, $(CH_2)_nC(O)NR_BR_C$, $(CH_2)_nNR_CC(O)R_B$, $(CH_2)_nNR_DC(O)NR_DR_B$ or $(CH_2)_nZ$;

the aryl, arylalkyl and alkylaryl are unsubstituted or substituted on the aryl with 1, 2 or 3:

halogen, hydroxyl, NO, $NO_2$, CN, ($C_1$–$C_4$) alkoxy, $(CH_2)_nOR_B$, $(CH_2)_nNR_BR_C$, $(CH_2)_n NC(O)R_B$, $(CH_2)_nHNSO_2R_B$, $(CH_2)_nN(SO_2R_B)_2$, $CO_2R_B$, $CF_3$ or

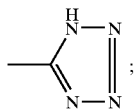

and the dotted line is absent such that the bond between W and the carbon atom at position 5 is a single bond and W is —NH—, or the dotted line is present such that the bond between W and the carbon atom at position 5 is a double bond and W is —N—;

X is S, O, N—CN or N—$R_B$;

or an oxide, tautomer or optical isomer thereof;

with the proviso that when

R1 is methyl, R2 is ethyl, W is —N—, X is an oxygen atom and the dotted line is present, then R3 is neither an unsubstituted phenyl group nor a phenyl group bearing a fluorine atom in an ortho position as sole substituent, a pharmceutically acceptable salt thereof, or a pharmaceutical composition comprising said compound or said pharmaceutically acceptable salt thereof.

2. A method of claim 1 comprising a compound of formula I;

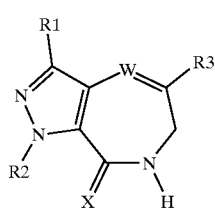

in which R1, R2, R3 and X are as defined in claim 1, W is —N— and the dotted line is present.

3. A method of claim 1 comprising a compound of formula II;

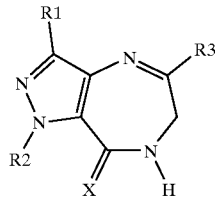

in which;

R1 is linear or branched ($C_1$–$C_6$)alkyl;

($C_3$–$C_6$)cycloalkyl;

($C_1$–$C_6$)alkyl($C_3$–$C_6$)cycloalkyl;

($C_5$–$C_{10}$)aryl optionally interrupted with with one nitrogen, oxygen or sulphur;

($C_6$–$C_{10}$)arylalkyl optionally interrupted with one nitrogen, oxygen or sulphur;

($C_6$–$C_{10}$)alkylaryl optionally interrupted with one nitrogen, oxygen or sulphur;

linear or branched ($C_2$–$C_6$)alkenyl;

$(CH_2)_nOR_B$, $(CH_2)_nCF_3$, $(CH_2)_nC(O)R_B$, $(CH_2)_nCOOR_B$, $(CH_2)_nOC(O)R_A$, $(CH_2)_nSR_B$, $(CH_2)_nNR_BR_C$, $(CH_2)_nC(O)NR_BR_C$, $(CH_2)_n NR_CC(O)R_B$ or $(CH_2)_nZ$;

$R_A$ is linear or branched ($C_1$–$C_6$)alkyl;

($C_3$–$C_6$)cycloalkyl;

($C_1$–$C_6$)alkyl($C_3$–$C_6$)cycloalkyl;

($C_5$–$C_{10}$)aryl optionally interrupted with one from nitrogen, oxygen or sulphur;

($C_6$–$C_{10}$)arylalkyl optionally interrupted with one nitrogen, oxygen or sulphur;

($C_6$–$C_{10}$)alkylaryl optionally interrupted with one nitrogen, oxygen or sulphur;

linear or branched ($C_2$–$C_6$)alkenyl;

R2 is linear or branched ($C_1$–$C_4$)alkyl;

$(CH_2)_nCF_3$;

methylcyclopropyl;

linear or branched ($C_2$–$C_6$)alkenyl;

or $(CH_2)_mOR_B$ and $(CH_2)_mCO_2R_B$; m is 1, 2 or 3;

R3 is linear or branched ($C_1$–$C_6$)alkyl;

($C_3$–$C_6$)cycloalkyl;

($C_1$–$C_6$)alkyl($C_3$–$C_6$)cycloalkyl ($C_5$–$C_{10}$)aryl optionally interrupted with one nitrogen, oxygen or sulphur;

($C_6$–$C_{10}$)arylalkyl optionally interrupted with one nitrogen, oygen or sulphur;

($C_6$–$C_{10}$)alkylaryl optionally interrupted with one nitrogen, oxygen or sulphur;

linear or branched ($C_2$–$C_6$)alkenyl;

$(CH_2)_nOR_B$, $(CH_2)_nC(O)R_B$, $(CH_2)_nCOOR_B$, $(CH_2)_nOC(O)R_A$, $CH_2)_nNR_BR_C$, $(CH_2)_nC(O)NR_BR_C$ and $(CH_2)_nNR_CC(O)R_B$; and, X is O, S or NCN.

4. A method of claim 1 in which:

R1 is linear or branched ($C_1$–$C_6$)alkyl;

($C_3$–$C_6$)cycloalkyl;

($C_1$–$C_6$)alkyl($C_3$–$C_6$)cycloalkyl;

($C_5$–$C_{10}$)aryl optionally interrupted with one nitrogen, oxygen or sulphur;

($C_6$–$C_{10}$)alkylaryl optionally interrupted with one nitrogen, oxygen or sulphur;

linear or branched ($C_2$–$C_6$)alkenyl;

$(CH_2)_nOR_B$, $(CH_2)_nC(O)R_B$, $(CH_2)_nCOOR_B$, $(CH_2)_nOC(O)R_A$, $(CH_2)_nNR_BR_C$, $(CH_2)_nC(O)NR_BR_C$, $(CH_2)_nNR_CC(O)R_B$ or $(CH_2)_nZ$, in which, R$_A$ is linear or branched (C$_1$–C$_6$)alkyl;
(C$_5$–C$_{10}$)aryl optionally interrupted with one nitrogn, oxygen or sulphur; or
(C$_6$–C$_{10}$)alkylaryl optionally interrupted with one nitrogen, oxygen or sulphur;
R$_B$ and R$_C$, which may be identical or different, are: hydrogen;
linear or branched (C$_1$–C$_6$)alkyl;
C$_5$–C$_{10}$)aryl optionally interrupted with one nitrogen, oxygen or sulphur;
(C$_6$–C$_{10}$)alkylaryl optionally interrupted with one nitrogen, oxygen or sulphur;
R2 is linear or branched (C$_1$–C$_4$)alkyl, (CH$_2$)$_m$OH or (CH$_2$)$_m$CO$_2$H; m is 1, 2 or 3;
R3 is linear or branched (C$_1$–C$_6$)alkyl;
(C$_3$–C$_6$)cycloalkyl;
(C$_5$–C$_{10}$)cycloalkyl optionally interrupted with one nitrogen, oxegen or sulphur;
(C$_6$–C$_{10}$)arylalkyl optionally interrupted with one nitrogen, oxygen or sulphur;
(C$_6$–C$_{10}$)alkylaryl optionally interrupted with one nitrogen, oxygen or sulphur;
the aryl, arylalkyl and alkylaryl are unsubstituted or substituted on the aryl with 1, 2 or 3 halogen, hydroxyl, NO, NO$_2$, CN, (C$_1$–C$_4$)alkoxy, (CH$_2$)$_n$OR$_B$, (CH$_2$)$_n$NR$_B$R$_C$, (CH$_2$)$_n$NC(O)R$_B$, CO$_2$R$_B$, CF$_3$, or

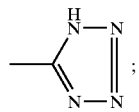

and
X is O, S or NCN.
5. A method of claim 1 in which:
R1 is linear or branched (C$_1$–C$_4$)alkyl;
(C$_3$–C$_6$)cycloalkyl;
(C$_1$–C$_3$)alkyl(C$_3$–C$_6$)cycloalkyl;
R2 is linear or branched (C$_1$–C$_4$)alkyl;
R3 is linear or branched (C$_1$–C$_4$)alkyl;
(C$_5$–C$_{10}$)aryl optionally interrupted with one nitrogen, oxygen or sulphur, the aryl groups being unsubstituted or substituted independently with 1, 2 or 3 NH$_2$, halogen, methoxy, hydroxyl, CN, CH$_3$ or CF$_3$; and,
X is O, S or NCN.
6. A meethod of claim 1 in which:
R1 is linear or branched (C$_1$–C$_4$)alkyl;
R2 is linear or branched (C$_1$–C$_4$)alkyl or (CH$_2$)$_n$OH;
R3 is linear or branched (C$_1$–C$_4$)alkyl, (C$_3$–C$_6$) cycloalkyl, phenyl or thienyl, the phenyl and thienyl may be unsubstituted or substituted independently with halogen, hydroxyl, methoxy, NH$_2$ or CH$_3$; and
X is S or O.
7. A method of claim 1 wherein said compound is 1-Ethyl-5-(4-methoxyphenyl)-3-methyl-6,7-dihydro-1H-pyrazolo[4,3-e][1,4]diazepin-8-one,
5-(4-Bromophenyl)-1-ethyl-3-methyl-6,7-dihydro-1H-pyrazolo[4,3-e][1,4]diazepin-8-one,
1,3-Dimethyl-5-phenyl-6,7-dihydro-1H-pyrazolo[4,3-e][1,4]diazepin-8-one,
5-(4-Methoxyphenyl)-1,3-dimethyl-6,7-dihydro-1H-pyrazolo[4,3-e][1,4]diazepin-8-one,
5-(4-Bromophenyl)-1,3-dimethyl-6,7-dihydro-1H-pyrazolo[4,3-e][1,4]diazepin-8-one,
1-Ethyl-3-methyl-5-naphth-2-yl-6,7-dihydro-1H-pyrazolo[4,3-e][1,4]diazepin-8-one,
5-(3-Chlorothien-2-yl)-1-ethyl-3-methyl-6,7-dihydro-1H-pyrazolo[4,3-e][1,4]diazepin-8-one,
Methyl 3-(1-ethyl-3-methyl-8-oxo-1,6,7,8-tetrahydropyrazolo[4,3-e][1,4]diazepin-5-yl) propanoate,
1-Ethyl-5-phenyl-6,7-dihydro-1H-pyrazolo[4,3-e][1,4]diazepin-8-one,
1-Ethyl-3-methyl-5-phenyl-6,7-dihydro-1H-pyrazolo[4,3-e][1,4]diazepin-8-one,
5-(4-Chlorophenyl)-1-ethyl-3-methyl-6,7-dihydro-1H-pyrazolo[4,3-e][1,4]diazepin-8-one,
5-(4-Aminophenyl)-1-ethyl-3-methyl-6,7-dihydro-1H-pyrazolo[4,3-e][1,4]diazepin-8-one,
1-Ethyl-5-(4-fluorophenyl)-3-methyl-6,7-dihydro-1H-pyrazolo[4,3-e][1,4]diazepin-8-one,
5-(3-Bromophenyl)-1-ethyl-3-methyl-6,7-dihydro-1H-pyrazolo[4,3-e][1,4]diazepin-8-one,
3-Methyl-5-phenyl-1-propyl-6,7-dihydro-1H-pyrazolo[4,3-e][1,4]diazepin-8-one,
1-Isopropyl-3-methyl-5-phenyl-6,7-dihydro-1H-pyrazolo[4,3-e][1,4]diazepin-8-one,
(±)1-Ethyl-3-methyl-5-phenyl-4,5,6,7-tetrahydro-1H-pyrazolo[4,3-e][1,4]diazepin-8-one,
1-(2-Hydroxyethyl)-3-methyl-5-phenyl-6,7-dihydro-1H-pyrazolo[4,3-e][1,4]diazepin-8-one,
1-Ethyl-3-methyl-5-phenyl-6,7-dihydro-1H-pyrazolo[4,3-e][1,4]diazepin-8-thione,
1-Ethyl-5-(4-methoxyphenyl)-6,7-dihydro-1H-pyrazolo[4,3-e][1,4]diazepin-8-one,
1-Ethyl-5-(3-methoxyphenyl)-3-methyl-6,7-dihydro-1H-pyrazolo[4,3-e][1,4]diazepin-8-one,
5-(2-Aminophenyl)-1-ethyl-3-methyl-6,7-dihydro-1H-pyrazolo[4,3-e][1,4]diazepin-8-one,
1-Ethyl-5-(2-methoxyphenyl)-3-methyl-6,7-dihydro-1H-pyrazolo[4,3-e][1,4]diazepin-8-one,
1-Ethyl-3-isopropyl-5-phenyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-one,
1-Ethyl-3-methyl-5-phenyl-4,5,6,7-tetrahydro-1H-pyrazolo[4,3-e][1,4]diazepin-8-one, isomer 1,
1-Ethyl-3-methyl-5-phenyl-4,5,6,7-tetrahydro-1H-pyrazolo[4,3-e][1,4]diazepin-8-one, isomer 2,
3-Methyl-5-phenyl-1-propyl-6,7-dihydro-1H-pyrazolo[4,3-e][1,4]diazepin-8-thione,
1-Ethyl-3-methyl-5-p-tolyl-6,7-dihydro-1H-pyrazolo[4,3-e][1,4]diazepin-8-one,
5-(3-Aminophenyl)-1-ethyl-3-methyl-6,7-dihydro-1H-pyrazolo[4,3-e][1,4]diazepin-8-one,
3-tert-Butyt-1-ethyl-5-phenyl-6,7-dihydro-1H-pyrazolo[4,3-e][1,4]diazepin-8-thione,
1-Ethyl-3-isopropyl-5-phenyl-6,7-dihydro-1H-pyrazolo[4,3-e][1,4]diazepin-8-thione,
5-(4-Aminophenyl)-3-tert-butyl-1-ethyl-6,7-dihydro-1H-pyrazolo[4,3-e][1,4]diazepin-8-one,
5-(4-Aminophenyl)-1-ethyl-3-isopropyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-one, 5-(4-Aminophenyl)-3-methyl-1-propyl-6,7-dihydro-1H-pyrazolo[4,3-e][1,4]diazepin-8-one,
3-Methyl-5-phenyl-1-(2,2,2-trifluoroethyl)-6,7-dihydro-1H-pyrazolo[4,3-e][1,4]diazepin-8-one,
1,5-Diethyl-3-methyl-6,7-dihydro-1H-pyrazolo[4,3-e][1,4]diazepin-8-one,
5-Cyclohexyl-1-ethyl-3-methyl-6,7-dihydro-1H-pyrazolo[4,3-e][1,4]diazepin-8-one,
1-Ethyl-3-methyl-5-pyrid-4-yl-6,7-dihydro-1H-pyrazolo[4,3-e][1,4]diazepin-8-one,
(±)1-Ethyl-3-methyl-5-pyrid-4-yl-4,5,6,7-tetrahydro-1H-pyrazolo[4,3-e][1,4]diazepin-8-one,
5-tert-Butyl-1-ethyl-3-methyl-4,5,6,7-tetrahydro-1H-pyrazolo[4,3-e][1,4]diazepin-8-one,
5-(4-Diethylaminophenyl)-1-ethyl-3-methyl-6,7-dihydro-1H-pyrazolo[4,3-e][1,4]diazepin-8-one,
3-Butyl-1-ethyl-5-phenyl-6,7-dihydro-1H-pyrazolo[4,3-e][1,4]diazepin-8-one,
N-[4-(1-Ethyl-3-methyl-8-oxo-1,6,7,8-tetrahydropyrazolo[4,3-e][1,4]diazepin-5-yl)phenyl]acetamide,
4-(1-Ethyl-3-methyl-8-oxo-1,6,7,8-tetrahydropyrazolo[4,3-e][1,4]diazepin-5-yl)benzonitrile,
5-tert-Butyl-1-ethyl-3-isopropyl-6,7-dihydro-1H-pyrazolo[4,3-e][1,4]diazepin-8one,
1-Ethyl-3-isopropyl-5-p-tolyl-6,7-dihydro-1H-pyrazolo[4,3-e][1,4]diazepin-8-one,
4-(1-Ethyl-3-isopropyl-8-oxo-1,6,7,8-tetrahydro-pyrazolo[4,3-e][1,4]diazepin-5-yl)benzonitrile,
1-Ethyl-3-isopropyl-5-(4-pyrrolidin-1-yl-phenyl)-6,7-dihydro-1H-pyrazolo[4,3-e][1,4]diazepin-8-one,
5-(2,4-Dimethoxyphenyl)-1-ethyl-3-isopropyl-6,7-dihydro-1H-pyrazolo[4,3-e][1,4]diazepin-8-one,
5-tert-Butyl-3-isopropyl-1-propyl-6,7-dihydro-1H-pyrazolo[4,3-e][1,4]diazepin-8-one,
3-Isopropyl-1-propyl-5-p-tolyl-6,7-dihydro-1H-pyrazolo[4,3-e][1,4]diazepin-8-one,
4-(3-Isopropyl-8-oxo-1-propyl-1,6,7,8-tetrahydropyrazolo[4,3-e][1,4]diazepin-5-yl)benzonitrile,
3-Isopropyl-1-propyl-5-(4-pyrrolidin-1-yl-phenyl)-6,7-dihydro-1H-pyrazolo[4,3-e][1,4]diazepin-8-one,
5-(2,4-Dimethoxyphenyl)-3-isopropyl-1-propyl-6,7-dihydro-1H-pyrazolo[4,3-e][1,4]diazepin-8-one,
3,5-Di-tert-butyl-1-ethyl-6,7-dihydro-1H-pyrazolo[4,3-e][1,4]diazepin-8-one,
3-tert-Butyl-1-ethyl-5-p-tolyl-6,7-dihydro-1H-pyrazolo[4,3-e][1,4]diazepin-8-one,
4-(3-tert-Butyl-1-ethyl-8-oxo-1,6,7,8-tetrahydropyrazolo[4,3-e][1,4]diazepin-5-yl)benzonitrile,
3-tert-Butyl-1-ethyl-5-(4-pyrrolidin-1-yl-phenyl)-6,7-dihydro-1H-pyrazolo[4,3-e][1,4]diazepin-8-one,
3-tert-Butyl-5-(2,4-dimethoxyphenyl)-1-ethyl-6,7-dihydro-1H-pyrazolo[4,3-e][1,4]diazepin-8-one,
3,5-Di-tert-butyl-1-propyl-6,7-dihydro-1H-pyrazolo[4,3-e][1,4]diazepin-8-one,
3-tert-Butyl-1-propyl-5-p-tolyl-6,7-dihydro-1H-pyrazolo[4,3-e][1,4]diazepin-8-one,
4-(3-tert-Butyl-8-oxo-1-propyl-1,6,7,8-tetrahydropyrazolo[4,3-e][1,4]diazepin-5-yl)benzonitrile,
3-tert-Butyl-1-propyl-5-(4-pyrrolidin-1-yl-phenyl)-6,7-dihydro-1H-pyrazol[4,3-e][1,4]diazepin-8-one,
3-tert-Butyl-5-(2,4-dimethoxyphenyl)-1-propyl-6,7-dihydro-1H-pyrazolo[4,3-e][1,4]diazepin-8-one,
3-Butyl-1-ethyl-5-phenyl-6,7-dihydro-1H-pyrazolo[4,3-e][1,4]diazepin-8-thione,
1-Ethyl-3-methyl-5-pyrid-3-yl-6,7-dihydro-1H-pyrazolo[4,3-e][1,4]diazepin-8-one,
1-Ethyl-3-methyl-5-pyrid-2-yl-6,7-dihydro-1H-pyrazolo[4,3-e][1,4]diazepin-8-one,
1-Ethyl-3-methyl-5-phenyl-1,6-dihydropyrazolo[4,3-e][1,4]diazepin-8-ylcyanamide,
N-[4-(1-Ethyl-3-methyl-8-oxo-1,6,7,8-tetrahydropyrazolo[4,3-e][1,4]diazepin-5-yl)phenyl]-(phenylsulphonyl)benzenesulphonamide,
(1-Ethyl-3-methyl-5-phenyl-1,6-dihydropyrazolo[4,3-e][1,4]diazepin-8-yl)methylamine,
1-Ethyl-3-isopropyl-5-phenyl-6,7-dihydro-1H-pyrazolo[4,3-e][1,4]diazepin-8-ylidenecyanamide,
3-tert-Butyl-1-ethyl-5-phenyl-6,7-dihydro-1H-pyrazolo[4,3-e][1,4]diazepin-8-ylidenecyanamide,
1-Cyclopentyl-3-methyl-5-phenyl-6,7-dihydro-1H-pyrazolo[4,3-e][1,4]diazepin-8-one,
1-Cyclopropylmethyl-3-methyl-5-phenyl-6,7-dihydro-1H-pyrazolo[4,3-e][1,4]diazepin-8-one,
1-Cyclobutylmethyl-3-methyl-5-phenyl-6,7-dihydro-1H-pyrazolo[4,3-e][1,4]diazepin-8-one,
1-Allyl-3-methyl-5-phenyl-6,7-dihydro-1H-pyrazolo[4,3-e][1,4]diazepin-8-one,
1-Ethyl-3-methyl-5-(4-trifluoromethylphenyl)-6,7-dihydro-1H-pyrazolo[4,3-e][1,4]diazepin-8-one,
1-Ethyl-3-isopropyl-5-(4-trifluoromethylphenyl)-6,7-dihydro-1H-pyrazolo[4,3-e][1,4]diazepin-8-one,
3-tert-Butyl-1-ethyl-5-(4-trifluoromethylphenyl)-6,7-dihydro-1H-pyrazolo[4,3-e][1,4]diazepin-8-one,
3-Isopropyl-1-propyl-5-p-tolyl-6,7-dihydro-1H-pyrazolo[4,3-e][1,4]diazepin-8-thione,
3,5-Di-tert-butyl-1-propyl-6,7-dihydro-1H-pyrazolo[4,3-e][1,4]diazepin-8-thione,
5-tert-Butyl-3-isopropyl-1-propyl-6,7-dihydro-1H-pyrazolo[4,3-e][1,4]diazepin-8-thione,
1-Ethyl-3-isopropyl-5-p-tolyl-6,7-dihydro-1H-pyrazolo[4,3-e][1,4]diazepin-8-thione,
5-tert-Butyl-1-ethyl-3-isopropyl-6,7-dihydro-1H-pyrazolo[4,3-e][1,4]diazepin-8-thione,
(±)3-sec-Butyl-1-ethyl-5-phenyl-6,7-dihydro-1H-pyrazolo[4,3-e][1,4]diazepin-8-one,
(±)3-sec-Butyl-1-ethyl-5-pyrid-4-yl-6,7-dihydro-1H-pyrazolo[4,3-e][1,4]diazepin-8-one,
(±)3-sec-Butyl-5-phenyl-1-propyl-4-yl-6,7-dihydro-1H-pyrazolo[4,3-e][1,4]diazepin-8-one,
(±)3-sec-Butyl-1-propyl-5-pyrid-4-yl-6,7-dihydro-1H-pyrazolo[4,3-e][1,4]diazepin-8-one,
3-Cyclohexyl-1-ethyl-5-phenyl-4-yl-6,7-dihydro-1H-pyrazolo[4,3-e][1,4]diazepin-8-one,
3-Cyclohexyl-1-ethyl-5-pyrid-4-yl-6,7-dihydro-1H-pyrazolo[4,3-e][1,4]diazepin-8-one,
3-Cyclohexyl-5-phenyl-1-propyl-4-yl-6,7-dihydro-1H-pyrazolo[4,3-e][1,4]diazepin-8-one,
3-Cyclohexyl-1-propyl-5-pyrid-4-yl-6,7-dihydro-1H-pyrazolo[4,3-e][1,4]diazepin-8-one,
3-Cyclohexylmethyl-1-ethyl-5-pyrid-4-yl-6,7-dihydro-1H-pyrazolo[4,3-e][1,4]diazepin-8-one,
3-Cyclohexylmethyl-5-phenyl-1-propyl-6,7-dihydro-1H-pyrazolo[4,3-e][1,4]diazepin-8-one, 3-Cyclohexytmethyl-1-propyl-5-pyrid-4-yl-6,7-dihydro-1H-pyrazolo[4,3-e][1,4]diazepin-8-one, 3-Cyclohexylmethyl-1-ethyl-5-phenyl-6,7-dihydro-1H-pyrazolo[4,3-e][1,4]diazepin-8-one, 1-Ethyl-8-oxo-5-phenyl-1,6,7,8-tetrahydropyrazolo[4,3-e][1,4]diazepin-3-carboxylic acid ethyl ester, 5-tert-Butyl-1-ethyl-3-isopropyl-6,7-dihydro-1H-pyrazolo[4,3-e][1,4]diazepin-8-ylidenecyanamide, 1-Ethyl-3-isopropyl-5-p-tolyl-6,7-dihydro-1H-pyrazolo[4,3-e][1,4]diazepin-8-ylidenecyanamide, 1-Ethyl-3-isopropyl-5-(4-methoxyphenyl)-6,7-dihydro-1H-pyrazolo[4,3-e][1,4]diazepin-8-one, 1-Ethyl-5-(4-methoxyphenyl)-3-methyl-6,7-dihydro-1H-pyrazolo[4,3-e][1,4]diazepin-8-thione, 1-Ethyl-5-(4-methoxyphenyl)-3-methyl-8,7-dihydro-1H-pyrazolo[4,3-e][1,4]diazepin-8-ylidenecyanamide, 3-Isopropyl-5-(4-methoxyphenyl)-1-propyl-6,7-dihydro-1H-pyrazolo[4,3-e][1,4]diazepin-8-one, 3-tert-Butyl-1-ethyl-5-(4-methoxyphenyl)-6,7-dihydro-1H-pyrazolo[4,3-e][1,4]diazepin-8-one, 3-tert-Butyl-5-(4-methoxyphenyl)-1-propyl-6,7-dihydro-1H-pyrazolo[4,3-][1,4]diazepin-8-one, 1-Ethyl-5-(4-hydroxyphenyl)-3-methyl-6,7-dihydro-1H-pyrazolo[4,3-e][1,4]diazepin-8-ylidenecyanamide, (±)3-sec-Butyl-1-ethyl-5-(4-methoxyphenyl)-6,7-dihydro-1H-pyrazolo[4,3-e][1,4]diazepin-8-one, (±)3-sec-Butyl-5-(4-methoxyphenyl)-1-propyl-6,7-dihydro-1H-pyrazolo[4,3-e][1,4]diazepin-8-one, 1-Ethyl-3-methyl-5-(3,4,5-trimethoxyphenyl)-6,7-dihydro-1H-pyrazolo[4,3-e][1,4]diazepin-8-one, 1-Ethyl-5-(3-hydroxyphenyl)-3-methyl-6,7-dihydro-1H-pyrazolo[4,3-e][1,4]diazepin-8-one, 1-Ethyl-5-(2-hydroxyphenyl)-3-methyl-6,7-dihydro-1H-pyrazolo[4,3-e][1,4]diazepin-8-one, 1-Ethyl-3-methyl-5-(2,3,4-trimethoxyphenyl)-6,7-dihydro-1H-pyrazolo[4,3-e][1,4]diazepin-8-one, 1-Ethyl-3,5-diphenyl-6,7-dihydro-1H-pyrazolo[4,3-e][1,4]diazepin-8-one, 1-Ethyl-5-(4-hydroxyphenyl)-3-isopropyl-6,7-dihydro-1H-pyrazolo[4,3-e][1,4]diazepin-8-one, 5-(4-Hydroxyphenyl)-3-isopropyl-1-propyl-6,7-dihydro-1H-pyrazolo[4,3-e][1,4]diazepin-8-one, 3-tert-Butyl-1-ethyl-5-(4-hydroxyphenyl)-6,7-dihydro-1H-pyrazolo[4,3-e][1,4]diazepin-8-one, 5-(2,6-Dimethoxyphenyl)-1-ethyl-3-methyl-6,7-dihydro-1H-pyrazolo[4,3-e][1,4]diazepin-8-one, or 3-Ethoxymethyl-1-ethyl-5-phenyl-6,7-dihydro-1H-pyrazolo[4,3-e][1,4]diazepin-8-one.

8. A method of claim 1 wherein said compound is 1-Ethyl-5-(4-methoxyphenyl)-3-methyl-6,7-dihydro-1H-pyrazolo[4,3-e][1,4]diazepin-8-one, 5-(4-Bromophenyl)-1-ethyl-3-methyl-6,7-dihydro-1H-pyrazolo[4,3-e][1,4]diazepin-8-one, 1-Ethyl-3-methyl-5-naphth-2-yl-6,7-dihydro-1H-pyrazolo[4,3-e][1,4]diazepin-8-one, 5-(3-Chlorothien-2-yl)-1-ethyl-3-methyl-6,7-dihydro-1H-pyrazolo[4,3-e][1,4]diazepin-8-one, Methyl 3-(1-ethyl-3-methyl-8-oxo-1,6,7,8-tetrahydropyrazolo[4,3-e][1,4]diazepin-5-yl)propanoate, 5-(4-Chlorophenyl)-1-ethyl-3-methyl-6,7-dihydro-1H-pyrazolo[4,3-e][1,4]diazepin-8-one, 5-(4-Aminophenyl)-1-ethyl-3-methyl-6,7-dihydro-1H-pyrazolo[4,3-e][1,4]diazepin-8-one, 1-Ethyl-5-(4-fluorophenyl)-3-methyl-6,7-dihydro-1H-pyrazolo[4,3-e][1,4]diazepin-8-one, 5-(3-Bromophenyl)-1-ethyl-3-methyl-6,7-dihydro-1H-pyrazolo[4,3-e][1,4]diazepin-8-one, 3-Methyl-5-phenyl-1-propyl-6,7-dihydro-1H-pyrazolo[4,3-e][1,4]diazepin-8-one, 1-(2-Hydroxyethyl)-3-methyl-5-phenyl-6,7-dihydro-1H-pyrazolo[4,3-e][1,4]diazepin-8-one, 1-Ethyl-3-methyl-5-phenyl-6,7-dihydro-1H-pyrazolo[4,3-e][1,4]diazepin-8-thione, 1-Ethyl-5-(3-methoxyphenyl)-3-methyl-6,7-dihydro-1H-pyrazolo[4,3-e][1,4]diazepin-8-one, 5-(2-Aminophenyl)-1-ethyl-3-methyl-6,7-dihydro-1H-pyrazolo[4,3-e][1,4]diazepin-8-one, 1-Ethyl-5-(2-methoxyphenyl)-3-methyl-6,7-dihydro-1H-yrazolo[4,3-e][1,4]diazepin-8-one, 1-Ethyl-3-isopropyl-5-phenyl-6,7-dihydro-1H-pyrazolo[4,3-e][1,4]diazepin-8-one, 3-tert-Butyl-1-ethyl-5-phenyl-6,7-dihydro-1H-pyrazolo[4,3-e][1,4]diazepin-8-one, 1-Ethyl-3-methyl-5-p-tolyl-6,7-dihydro-1H-pyrazolo[4,3-e][1,4]diazepin-8-one, 5-(3-Aminophenyl)-1-ethyl-3-methyl-6,7-dihydro-1H-pyrazolo[4,3-e][1,4]diazepin-8-one, 3-tert-Butyl-1-ethyl-5-phenyl-6,7-dihydro-1H-pyrazolo[4,3-e][1,4]diazepin-8-thione, 1-Ethyl-3-isopropyl-5-phenyl-6,7-dihydro-1H-pyrazolo[4,3-e][1,4]diazepin-5-thione, 5-(4-Aminophenyl)-3-tert-butyl-1-ethyl-6,7-dihydro-1H-pyrazolo[4,3-e][1,4]diazepin-8-one, 5-(4-Aminophenyl)-1-ethyl-3-isopropyl-6,7-dihydro-1H-pyrazolo[4,3-e][1,4]diazepin-8-one, 1-Ethyl-5-(4-hydroxyphenyl)-3-methyl-6,7-dihydro-1H-pyrazolo[4,3-e][1,4]diazepin-8-one, 5-(4-Aminophenyl)-3-methyl-1-propyl-6,7-dihydro-1H-pyrazolo[4,3-e][1,4]diazepin-8-one, 3-Methyl-5-phenyl-1-(2,2,2-trifluoroethyl)-6,7-dihydro-1H-pyrazolo[4,3-e][1,4]diazepin-8-one, 5-Cyclohexyl-1-ethyl-3-methyl-6,7-dihydro-1H-pyrazolo[4,3-e][1,4]diazepin-8-one, 1-Ethyl-3-methyl-5-pyrid-4-yl-6,7-dihydro-1H-pyrazolo[4,3-e][1,4]diazepin-8-one, 5-tert-Butyl-1-ethyl-3-methyl-4,5,6,7-tetrahydro-1H-pyrazolo[4,3-e][1,4]diazepin-8-one, 3-Butyl-1-ethyl-5-phenyl-6,7-dihydro-1H-pyrazolo[4,3-e][1,4]diazepin-8-one, 5-tert-Butyl-1-ethyl-3-isopropyl-6,7-dihydro-1H-pyrazolo[4,3-e][1,4]diazepin-8-one, 1-Ethyl-3-isopropyl-5-p-tolyl-6,7-dihydro-1H-pyrazolo[4,3-e][1,4]diazepin-8-one, 4-(1-Ethyl-3-isopropyl-8-oxo-1,6,7,8-tetrahydropyrazolo[4,3-e][1,4]diazepin-5-yl)benzonitrile, 5-(2,4-Dimethoxyphenyl)-1-ethyl-3-isopropyl-6,7-dihydro-1H-pyrazolo[4,3-e][1,4]diazepin-8-one, 5-tert-Butyl-3-isopropyl-1-propyl-6,7-dihydro-1H-pyrazolo[4,3-e][1,4]diazepin-8-one, 3-isopropyl-1-propyl-5-p-tolyl-6,7-dihydro-1H-pyrazolo[4,3-e][1,4]diazepin-8-one, 4-(3-isopropyl-8-oxo-1-propyl-1,6,7,8-tetrahydropyrazolo[4,3-e][1,4]diazepin-5-yl)benzonitrile, 5-(2,4-Dimethoxyphenyl)-3-isopropyl-1-propyl-6,7-dihydro-1H-pyrazolo[4,3-e][1,4]diazepin-8-one,
3,5-Di-tert-buty-1-ethyl-6,7-dihydro-1H-pyrazolo[4,3-e][1,4]diazepin-8-one,
3-tert-Butyl-1-ethyl-5-p-tolyl-6,7-dihydro-1H-pyrazolo[4,3-e][1,4]diazepin-8-one,
4-(3-tert-Butyl-1-ethyl-8-oxo-1,6,7,8-tetrahydro-pyrazolo[4,3-e][1,4]diazepin-5-yl)benzonitrile,
3-tert-Butyl-5-(2,4-dimethoxyphenyl)-1-ethyl-6,7-dihydro-1H-pyrazolo[4,3-e][1,4]diazepin-8-one,
3,5-Di-tert-butyl-1-propyl-6,7-dihydro-1H-pyrazolo[4,3-e][1,4]diazepin-8-one,
3-tert-Butyl-1-propyl-5-p-tolyl-6,7-dihydro-1H-pyrazolo[4,3-e][1,4]diazepin-8-one,
4-(3-tert-Butyl-8-oxo-1-propyl-1,6,7,8-tetrahydro-pyrazolo[4,3-e][1,4]diazepin-5-yl)benzonitrile,
3-tert-Butyl-5-(2,4-dimethoxyphenyl)-1-propyl-6,7-dihydro-1H-pyrazolo[4,3-e][1,4]diazepin-8-one,
3-Butyl-1-ethyl-5-phenyl-6,7-dihydro-1H-pyrazolo[4,3-e][1,4]diazepin-8-thione,
1-Ethyl-3-methyl-5-pyrid-3-yl-6,7-dihydro-1H-pyrazolo[4,3-e][1,4]diazepin-8-one,
1-Ethyl-3-methyl-5-pyrid-2-yl-6,7-dihydro-1H-pyrazolo[4,3-e][1,4]diazepin-8-one,
1-Ethyl-3-methyl-5-phenyl-1,6-dihydropyrazolo[4,3-e][1,4]diazepin-8-ylcyanamide,
N-[4-(1-Ethyl-3-methyl-8-oxo-1,6,7,8-tetrahydro-pyrazolo[4,3-e][1,4]diazepin-5-yl)phenyl]-(phenylsulphonyl)benzenesulphonamide,
1-Ethyl-3-isopropyl-5-phenyl-6,7-dihydro-1H-pyrazolo[4,3-e][1,4]diazepin-8-ylidenecyanamide,
3-tert-Butyl-1-ethyl-5-phenyl-6,7-dihydro-1H-pyrazolo[4,3-e][1,4]diazepin-8-ylidenecyanamide,
1-Cyclopropylmethyl-3-methyl-5-phenyl-6,7-dihydro-1H-pyrazolo[4,3-e][1,4]diazepin-8-one,
1-Allyl-3-methyl-5-phenyl-6,7-dihydro-1H-pyrazolo[4,3-e][1,4]diazepin-8-one,
1-Ethyl-3-methyl-5-(4-trifluoromethylphenyl)-6,7-dihydro-1H-pyrazolo[4,3-e][1,4]diazepin-8-one,
1-Ethyl-3-isopropyl-5-(4-trifluoromethylphenyl)-6,7-dihydro-1H-pyrazolo[4,3-e][1,4]diazepin-8-one,
3-tert-Butyl-1-ethyl-5-(4-trifluoromethylphenyl)-6,7-dihydro-1H-pyrazolo[4,3-e][1,4]diazepin-8-one,
3-isopropyl-1-propyl-5-p-tolyl-6,7-dihydro-1H-pyrazolo[4,3-e][1,4]diazepin-8-thione,
3,5-Di-tert-butyl-1-propyl-6,7-dihydro-1H-pyrazolo[4,3-e][1,4]diazepin-8-thione,
5-tert-Butyl-3-isopropyl-1-propyl-6,7-dihydro-1H-pyrazolo[4,3-e][1,4]diazepin-8-thione,
1-Ethyl-3-isopropyl-5-p-tolyl-6,7-dihydro-1H-pyrazolo[4,3-e][1,4]diazepin-8-thione,
5-tert-Butyl-1-ethyl-3-isopropyl-6,7-dihydro-1H-pyrazolo[4,3-e][1,4]diazapin-8-thione,
(±)3-sec-Butyl-1-ethyl-5-phenyl-6,7-dihydro-1H-pyrazolo[4,3-e][1,4]diazepin-8-one,
(±)3-sec-Butyl-1-ethyl-5-pyrid-4-yl-6,7-dihydro-1H-pyrazolo[4,3-e][1,4]diazepin-8-one,
(±)3-sec-Butyl-5-phenyl-1-propyl-4-yl-6,7-dihydro-1H-pyrazolo[4,3-e][1,4]diazepin-8-one,
(±)3-sec-Butyl-1-propyl-5-pyrid-4-yl-6,7-dihydro-1H-pyrazolo[4,3-e][1,4]diazepin-8-one,
3-Cyclohexyl-1-ethyl-5-phenyl-4-yl-6,7-dihydro-1H-pyrazolo[4,3-e][1,4]diazepin-8-one,
3-Cyclohexyl-1-ethyl-5-pyrid-4-yl-6,7-dihydro-1H-pyrazolo[4,3-e][1,4]diazepin-8-one,
3-Cyclohexyl-5-phenyl-1-propyl-4-yl-6,7-dihydro-1H-pyrazolo[4,3-e][1,4]diazepin-8-one,
3-Cyclohexyl-1-propyl-5-pyrid-4-yl-6,7-dihydro-1H-pyrazolo[4,3-e][1,4]diazepin-8-one,
3-Cyclohexylmethyl-1-ethyl-5-pyrid-4-yl-6,7-dihydro-1H-pyrazolo[4,3-e][1,4]diazepin-8-one,
3-Cyclohexylmethyl-5-phenyl-1-propyl-6,7-dihydro-1H-pyrazolo[4,3-e][1,4]diazepin-8-one,
3-Cyclohexylmethyl-1-propyl-5-pyrid-4-yl-6,7-dihydro-1H-pyrazolo[4,3-e][1,4]diazepin-5-one,
3-Cyclohexylmethyl-1-ethyl-5-phenyl-6,7-dihydro-1H-pyrazolo[4,3-e][1,4]diazepin-8-one,
1-Ethyl-8-oxo-5-phenyl-1,6,7,8-tetrahydropyrazolo[4,3-e][1,4]diazepin-3-carboxylic acid ethyl ester,
5-tert-Butyl-1-ethyl-3-isopropyl-6,7-dihydro-1H-pyrazolo[4,3-e][1,4]diazapin-8-ylidenecyanamide,
1-Ethyl-3-isopropyl-5-p-tolyl-6,7-dihydro-1H-pyrazolo[4,3-e][1,4]diazepin-8-ylidenecyanamide,
1-Ethyl-3-isopropyl-5-(4-methoxyphenyl)-6,7-dihydro-1H-pyrazolo[4,3-e][1,4]diazepin-8-one,
1-Ethyl-5-(4-methoxyphenyl)-3-methyl-6,7-dihydro-1H-pyrazolo[4,3-e][1,4]diazepin-8-thione,
1-Ethyl-5-(4-methoxyphenyl)-3-methyl-6,7-dihydro-1H-pyrazolo[4,3-e][1,4]diazepin-8-ylidenecyanamide,
3-isopropyl-5-(4-methoxyphenyl)-1-propyl-6,7-dihydro-1H-pyrazolo[4,3-e][1,4]diazepin-8-one,
3-tert-Butyl-1-ethyl-5-(4-methoxyphenyl)-6,7-dihydro-1H-pyrazolo[4,3-e][1,4]diazepin-8-one,
3-tert-Butyl-5-(4-methoxyphenyl)-1-propyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-ylidenecyanamide,
(±)3-sec-Butyl-1-ethyl-5-(4-methoxyphenyl)-6,7-dihydro-1H-pyrazolo[4,3-e][1,4]diazepin-8-one,
(±)3-sec-Butyl-5-(4-methoxyphenyl)-1-propyl-6,7-dihydro-1H-pyrazolo[4,3-e][1,4]diazepin-8-one,
1-Ethyl-3-methyl-5-(3,4,-trimethoxyphenyl)-6,7-dihydro-1H-pyrazolo[4,3-e][1,4]diazepin-8-one,
1-Ethyl-5-(3-hydroxyphenyl)-3-methyl-6,7-dihydro-1H-pyrazolo[4,3-e][1,4]diazepin-8-one,
1-Ethyl-5-(2-hydroxyphenyl)-3-methyl-6,7-dihydro-1H-pyrazolo[4,3-e][1,4]diazepin-8-one,
1-Ethyl-3,5-diphenyl-6,7-dihydro-1H-pyrazolo[4,3-e][1,4]diazepin-8-one,
1-Ethyl-5-(4-hydroxyphenyl)-3-isopropyl-6,7-dihydro-1H-pyrazolo[4,3-e][1,4]diazepin-8-one,
5-(4-Hydroxyphenyl)-3-isopropyl-1-propyl-6,7-dihydro-1H-pyrazolo[4,3-e][1,4]diazepin-8-one,
3-tert-Butyl-1-ethyl-5-(4-hydroxyphenyl)-6,7-dihydro-1H-pyrazolo[4,3-e][1,4]diazepin-8-one, or
3-Ethoxymethyl-1-ethyl-5-phenyl-6,7-dihydro-1H-pyrazolo[4,3-e][1,4]diazepin-8-one.

9. A method of claim 1 wherein said compound is 1-Ethyl-3-methyl-5-phenyl-6,7-dihydro-1H-pyrazolo[4,3-e][1,4]diazepin-8-thione,
1-Ethyl-5-(2-methoxyphenyl)-3-methyl-6,7-dihydro-1H-yrazolo[4,3-e][1,4]diazepin-8-one,
1-Ethyl-3-isopropyl-5-phenyl-6,7-dihydro-1H-pyrazolo[4,3-e][1,4]diazepin-8-one,
3-tert-Butyl-1-ethyl-5-phenyl-6,7-dihydro-1H-pyrazolo[4,3-e][1,4]diazepin-8-one, 3-tert-Butyl-1-ethyl-5-phenyl-6,7-dihydro-1H-pyrazolo [4,3-e][1,4]diazepin-8-thione,
1-Ethyl-3-isopropyl-5-phenyl-6,7-dihydro-1H-pyrazolo [4,3-e][1,4]diazepin-8-thione,
5-(4-Aminophenyl)-3-tert-butyl-1-ethyl-6,7-dihydro-1H-pyrazolo[4,3-e][1,4]diazepin-8-one,
5-(4-Aminophenyl)-1-ethyl-3-isopropyl-6,7-dihydro-1H-pyrazolo[4,3-e][1,4]diazepin-8-one,
1-Ethyl-5-(4-hydroxyphenyl)-3-methyl-6,1-dihydro-1H-pyrazolo[4,3-e][1,4]diazepin-8-one,
5-Cyclohexyl-1-ethyl-3-methyl-6,7-dihydro-1H-pyrazolo [4,3-e][1,4]diazepin-8-one,
1-Ethyl-3-methyl-5-pyrid-4-yl-6,7-dihydro-1H-pyrazolo [4,3-e][1,4]diazepin-8-one,
5-tert-Butyl-1-ethyl-3-methyl-4,5,6,7-tetrahydro-1H-pyrazolo[4,3-e][1,4]diazepin-8-one,
3-Butyl-1-ethyl-5-phenyl-6,7-dihydro-1H-pyrazolo[4,3-e][1,4]diazepin-8-one,
5-tert-Butyl-1-ethyl-3-isopropyl-6,7-dihydro-1H-pyrazolo[4,3-e][1,4]diazepin-8-one,
1-Ethyl-3-isopropyl-5-p-tolyl-6,7-dihydro-1H-pyrazolo [4,3-e][1,4]diazepin-8-one,
4-(1-Ethyl-3-isopropyl-8-oxo-1,6,7,8-tetrahydro-pyrazolo[4,3-e][1,4]diazepin-5-yl)benzonitrile,
5-(2,4-Dimethoxyphenyl)-1-ethyl-3-isopropyl-6,7-dihydro-1H-pyrazolo[4,3-e][1,4]diazepin-8-one,
5-tert-Butyl-3-isopropyl-1-propyl-6,7-dihydro-1H-pyrazolo[4,3-e][1,4]diazepin-8-one,
3-Isopropyl-1-propyl-5-p-tolyl-6,7-dihydro-1H-pyrazolo [4,3-e][1,4]diazepin-8-one,
4-(3-Isopropyl-8-oxo-1-propyl-1,6,7,8-tetrahydropyrazolo[4,3-e][1,4]diazepin-5-yl) benzonitrile,
5-(2,4-Dimethoxyphenyl)-3-isopropyl-1-propyl-6,7-dihydro-1H-pyrazolo[4,3-e][1,4]diazepin-8-one,
3,5-Di-tert-butyl-1-ethyl-6,7-dihydro-1H-pyrazolo[4,3-e] [1,4]diazepin-8-one,
3-tert-Butyl-1-ethyl-5-p-tolyl-6,7-dihydro-1H-pyrazolo [4,3-e][1,4]diazepin-8-one,
4-(3-tert-Butyl-1-ethyl-8-oxo-1,6,7,8-tetrahydropyrazolo [4,3-e][1,4]diazepin-5-yl)benzonitrile,
3-Butyl-1-ethyl-5-phenyl-6,7-dihydro-1H-pyrazolo[4,3-e][1,4]diazepin-8-thione,
1-Ethyl-3-methyl-5-phenyl-1,6-dihydropyrazolo[4,3-e] [1,4]diazepin-8-ylcyanamide,
1-Ethyl-3-isopropyl-5-phenyl-6,7-dihydro-1H-pyrazolo [4,3-e][1,4]diazepin-8-ylidenecyanamide,
3-tert-Butyl-1-ethyl-5-phenyl-6,7-dihydro-1H-pyrazolo [4,3-e][1,4]diazepin-8-ylidenecyanamide,
1-Ethyl-3-isopropyl-5-p-tolyl-6,7-dihydro-1H-pyrazolo [4,3-e][1,4]diazepin-8-thione,
(±)3-sec-Butyl-1-ethyl-5-phenyl-6,7-dihydro-1H-pyrazolo[4,3-e][1,4]diazepin-8-one,
(±)3-sec-Butyl-1-ethyl-5-pyrid-4-yl-6,7-dihydro-1H-pyrazolo[4,3-e][1,4]diazepin-8-one,
(±)3-sec-Butyl-1-propyl-5-pyrid-4-yl-6,7-dihydro-1H-pyrazolo[4,3-e][1,4]diazepin-8-one,
3-Cyclohexyl-1-ethyl-5-pyrid-4-yl-6,7-dihydro-1H-pyrazolo[4,3-e][1,4]diazepin-8-one,
3-Cyclohexyl-1-propyl-5-pyrid-4-yl-6,7-dihydro-1H-pyrazolo[4,3-e][1,4]diazepin-8-one,
3-Cyclohexylmethyl-1-ethyl-5-pyrid-4-yl-6,7-dihydro-1H-pyrazolo[4,3-e][1,4]diazepin-8-one, 5-tert-Butyl-1-ethyl-3-isopropyl-6,7-dihydro-1H-pyrazolo[4,3-e][1,4]diazepin-8-ylidenecyanamide,
1-Ethyl-3-isopropyl-5-p-tolyl-6,7-dihydro-1H-pyrazolo [4,3-e][1,4]diazepin-8-ylidenecyanamide,
1-Ethyl-3-isopropyl-5-(4-methoxyphenyl)-6,7-dihydro-1H-pyrazolo[4,3-e][1,4]diazepin-8-one,
1-Ethyl-5-(4-methoxyphenyl)-3-methyl-6,7-dihydro-1H-pyrazolo[4,3-e][1,4]diazepin-8-ylidenecyanamide,
3-Isopropyl-5-(4-methoxyphenyl)-1-propyl-6,7-dihydro-1H-pyrazolo[4,3-e][1,4]diazepin-8-one,
3-tert-Butyl-5-(4-methoxyphenyl)-1-propyl-6,7-dihydro-1H-pyrazolo[4,3-e][1,4]diazepin-8-one,
1-Ethyl-5-(4-hydroxyphenyl)-3-methyl-6,7-dihydro-1H-pyrazolo[4,3-e][1,4]diazepin-8-ylidenecyanamide,
(±)3-sec-Butyl-1-ethyl-5-(4-methoxyphenyl)-6,7-dihydro-1H-pyrazolo[4,3-e][1,4]diazepin-8-one,
1-Ethyl-3-methyl-5-(3,4,5-trimethoxyphenyl)-6,7-dihydro-1H-pyrazolo[4,3-e][1,4]diazepin-8-one,
1-Ethyl-5-(3-hydroxyphenyl)-3-methyl-6,7-dihydro-1H-pyrazolo[4,3-e][1,4]diazepin-8-one,
1-Ethyl-5-(2-hydroxyphenyl)-3-methyl-6,7-dihydro-1H-pyrazolo[4,3-e][1,4]diazepin-8-one,
1-Ethyl-3,5-diphenyl-6,7-dihydro-1H-pyrazolo[4,3-e][1, 4]diazepin-8-one,
1-Ethyl-5-(4-hydroxyphenyl)-3-isopropyl-6,7-dihydro-1H-pyrazolo[4,3-e][1,4]diazepin-8-one,
5-(4-Hydroxyphenyl)-3-isopropyl-1-propyl-6,7-dihydro-1H-pyrazolo[4,3-e][1,4]diazepin-8-one,
3-tert-Butyl-1-ethyl-5-(4-hydroxyphenyl)-6,7-dihydro-1H-pyrazolo[4,3-e][1,4]diazepin-8-one, or
3-Ethoxymethyl-1-ethyl-5-phenyl-6,7-dihydro-1H-pyrazolo[4,3-e][1,4]diazepin-8-one.

10. A method of claim 1 wherein said compound is 1-Ethyl-3-methyl-5-phenyl-6,7-dihydro-1H-pyrazolo[4,3-e] [1,4]diazepin-8-thione,
1-Ethyl-3-isopropyl-5-phenyl-6,7-dihydro-1H-pyrazolo [4,3-e][1,4]diazepin-8-one,
3-tert-Butyl-1-ethyl-5-phenyl-6,7-dihydro-1H-pyrazolo [4,3-e][1,4]diazepin-8-one,
3-tert-Butyl-1-ethyl-5-phenyl-6,7-dihydro-1H-pyrazolo [4,3-e][1,4]diazepin-8-thione,
1-Ethyl-3-isopropyl-5-phenyl-6,7-dihydro-1H-pyrazolo [4,3-e][1,4]diazepin-8-thione,
5-(4-Aminophenyl)-3-tert-butyl-1-ethyl-6,7-dihydro-1H-pyrazolo[4,3-e][1,4]diazepin-8-one,
5-(4-Aminophenyl)-1-ethyl-3-isopropyl-6,7-dihydro-1H-pyrazolo[4,3-e][1,4]diazepin-8-one,
3-Butyl-1-ethyl-5-phenyl-6,7-dihydro-1H-pyrazolo[4,3-e][1,4]diazepin-8-one,
5-tert-Butyl-1-ethyl-3-isopropyl-6,7-dihydro-1H-pyrazolo[4,3-e][1,4]diazepin-8-one,
1-Ethyl-3-isopropyl-5-p-tolyl-6,7-dihydro-1H-pyrazolo [4,3-e][1,4]diazepin-8-one,
4-(1-Ethyl-3-isopropyl-8-oxo-1,6,7,8-tetrahydropyrazolo [4,3-e][1,4]diazepin-5-yl)benzonitrile,
5-tert-Butyl-3-isopropyl-1-propyl-6,7-dihydro-1H-pyrazolo[4,3-e][1,4]diazepin-8-one,
4-(3-Isopropyl-8-oxo-1-propyl-1,6,7,8-tetrahydropyrazolo[4,3-e][1,4]diazepin-5-yl) benzonitrile,
3,5-Di-tert-butyl-1-ethyl-6,7-dihydro-1H-pyrazolo[4,3-e] [1,4]diazepin-8-one, 3-tert-Butyl-1-ethyl-5-p-tolyl-6,7-dihydro-1H-pyrazolo[4,3-e][1,4]diazepin-8-one, 4-(3-tert-Butyl-1-ethyl-8-oxo-1,6,7,8-tetrahydropyrazolo[4,3-e][1,4]diazepin-5-yl)benzonitrile, 3-Butyl-1-ethyl-5-phenyl-6,7-dihydro-1H-pyrazolo[4,3-e][1,4]diazepin-8-thione, 1-Ethyl-3-methyl-5-phenyl-1,6-dihydropyrazolo[4,3-e][1,4]diazepin-8-ylcyanamide, 1-Ethyl-3-isopropyl-5-phenyl-6,7-dihydro-1H-pyrazolo[4,3-e][1,4]diazepin-8-ylidenecyanamide, 3-tert-Butyl-1-ethyl-5-phenyl-6,7-dihydro-1H-pyrazolo[4,3-e][1,4]diazepin-8-ylidenecyanamide, 1-Ethyl-3-isopropyl-5-p-tolyl-6,7-dihydro-1H-pyrazolo[4,3-e][1,4]diazepin-8-thione, (±)3-sec-Butyl-1-ethyl-5-phenyl-6,7-dihydro-1H-pyrazolo[4,3-e][1,4]diazepin-8-one, (±)3-sec-Butyl-1-ethyl-5-pyrid-4-yl-6,7-dihydro-1H-pyrazolo[4,3-e][1,4]diazepin-8-one, (±)3-sec-Butyl-1-propyl-5-pyrid-4-yl-6,7-dihydro-1H-pyrazolo[4,3-e][1,4]diazepin-8-one, 3-Cyclohexyl-1-ethyl-5-pyrid-4-yl-6,7-dihydro-1H-pyrazolo[4,3-e][1,4]diazepin-8-one, 3-Cyclohexyl-1-propyl-5-pyrid-4-yl-6,7-dihydro-1H-pyrazolo[4,3-e][1,4]diazepin-8-one, 3-Cyclohexylmethyl-1-ethyl-5-pyrid-4-yl-6,7-dihydro-1H-pyrazolo[4,3-e][1,4]diazepin-8-one, 5-tert-Butyl-1-ethyl-3-isopropyl-6,7-dihydro-1H-pyrazolo[4,3-e][1,4]diazapin-8-ylidenecyanamide, 1-Ethyl-3-isopropyl-5-p-tolyl-6,7-dihydro-1H-pyrazolo[4,3-e][1,4]diazepin-8-ylidenecyanamide, 1-Ethyl-5-(4-hydroxyphenyl)-3-isopropyl-6,7-dihydro-1H-pyrazolo[4,3-e][1,4]diazepin-8-one, 5-(4-Hydroxyphenyl)-3-isopropyl-1-propyl-6,7-dihydro-1H-pyrazolo[4,3-e][1,4]diazepin-8-one, 3-tert-Butyl-1-ethyl-5-(4-hydroxyphenyl)-6,7-dihydro-1H-pyrazolo[4,3-e][1,4]diazepin-8-one.

11. A method of claim 1 wherein said compound is 1-Ethyl-3-isopropyl-5-phenyl-6,7-dihydro-1H-pyrazolo[4,3-e][1,4]diazepin-8-one, 3-tert-Butyl-1-ethyl-5-phenyl-6,7-dihydro-1H-pyrazolo[4,3-e][1,4]diazepin-8-one, 1-Ethyl-3-isopropyl-5-phenyl-6,7-dihydro-1H-pyrazolo[4,3-e][1,4]diazepin-8-thione, 5-(4-Aminophenyl)-1-ethyl-3-isopropyl-6,7-dihydro-1H-pyrazolo[4,3-e][1,4]diazepin-8-one, 1-Ethyl-5-(4-hydroxyphenyl)-3-methyl-6,7-dihydro-1H-pyrazolo[4,3-e][1,4]diazepin-8-one, 4-(1-Ethyl-3-isopropyl-8-oxo-1,6,7,8-tetrahydropyrazolo[4,3-e][1,4]diazepin-5-yl)benzonitrile, 5-tert-Butyl-3-isopropyl-1-propyl-6,7-dihydro-1H-pyrazolo[4,3-e][1,4]diazepin-8-one, 4-(3-Isopropyl-8-oxo-1-propyl-1,6,7,8-tetrahydropyrazolo[4,3-e][1,4]diazepin-5-yl)benzonitriie, 3-tert-Butyl-1-ethyl-5-p-tolyl-6,7-dihydro-1H-pyrazolo[4,3-e][1,4]diazepin-8-one, 3-Butyl-1-ethyl-5-phenyl-6,7-dihydro-1H-pyrazolo[4,3-e][1,4]diazepin-8-thione, (±)3-sec-Butyl-1-ethyl-5-pyrid-4-yl-6,7-dihydro-1H-pyrazolo[4,3-e][1,4]diazepin-8-one, (±)3-sec-Butyl-1-propyl-5-pyrid-4-yl-6,7-dihydro-1H-pyrazolo[4,3-e][1,4]diazepin-8-one, 3-Cyclohexyl-1-propyl-5-pyrid-4-yl-6,7-dihydro-1H-pyrazolo[4,3-e][1,4]diazepin-8-one, 3-tert-Butyl-5-(4-methoxyphenyl)-1-propyl-6,7-dihydro-1H-pyrazolo[4,3-e][1,4]diazepin-8-one, 1-Ethyl-5-(2-hydroxyphenyl)-3-methyl-6,7-dihydro-1H-pyrazolo[4,3-e][1,4]diazepin-8-one, 3-tert-Butyl-1-ethyl-5-(4-hydroxyphenyl)-6,7-dihydro-1H-pyrazolo[4,3-e][1,4]diazepin-8-one, 1-Ethyl-3-isopropyl-5-phenyl-6,7-dihydro-1H-pyrazolo[4,3-e][1,4]diazepin-8-ylidenecyanamide.

12. A method of claim 1 wherein said ($C_5$–$C_{10}$)aryl is phenyl or pyridyl.

* * * * *